(12) United States Patent
Cadden

(10) Patent No.: US 10,828,267 B2
(45) Date of Patent: Nov. 10, 2020

(54) THERAPEUTIC REGIMENS AND METHODS FOR IMPROVING VISUAL FUNCTION IN VISUAL DISORDERS ASSOCIATED WITH AN ENDOGENOUS RETINOID DEFICIENCY

(71) Applicant: RETINAGENIX THERAPEUTICS, INC., Palo Alto, CA (US)

(72) Inventor: Suzanne Cadden, North Vancouver (CA)

(73) Assignee: RETINAGENIX THERAPEUTICS, INC., Palo Alto, CA (US)

( * ) Notice: Subject to any disclaimer, the term of this patent is extended or adjusted under 35 U.S.C. 154(b) by 0 days.

(21) Appl. No.: 16/005,155

(22) Filed: Jun. 11, 2018

(65) Prior Publication Data

US 2019/0054039 A1 Feb. 21, 2019

Related U.S. Application Data

(63) Continuation of application No. 15/096,048, filed on Apr. 11, 2016, now abandoned, which is a continuation of application No. 14/382,235, filed as application No. PCT/CA2013/050155 on Mar. 1, 2013, now abandoned.

(60) Provisional application No. 61/644,360, filed on May 8, 2012, provisional application No. 61/642,212, filed on May 3, 2012, provisional application No. 61/605,729, filed on Mar. 1, 2012.

(51) Int. Cl.
| | |
|---|---|
| *A61K 31/11* | (2006.01) |
| *A61K 31/232* | (2006.01) |
| *A61K 9/00* | (2006.01) |
| *A61K 31/22* | (2006.01) |

(52) U.S. Cl.
CPC ............ *A61K 31/11* (2013.01); *A61K 9/0053* (2013.01); *A61K 31/22* (2013.01); *A61K 31/232* (2013.01)

(58) Field of Classification Search
None
See application file for complete search history.

(56) References Cited

U.S. PATENT DOCUMENTS

| | | | |
|---|---|---|---|
| 3,196,078 A | 7/1965 | Chatzinoff et al. |
| 3,517,067 A | 6/1970 | Stern |
| 4,022,913 A | 5/1977 | Newmark |
| 4,532,133 A | 7/1985 | Schmidt |
| 5,457,135 A | 10/1995 | Baranowitz et al. |
| 5,620,970 A | 4/1997 | Han et al. |
| 5,837,728 A | 11/1998 | Purcell |
| 5,869,468 A | 2/1999 | Freeman |
| 6,300,328 B1 | 10/2001 | Klimko |
| 6,552,009 B2 | 4/2003 | Achkar |
| 6,696,069 B2 | 2/2004 | Harichian et al. |
| 7,494,222 B2 | 2/2009 | Jackson et al. |
| 7,798,646 B2 | 9/2010 | Jackson et al. |
| 7,951,841 B2 | 5/2011 | Palczewski et al. |
| 8,324,270 B2 | 12/2012 | Maeda et al. |
| 9,173,856 B2 | 11/2015 | Strong et al. |
| 2002/0028849 A1 | 3/2002 | Godkin et al. |
| 2003/0215413 A1 | 11/2003 | Fares et al. |
| 2003/0228277 A1 | 12/2003 | Gehlsen |
| 2004/0022766 A1 | 2/2004 | Acland et al. |
| 2004/0042278 A1 | 3/2004 | Bailey |
| 2004/0077604 A1 | 4/2004 | Lichtenberger |
| 2004/0097587 A1 | 5/2004 | Arbiser |
| 2004/0242704 A1 | 12/2004 | Palczewski et al. |
| 2005/0159662 A1 | 7/2005 | Imanishi et al. |
| 2006/0167088 A1 | 7/2006 | Widder et al. |
| 2006/0177392 A1 | 8/2006 | Walden |
| 2006/0240098 A1 | 10/2006 | Castor |
| 2006/0281821 A1 | 12/2006 | Palczewski et al. |
| 2007/0071872 A1 | 3/2007 | Goeseels et al. |
| 2008/0221208 A1 | 9/2008 | Palczewski et al. |
| 2008/0275133 A1 | 11/2008 | Schwartz et al. |
| 2009/0286808 A1 | 11/2009 | Kaushal et al. |
| 2010/0010084 A1 | 1/2010 | Yu |
| 2010/0035986 A1 | 2/2010 | Maeda et al. |
| 2010/0136108 A1 | 6/2010 | Ditzinger et al. |
| 2011/0034554 A1 | 2/2011 | Washington |
| 2011/0257266 A1 | 10/2011 | Strong et al. |
| 2011/0288170 A1 | 11/2011 | Palczewski et al. |
| 2012/0041073 A1 | 2/2012 | Palczewski et al. |

(Continued)

FOREIGN PATENT DOCUMENTS

| | | |
|---|---|---|
| CA | 2601278 | 9/2005 |
| CA | 2714530 | 8/2009 |

(Continued)

OTHER PUBLICATIONS

Maeda et al., "Effects of long-term administration of 9-cis-retinyl acetate on visual function in mice," Invest Ophthalmol Vis Sci. Jan. 2009;50(1):322-333.*

Extended European Search Report dated Jul. 7, 2015 corresponding to EP13760943.4 filed Mar. 1, 2013; 4 pages.

Travis et al., Diseases Caused by Defects in the Visual Cycle: Retinoids as Potential Therapeutic Agents, Annu. Rev. Pharmacol. Toxicol., vol. 47, pp. 469-512, 2007.

(Continued)

*Primary Examiner* — Jared Barsky

(74) *Attorney, Agent, or Firm* — Mintz Levin Cohn Ferris Glovsky and Popeo PC

(57) ABSTRACT

Disclosed herein are therapeutic regimens for improving visual function in Retinitis Pigmentosa and other visual disorders associated with an endogenous retinoid deficiency in a subject by administering a therapeutically effective amount of a synthetic retinal derivative, for example a 9- or 11-cis retinyl ester, according to the therapeutic regimen which leads to local recovery of visual functions such as visual fields, visual acuity and retinal sensitivity, among others.

16 Claims, 14 Drawing Sheets

(56) References Cited

U.S. PATENT DOCUMENTS

| | | | |
|---|---|---|---|
| 2012/0322891 | A1 | 12/2012 | Palczewski et al. |
| 2013/0072443 | A1 | 3/2013 | Palczewski et al. |
| 2013/0072556 | A1 | 3/2013 | Palczewski et al. |
| 2013/0072557 | A1 | 3/2013 | Maeda et al. |
| 2013/0072558 | A1 | 3/2013 | Maeda et al. |
| 2013/0072559 | A1 | 3/2013 | Palczewski et al. |
| 2013/0072560 | A1 | 3/2013 | Palczewski et al. |
| 2013/0072561 | A1 | 3/2013 | Maeda et al. |
| 2013/0072568 | A1 | 3/2013 | Palczewski et al. |
| 2013/0072569 | A1 | 3/2013 | Palczewski et al. |
| 2013/0079403 | A1 | 3/2013 | Palczewski et al. |
| 2013/0196950 | A1 | 8/2013 | Palczewski et al. |
| 2015/0038582 | A1 | 2/2015 | Cadden |
| 2016/0296478 | A1 | 10/2016 | Cadden |
| 2017/0007565 | A1 | 1/2017 | Boch |
| 2017/0087114 | A1 | 3/2017 | Strong et al. |

FOREIGN PATENT DOCUMENTS

| | | | |
|---|---|---|---|
| CN | 1169854 | | 1/1998 |
| CN | 1455780 | | 11/2003 |
| EP | 184942 | B1 | 8/1990 |
| EP | 0803248 | | 10/1997 |
| EP | 552624 | B1 | 6/2000 |
| GB | 1449027 | | 9/1976 |
| GB | 1452012 | | 10/1976 |
| GB | 1526410 | | 9/1978 |
| JP | 61-275266 | | 5/1986 |
| JP | 6340525 | | 12/1994 |
| JP | 8198746 | | 8/1996 |
| JP | 2003-292414 | | 10/2003 |
| RU | 2106843 | | 3/1998 |
| WO | 1999/029315 | | 6/1995 |
| WO | 1996/024344 | | 8/1996 |
| WO | 1997/003655 | | 2/1997 |
| WO | 1999/009969 | | 3/1999 |
| WO | 1999/020265 | A1 | 4/1999 |
| WO | 2000/068364 | | 11/2000 |
| WO | 2002/055540 | | 7/2002 |
| WO | 2002/082904 | | 10/2002 |
| WO | 2003/039521 | | 5/2003 |
| WO | 2003/045379 | | 6/2003 |
| WO | 2003/059336 | | 7/2003 |
| WO | 2004/082622 | | 9/2004 |
| WO | 2005/048994 | | 6/2005 |
| WO | 20051079774 | | 9/2005 |
| WO | 2006/002097 | | 1/2006 |
| WO | WO-2006002097 | A2 * | 1/2006 ........... C07C 403/10 |
| WO | 2006/033734 | | 3/2006 |
| WO | 2007/056242 | | 5/2007 |
| WO | 2007/092509 | | 8/2007 |
| WO | 1999/020265 | | 4/2009 |
| WO | 2009/102418 | | 8/2009 |
| WO | 2001/001960 | | 1/2011 |
| WO | 2011/034551 | | 3/2011 |
| WO | 2011/132084 | | 10/2011 |

OTHER PUBLICATIONS

Tsujikawa et al., Age at Onset Curves of Retinitis Pigmentosa, Arch. Ophthalmol., vol. 126, No. 3, pp. 337-340, 2008.
Van Hooser et al., Rapid Restoration of Visual Pigment and Function With Oral Retinoid in a Mouse Model of Childhood Blindness, PNAS, vol. 97, No. 15, pp. 8623-8628, Jul. 18, 2000.
Van Hooser et al., Recovery of Visual Functions in a Mouse Model of Leber Congenital Amaurosis, J. Biol. Chem., vol. 277, No. 21, pp. 19173-19182, 2002.
Vesanoid® (tretinoin) capsule, US Label, 14 pages, 2004.
Vitamin Converter, copy known vitamin A conversion, 3 pgs, printed from http://www.robert-forbes.com/resources/vitaminconverter. html on Apr. 19, 2012.
Von Lintig et al., The Biochemical and Structural Basis for Trans-to-cis Isomerization of Retinoids in the Chemistry of Vision, Trends Biochem. Sci., vol. 35, No. 7, pp. 400-410, 2010.
Wada et al., Retinoids and Related Compounds. Part 20.1 Synthesis of (11Z)-8, 18-ethanoretinal and a Conformational Study of the Rhodopsin Chromophore, J. Chem. Soc., Perkins Trans. 1, pp. 1773-1777, 1997.
Wada et al., Retinoids and Related Compounds. Part 26.1 Synthesis of (11Z)-8, 18-propano-and methano-retinals and a Conformational Study of the Rhodopsin Chromophore, J. Chem. Soc., Perkins Trans. 1, pp. 2430-2439, 2001.
Weiser and Somorjai, Bioactivity of cis and dicis Isomers of Vitamin A Esters, internatl. J. Vit. Nutr., vol. 62, pp. 201-208, 1992.
Wingerath et al., Analysis of Cyclic and Acyclic Analogs of Retinol, Retinoic Acid, and Retinal by Laser Desorption Ionization-, Matrix-Assisted Laser Desorption Ionization Mass Spectrometry, and UV/Vis Spectroscopy, Analytical Biochemistry, vol. 272, pp. 232-242, 1999.
Witkovsky et al., Formation, Conversion, and Utilization of Isorhodopsin, Rhodopsin, and Porphyropsin by Rod Photoreceptors in the Xenopus Retina, J. Gen. Physiol, vol. 72, pp. 821-836, 1978.
Woodward et al., The Inflow and Outflow of Anti-Glaucoma Drugs, Trends Pharm. Sci., vol. 25, No. 5, pp. 238-241, 2004.
Wrigstad et al., Ultrastructural Changes of the Retina and the Retinal Pigment Epithelium in Briard Dogs with Hereditary Congenital Night Blindness and Partial Day Blindness, Experimental Eye Research, vol. 55, pp. 805-818, 1992.
www.wrongdiagnosis. com, Symptom: Night Blindness, pp. 1-17, Jun. 3, 2008.
Yamamoto et al., Mutations in the Gene Encoding 11-cis Retinol Dehydrogenase Cause Delayed Dark Adaptation and Fundus Albipunctatus, Nat. Genet., vol. 22, No. 2, pp. 188-191, 1999.
Yan et al., Mechanism of Activation of Sensory Rhodopsin 1: Evidence for a Steric Trigger, Proc. Natl. Acad. Sci. USA, vol. 88, pp. 9412-9416, Nov. 1991.
Yanai et al., Visual Performance Using a Retinal Prosthesis in Three Subjects with Retinitis Pigmentosa, Amer. J. Ophthal., vol. 143, No. 5, pp. 820-827, 2007.
Yoshikami et al., Visual Pigments of the Vitamin A Deficient Rat Following Vitamin A2 Administration, Vision Res., vol. 9, No. 6, pp. 633-646, 1969.
Yoshizawa et al., Photochemistry of Iodopsin, Nature, vol. 214, pp. 566-571, May 6, 1967.
Zankel et al., Bovine Rhodopsin with 11-cis-locked Retinal Chromophore Neither Activates Rhodopsin Kinase Nor Undergoes Conformational Change Upon Irradiation, J. Amer. Chem. Soc., vol. 112, No. 13, pp. 5387-5388, 1990.
Zech et al., Changes in Plasm Cholesterol and Triglyceride Levels After Treatment with Orallsotretinoin, Arch. Dermatol., vol. 119, pp. 987-993, 1983.
Zhang et al., Structure, Alternative Splicing, and Expression of the Human RGS9 Gene, Gene, vol. 240, pp. 23-24, 1999.
Zhu et al., A Naturally Occurring Mutation of the Opsin Gene (T4R) in Dogs Affects Glycosylation and Stability of the G protein-coupled Receptor, J. Biol. Chem., vol. 279, No. 51, pp. 53828-53839, 2004.
Berson et al., Further Evaluation of Docosahexaenoic Acid in Patients with Retinitis Pigmentosa Receiving Vitamin A Treatment: Subgroup Analysis, Arch. Ophthalmol., vol. 122, pp. 1306-1314, 2004.
V.G. Belidov, Farmatsevticheskaya khimiya, [Pharmaceutical Chemistry], M., Vysshaya shkola, 1993, vol. 1, pp. 43-47 (Russian language, English translation).
Batten et al., Pharmacological and rAAV Gene Therapy Rescue of Visual Functions in a Blind Mouse Model of Leber Congenital Amaurosis, PLOS Medicine, vol. 2 , No. 11, pp. 1177-1189, 2005.
Borhan et al., Efficient Synthesis of 11-cis-Retinoids, Chemistry (Europe), vol. 5, pp. 1172-1175, 1999.
Imanishi et al., Retinosomes: New Insights Into Intracellular Managing of Hydrophobic Substances in Lipid Bodies, J. Cell Biology, vol. 166, pp. 447-453, 2004.
Yamamoto et al., Important Role of the Proline Residue in the Signal Sequence That Directs the Secretion of Human Lysozyme in *Saccharomyces cerevisiae*, Biochemistry, vol. 28, pp. 2728-2732, 1989.

(56) References Cited

OTHER PUBLICATIONS

Berson, et al., Further evaluation of docosahexaenoic acid in patients with retinitis pigmentosa receiving vitamin A treatment: subgroup analysis, Arch Ophthalmol., 122:1306-14 (2004).
Revised, Pharmaceutical Additive Handbook (Kaitei Iyakuhin Handobukku), Yakuji Nippo Limited, Feb. 29, 2007, pp. 753-755.
Ablonczy et al., 11-cis-retinyl reduces constitutive opsin phosphorylysation and improves quantum catch in retinoid-deficient mouse rod photoreceptors, J. Biol. Chem., vol. 277, pp. 40491-40498, 2002.
ACCUTANE Label, NDA 18-662/S-056, pp. 11-55.
Acland et al., Long-term restoration of rod and cone vision by single dose rAAV-mediated gene transfer to the retina in a canine model of childhood blindness, Mol. Ther., vol. 12, No. 6, pp. 1072-1082, 2005.
Acland et al., Gene therapy restores vision in canine model of childhood blindness, Nature Genetics,vol. 28, pp. 92-95, 2001.
Aggarwal et al., 2-Halogeno-1,3-dioxide: A diastereoselective carbonyl anion equivalent in reactions with aldehydes, J. Chem. Soc., vol. 1, pp. 11-19, 1997.
Albeck et al., Factors affecting the absorption maxima of acidic forms of bacteriorhodopsin: A study with artificial pigments, Biophys. J., vol. 56, pp. 1259-1265, 1989.
Aleman et al., Impairment of the transient pupillary light reflex in Rpe65(-/-) mice and humans with Leber congenital amaurosis, Investigative Ophthalmology & Visual Science, vol. 45, No. 4, pp. 1259-1271, 2004.
Allen, Estimating the Potential for VitA Toxicity in Women and Young Children, J. Nutr., vol. 132, pp. 2907-2919, 2002.
Ames et al., Biomedical studies on vitamin A. XIV. Biopotencies of Geometric Isomers of Vitamin A Acetate in the Rat, J. Am. Chem. Soc., vol. 77, pp. 4134-4136, 1955.
Asato et al., Flourinated rhodopsin analogues from 10-flouro-and 14-flouroretinal, J. Am. Chem. Soc., vol. 100, No. 18, pp. 5957-5960, 1978.
Baehr et al., The retinoid cycle and retina disease, Vision Research, vol. 43, pp. 2957-2958, 2003.
Bainbridge et al., Effect of gene therapy on visual function in Leber's congenital amaurosis, The New England Journal of Medicine, www.nejm.org, vol. 358, pp. 2231-2239, Apr. 29, 2008.
BASF, Technical Informaiton: Retinol 50C, 15D and 10S, May 2005.
Batten et al., Lecithin-retinol Acyltransferase is Essential for Accumulation of All-trans-Retinyl Esters in the Eye and in the Liver, J. Bio. Chem., vol. 279, 10422-10432, 2004.
Beischel et al., Azidotetrafluorophenyl Retinal Analogue: Synthesis and Bacteriorhodopsin Pigment Formation, Photochemistry and Photobiology, vol. 60, No. 1, pp. 64-68, 1994.
Bernstein et al., Biochemical characterization of the retinoid isomerase system of the eye, J. Biol. Chem., vol. 262, No. 35, pp. 16848-16857, 1987.
Berson et al., A Randomized Trial of Vitamin A and Vitamin E Supplementation for Retinitis Pigmentosa, Arch. Ophthalmol., vol. 111, pp. 761-772, 1993.
Berson et al., Disease progression in patients with dominant retinitis pigmentosa and rhodopsin mutations, Invest. Opthalmol. Vis. Sci., vol. 43, No. 9, pp. 3027-3036, 2002.
Berson et al., Retinitis pigmentosa: Unfolding its mystery, Proc. Natl. Sci USA, vol. 93, pp. 4526-4528, 1996.
Berson, Treatment of retinitis pigmentosa with vitamin A, Digital J. Opthamol., vol. 4, No. 7, Massachusetts Eye and Ear Infirmary, Harvard Medical School, 1998.
Biesalski et al., Sensitive Analysis of Retinyl Esters by Isocratic Absorption Chromatography, J. Clin. Chem. Clin. Biochem., vol. 27, No. 2, pp. 65-74, 1989 (Abstract only).
Birch et al., Validity and Reliability of th eChildren's Visual Function Questionnaire (CVFQ), J AAPOS, vol. 11, No. 5, pp. 473-479, Oct. 2007.
Birnbach et al., Retinoic acid accelerates photoreceptor cell death by apoptosis in Pro23HIS rhodopsin trangenic mice, Invest. Ophthalmol. Vis. Sci., vol. 38, No. 4, pp. s311, 1997.
Bittner et al., Test-retest, within-visit variability of goldmann visual fields in retinitis pigmentosa, Invest. Ophthalmol. Vis. Sci., vol. 52, pp. 8042-8046, 2011.
Boehm et al., Photoaffinity labeling Studies of Bacteriorhodopsin with [15-3H]-3-Diazo-4-keto-all-trans-retinal, J. Am. Chem. Soc., vol. 112, pp. 7779-7782, 1990.
Borhan et al., Chemoenzymatic Synthesis of 11-cis-retinal Photoaffinity Analog by Use of Squid Retinochrome, J. Am. Chem. Soc., vol. 119, pp. 5758-5759, 1997.
Bridges et al., Vitamin A* and the Role of the Pigment Epithelimn during Bleaching and Regeneration of Rhodopsin in the Frog Eye, Exp. Eye Res., vol. 22, pp. 435-455, 1976.
Buczylko et al., Mechanisms of Opsin Activation, J. Biol. Chem., vol. 271, No. 34, pp. 20621-20630, 1996.
Caldwell et al., Synthesis of Retinals with Eight-and Nine-Membered Rings in the Side Chain. Models of Rhodopsin Photobleaching intermediates, J. Org. Chem., vol. 58, pp. 3533-3537, 1993.
Capecchi, altering the genome by homologous recombination, Science, vol. 244, No. 4910, pp. 1288-1292, 1989.
Carney and Russell, Correlation of Dark Adaptation Test Results with Serum Vitamin A Levels in Diseased Adults, J. Nutr., vol. 110, pp. 552-557, 1980.
Caruso et al., Effects of Fenretinide (4-HPR) on Dark Adaptation, XP002475887; STN Database Accession No. 1998:418096 & Archives of Ophthalmology (Chicago), vol. 116, No. 6, pp. 759-763, CODEN: AROPAW: ISSN:0003-9950, 1998 (Abstract Only).
Chan et al., Delated Dark Adaption Caused by Nilutamide, J. Neuro-Ophthalmology, vol. 28, No. 2, pp. 158-159, 2008.
Chapple et al., Looking at Protein Misfolding Neurodegenerative Disease Through Retinitis Pigmentosa, ACNR, vol. 3, Issue 1, pp. 12-13, 2003.
Chatzinoff et al., Eleven-cis Vitamin A in the Treatment of Retinitis Pigmentosa, Arch. Opthalmol., vol. 80, pp. 417-419, 1968.
Chen et al., Inherent Instability of the Retinitis Pigmentosa P23H Mutant Opsin, JBC Papers in Press, Manuscript M114.551713, 31 pages, Latest version can be accessed at http://www.jbc.orb/cgi/doi/10.1074/jbc.M114.551713, Published Feb. 10, 2014.
Christoforidis, Volume of Visual Field Assessed with Kinetic Perimetry and its Application to Static Perimetry, Clin. Ophthalmol, vol. 5, pp. 535-541, 2011.
Cideciyan et al., Human Gene Therapy for RPE65 Isomerase Deficiency Activates the Retinoid Cycle of Vision but with Slow Rod Kinetics, PNAS USA, vol. 105, pp. 15112-15117, 2008.
Cideciyan et al., Rod and Cone Visual Cycle Consequences of a Null Mutation in the 11-cis-Retinol Dehydrogenase Gene in Man, Vis. Neurosci., vol. 17, No. 5, pp. 667-678, 2000.
Colenbrander, Visual Standards Aspects and Ranges of Vision Loss with Emphasis on Population Surveys, Report prepared for the International Council of Ophthalmology at the 29th International Congress of Ophthalmology Sydney, Australia, Apr. 2002, pp. 1-33.
Colmenares et al., 11, 12-Difluororhodopsin and Related Odd-Numbered Fluororhodopsins. The Use of JF, F for Following a Cis-trans Isomerization Process, J. Am. Chem. Soc., vol. 121, pp. 5803-5804, 1999.
Congdon et al., Responsiveness of Dark-Adaptation Threshold to Vitamin A and Beta-carotene Supplementation in Pregnant and Lactating Women in Nepal, Am. J. Clin. Nutr., vol. 72, pp. 1004-1009, 2000.
Corson et al., Sensitization of Bleach Rod Photoreceptors by 11-cis-locked Analogues of Retinal, PNAS USA, vol. 87, pp. 6823-6827, 1990.
Crescitelli et al., Can Isorhodopsin be Produced in the Living Rat?, Vision Res., vol. 13, No. 12, pp. 2515-2525, 1973.
Crescitelli et al., The Spectral Properties and Photosensitivities of Analogue Photopigments Regenerated with 10-and 14-substituted Retinal Analogues, Proc. R. Soc. Lond. B233, pp. 55-76, 1988.
Crouch and Katz, The Effect of Retinal Isomers on the Ver and Erg of Vitamin A Deprived Rats, Vision Res., vol. 20, pp. 109-115, 1980.
Crouch et al., Cycloheptatrienylidene Analog of 11-cis Retinal, Invest. Opthalmol. Vis. Sci., vol. 25, pp. 419-418, 1984.
Crouch et al., Inhibition of Rhodopsin Regeneration of Cyclohexyl Derivatives, Vision Research, vol. 22, No. 12, pp. 1451-1456, 1982.

(56) References Cited

OTHER PUBLICATIONS

Crough et al., Opsin Pigments Formed with Acyclic Retinal Analogues Minimum 'Ring Portion' Requirements for Opsin Pigment Formation, FEBS 158:1, 1983.
Crouch et al., Photosensitive pigments formed with rat opsin, Investigative Opthalmology, vol. 15, No. 10, pp. 872-875, 1976.
Crouch, Yearly Review Studies of Rhodopsin and Bacteriorhodopsin Using Modified Retinals, Photochemistry and Photobiology, vol. 44, No. 6, pp. 803-807, 1986.
Dahl et al., Stability of vitamins in Soybean Oil Fat Emulsion Under Conditions Simulating Intravenous Feeding of Neonates and Children, Journal of Parenteral Enteral Nutrition, vol. 18, pp. 234-239, 1994.
De Grip et al., 10 20-Methanorhodopsins (7E, 9E, 13E)-10 20 Methanorhodopsin and (7E, 9Z, 12Z)-10 20-Methanorhodopsin 11-cis-locked Rhodopsin Analog Pigments with Unusual Thermal and Photostability, Eur. J. Biochem., vol. 191, No. 1, pp. 211-220, 1990.
De Marchi et al., Effects of Isotrentinoin on the Metabolism of Triglyceride-rich Lipoproteins and on the Lipid Profile in Patients with Acne, Arch. Dermatol. Res., pp. 403-408, 2006.
Delange et al., An Additional Methyl Group at the 10-position of Retinal Dramatically Slows Down the Kinetics of the Rhodopsin Photocascade, Biochemistry, vol. 37, No. 5, pp. 1411-1420, 1998.
Den Hollander et al., Prog Ret Eye Res, vol. 27, pp. 391-419, 2008.
Dorwald, Side Reactions in Organic Synthesis: A Guide to Successful Synthesis Design, Wiley-VCH Verlag GmbH & Co. KGaA, Weinheim, Preface p. IX, 2004.
Drachev et al., An Investigation of the Electrochemical Cycle of Bacteriorhodopsin Analogs with the Modified Ring, Arch. Biochem. Biophys., vol. 270, No. 1, pp. 184-197, 1989.
Driessen et al., Disruption of the 11-cis-retinol Dehydrogenase Gene Leads to Accumulation of Cis-retiols and Cis-retinyl Esters, Mol. Cell Biol., vol. 20, No. 12, pp. 4275-4287, 2000.
Ebrey et al., Properties of Several Sterically Modified Retinal Analogs and Their Photosensitive Pigments, Biochemistry, vol. 14 pp. 3933-3941, 1975.
European Search Report From related European Patent Application No. EP 04757476, dated Apr. 29, 2008.
European Search Report From related European Patent Application No. EP 11154402, dated Sep. 5, 2011.
European Search Report From related European Patent Application No. EP 11154404, dated Sep. 6, 2011.
European Search Report From related European Patent Application No. EP 11154534, dated Sep. 5, 2011.
Eyring et al., Assignment and Interpretation of Hydrogen Out-of-Plane Vibrations in the Resonance Raman Spectra of Rhodopsin and Bathorhodopsin, Biochemistry, vol. 21, pp. 384-393, 1982.
Fan et al., Isorhodopsin Rather Than Rhodopsin Mediates Rod Function in RPE65 Knock-out Mice, PNAS, vol. 100, No. 23, pp. 13992-13667, 2003.
Fan et al., Light Prevents Exogenous 11-cis Retinal from Maintaining Cone Photoreceptors in Chromophore-deficient Mice, Invest. Ophthalmol. Vis. Sci., 10-6437, vol. 52, pp. 2412-2416, 2011.
Fazzi et al., Response to Pain in a Group of Healthy Term Newborns: Behavioral and Physiological Aspects, Functional Neurology, vol. 11, pp. 35-43, 1996.
Fazzi et al., Leber's Congenital Amaurosis: An Update, Eur. J. Paediatr. Neural., vol. 7, pp. 13-22, 2003.
Filipek et al., G Protein-Coupled Receptor Rhodopsin: A Prospectus, Annu. Rev. Physiol., vol. 65, pp. 851-879, 2003.
Fujimoto et al., On the Bioactive Conformation of the Rhodopsin, Chemistry, vol. 7, pp. 4198-4204, 2001.
Fujimoto et al., Solution and Biologically Relevant Conformations of Enantiomeric 11-cis-locked Cyclopropyl Retinals, J. Am. Chem. Soc., vol. 124, pp. 7294-7302, 2002.
Fukada et al., Studies on Structure and Function of Rhodopsin by Use of Cyclopentatrienylidene 11-cis-locked Rhodopsin, Biochemistry, vol. 23, No. 24, pp. 5826-5832, 1984.
Futterman et al., The Composition of Liver Vitamin A Ester and the Synthesis of Vitamin A Ester by Liver Microsomes, J. Biol. Chem., vol. 239, No. 12, pp. 4077-4080, 1964.
Gaffney et al., Aging and Cone Dark Adaptation, Optom. Vis. Sci., vol. 89, No. 8, pp. 1219-1224, 2012 (abstract only).
Gao and Hollyfield, Aging of the Human Retina, Inv. Opth. Vis. Sci., vol. 33, pp. 1-17, 1992.
Gartner et al., Guantum Yield of Chapso-Solubilized Rhdopsin and 3-Hydroxy Retinal Containing Bovine Opsin, Photochemistry and Photobiology, vol. 54, No. 6, pp. 1047-1055, 1991.
Gearhart et al., Improvement of Visual Performance with Intravitreal Administration of 9-cis-retinal in Rpe65-mutant Dogs, Arch .Ophthalmol., vol. 128, No. 11, pp. 1442-1448, 2010.
Gennaro et al., Remington: The Science of Practice of Pharmacy, 19th Edition, Mack Publishing Company, pp. 1528-1529, 1995.
Gerber et al., Changes in Lipid Metabolism During Retinoid Administration, J. Amer. Acad. Derm., vol. 6, pp. 664-674, 1982.
Geroski et al., Drug Delivery for Posterior Segment Eye Disease, IOVS, vol. 41, No. 5, pp. 961-964, 2000.
Gollapalli et al., All-trans-retinyl Esters and the Substrates for Isomerization in the Vertebrate Visual Cycle, Biochemistry, vol. 42, No. 19, pp. 5809-5819, 2003.
Grant et al., Treatable Forms of Retinitis Pigmentosa Associated with Systemic Neurological Disorders, Int. Opthalmol. Clin., vol. 41, No. 1, 2001, printed from http://www.ncbi.nim.nih.gov/pubmid/11198137 on Jan. 14, 2009 (abstract only).
Grover et al., Patterns of Visual Field Progression in Patients with Retinitis Pigmentosa, Ophthalmology, vol. 105, pp. 1069-1075, 1998.
Gu et al., Mutations in PRE65 Cause Autosomal Recessive Childhood-onset Severe Retinal Dystrophy, Nature Genetics, vol. 17, pp. 194-197, 1997.
Haeseleer et al., Dual-substrate Specificity Short Chain Retinol Dehydrogenases From the Vertebrate Retina, J. Biol. Chem., vol. 277, No. 47, pp. 45537-45546, 2002.
Haig et al., Vitamin A and Rod-Cone Dark Adaptation in Cirrhoses of the Liver, Science, vol. 87, No. 2267, pp. 534-536, 1938.
Hamel et al., Molecular Cloning and Expression of RPE65, a Novel Retinal Pigment Epithelium-specific Microsomal Protein that is Post-Transcriptionally Regulated in Vitro, J. Bio. Chem., vol. 268, No. 21, pp. 15751-15757, 1993.
Han et al., The C9 Methyl Group of Retinal Interacts with Glycine-121 in Rhodopsin, Proc. Natl. Acad. Sci. USA, vol. 34 pp. 13442-13447, Dec. 1997.
Handbook of Pharmaceutical Excipients, Fifth Ed., Soybean Oils, pp. 722-723, 2006 (3 pages total).
Hartong et al., Retinitis Pigmentosa, Lancet, vol. 368, pp. 1795-1809, 2006.
Harvard Health Publications, The Aging Eye: Preventing and Treating Eye Disease, Harvard Health Publications, 3 pages, 2011, printed from http://www.health.harvard.edu/special_health_reports/the_aging_eye on Nov. 5, 2011.
Head, Natural Therapies for Ocular Disorders, part one: Diseases of the Retina, Alt. Med. Review, vol. 4, No. 5, pp. 342-359, 1999.
Hiraki et al., Bacteriorhodopsin Analog Regenerated with 13-Desmethyl-13-Iodoretinal, Biophys. J., vol. 83, pp. 3460-3469, 2002.
Hirano et al., Constraints of Opsin Structure on the Ligand-binding Site: Studies with Ring-fused Retinals, Photochemistry and Photobiology, vol. 76, No. 6, pp. 606-615, 2002.
Hisatomi et al., Critical Role of Photoreceptor Apoptosis in Functional Damage after Retinal Detachment, Curr. Eye Res., vol. 24, No. 3, pp. 161-172, 2002, abstract only, 1 page, printed from http://www.ncbi.nim.nih.gov/pubmed/12221523.
Howard et al., Comparative Distribution, Pharmacokinetics and Placental Permeabilities of All-trans-retinoic Acid, 13-cis-retinoic acid, All-trans-4-oxo-retinoic acid, retinyl acetate and 9-cis-retinal in Hamsters, Arch. Toxicol., vol. 63, pp. 112-120, 1989.
Hu et al., Unbleachable Rhodopsin with an 11-cis-Locked Eight-Membered Ring Retinal: The Visual Transduction Process, Biochemistry, vol. 33, pp. 408-416, 1994.
Phelan et al., A Brief Review of Retinitis Pigmentosa and the Identified Retinitis Pigmentosa Genes, Mol. Vis., vol. 6, pp. 116-124, 2000.

(56) References Cited

OTHER PUBLICATIONS

Price et al., Mislocalization and Degradation of Human P23H-Rhodopsin-GFP in a Knockin Mouse Model of Retinitis Pigmentosa, Invest. Opthal. Vis. Sci., vol. 52, No. 13, pp. 9728-9736, 2011.
QLT Inc. press release: QLT Announces Results from Phase 1b Trial of QLT091991 in Subjects with Leber Congenital Amaurosis, May 3, 2011 (Feb. 5, 2011), http://www.qltinc.com/newsCenter/2011/110503.htm. see entire document.
Radomska et al., The Use of Some Ingredients for Microemulsion Preparation Containing Retinol and Its Esters, XP002475886, STN Database Accession No. 2000:139945 and International Journal of Pharmaceutics, vol. 196, No. 2, pp. 131-134 CODEN:IJPHDEI; ISSN: 0378-5173, 2000 (abstract only).
Rao et al., 5-(Trifluoromethyl1) Bacteriorhodopsin does Not Translocate Protons, J. Am. Chem. Soc., vol. 108, pp. 6077-6078, 1986.
Rao et al., Isomers of 3, 7, 11-trimethyldodeca-2, 4, 6, 8, 10-Pentaenal (A Linear Analogue of Retinal) and Lower Homologues in Their Interaction with Bovine Opsin and Bacterioopsin, Photochemistry and Photobiology, vol. 41, No. 2, pp. 171-175, 1985.
Rao et al., Regioselective Photo Isomerisation of Retinolacetate, Tetrahedron Leters, vol. 31, No. 24, pp. 3441-3444, 1990.
Redmond et al., Mutation of Key Residues of RPE65 Abolishes its Enzymatic Role as Isomerohydrolse in the Visual Cycle, Proc. Natl. Acad. Sci USA, vol. 102, No. 38, pp. 13658-13663, 2005.
Redmond et al., RPE65 is Necessary for Production of 11-cis-Vitamin A in the Retinal Visual Cycle, Nature Genetics, vol. 20, pp. 344-351, 1998.
Reid et al., Mass Spectral Analysis of Eleven Analogs of Vitamin A1, Lipids, vol. 8, No. 10, pp. 558-565.
Renk et al., A Rhodopsin Pigment Containing a Spin-Labeled Retinal, J. Am. Chem. Soc., vol. 109, pp. 6163-6168, 1987.
Rezabek et al., Effects of Dietary Retinyl Acetate on the Promotion of Hepatic Enzyme-Altered Foci by Polybrominated Biphenyls in Initiated Rats, Food Chem. Toxicol., vol. 27, No. 8, pp. 539-544, 1989 (abstract only).
Ridge et al., Visual Rhodopsin Sees the Light: Structure and Mechanism of G Protein Signaling, J. Bio. Chem., vol. 282, No. 13, pp. 9297-9301, 2007.
Robinson et al., Opsins with Mutations at the Site of Chromophore Attachment Constitutively Activate Transducin but are not Phosphorylated by Rhodopsin Kinase, Proc. Natl. Acad. Sci. USA, vol. 91, No. 12, pp. 5411-5415, 1994.
Roman et al., Full-Field Stimulus Testing (EST) to Quantify Visual Perception in Severely Blind Candidates for Treatment Trials, Physiol. Meas., vol. 28, pp. N51-N56, 2007.
Rotenstreich et al., Treatment of Retinal Dystrphy, Fundus albipunctatus, With Oral 9-cis-b-carotene, Br. J. Opthalmol., vol. 94, pp. 616-621, 2010.
Rotenstreich et al., Treatment with 9-cis-beta-carotene-rich Powder in Patients with Retinitis Pigmentosa: A Randomized Crossover Trial, JAMA Ophthalmol., vol. 131, pp. 985-992, 2013.
Russell, The Vitamin A Spectrum: From Deficiency to Toxicity, Am. J. Clin. Nutr., vol. 71, pp. 878-884, 2000.
Sakami et al., Probing Mechanisms of Photoreceptor Degeneration in a new Mouse Model of the Common Form of Autosomal Dominant Retinitis Pigmentosa due to P23H Opsin Mutations, JBC Papers in Press, Manuscript M110.209759, 29 pages, Latest version can be accessed at http://www.jbc.org/cgi/doi/10.1074/jbc.M110.209759, published Jan. 11, 2011.
Saliba et al., The Cellular Fate of Mutant Rhodopsin: Quality Control, Degradation and Aggresome Formation, J. Cell Science, vol. 115, pp. 2907-2918, 2002.
Sandberg et al., Clinical Expression Correlates With Location of Rhodopsin Mutation in Dominant Retinitis Pigmentosa, Invest. Opthalmol. Vis. Sci., vol. 36, No. 9, pp. 1934-1942, 1995.
Schatz et al., Fundus Albipunctatus Associated With Compound Heterozygous Mutations in RPE65, Ophthalmology, vol. 118, pp. 888-894, 2011.
Sekiya et al., Effect of Modification of the Chromophore in Retinochrome, Biophys, Chem., vol. 56, pp. 31-39, 1995.

Semenova et al., Stabilization of All-trans-Retinol by Cyclodextrins: A Comparative Study Using HPLC and Flourescence Spectroscopy, XP002475883; STN Database Accession No. 2003:494986 and Journal of Inclusion Phenomena and Macrocyclic Chemistry, vol. 44, No. 1-4, pp. 155-158, CODEN:JIPCF5, ISSN:1388-3217, 2003 (abstract only).
Semenova et al., Systems for Delivery of Vitamin A to the Retina in Retinitis Pigmentosa, XP002475884, STN Database Accession No. 2002:438129 and New Insights Into Retinal Degenerative Diseases, Proceedings of the International Symposium on Retinal Degeneration, 9th, Durango, CO, USA, Meeting Date 2000, pp. 105-110, Editor Anderson & Lavail, 2001 (abstract only).
Semple-Rowland et al., A Null Mutation in the Photoreceptor Guanylate Cyclase Gene Causes the Retinal Degeneration Chicken Phenotype, Proc. Natl. Acad. Sci. USA, vol. 95, No. 3, pp. 1271-1276, 1998.
Sen et al., Synthesis and Binding Studies of Photoaffinity Label for Bovine Rhodopsin, J. American Chem. Soc., vol. 104, pp. 3214-3216, 1982.
Sibulesky et al., Savety of <7500 RE (<25000 IU) Vitamin A Daily in Adults with Retinitis Pigmentosa, Am. J. Clin. Nutr., vol. 69, pp. 656-663, 1999.
Silverman, Hyervitaminosis A Syndrom: A Paradigm of Retinoid Side Effects, J. Am. Adac. Derm., vol. 16, pp. 1027-1039, 1987.
Sokal et al., GCAP1 (Y99C) Mutant is Constitutively Active in Autosomal Dominant Cone Dystropy, Mol. Cell., vol. 2, No. 1, pp. 129-133, 1998.
Soriatane® (acitretin) capsule US Label, 2009, and Principal Display Panels, 24 pages.
Spaeth, Ophthalmic Surgery: Principles of Practice, Ed., pp. 85-87, 1990, W.B. Sanders Co., Philadelphia, PA, USA.
Stecher et al., Preferential Release of 11-cis-Retinol From Retinal Pigment Epithelial Cells in the Presence of Cellular Retinaldehyde-binding Protein, J. Biol. Chem., vol. 274, No. 13, pp. 8577-8585, 1999.
Steinberg et al., Isomer Composition and Spectra of the Dark and Light Adapted Forms of Artificial Bacteriorhodopsins, Photochem. and Photobiol., vol. 54, No. 6, pp. 969-976, 1991.
Supplementary European Search Report from Related European Patent Application No. EP 05773576, dated Aug. 4, 2008.
Taha et al., Preparation and in vito Characterization of Self-Nanoemulsified Drug Delivery System (SNEDDS) of All-trans-retinol Acetate, International Journal of Pharmaceutics, vol. 285, No. 1-2, pp. 109-119, 2004.
Tan et al., Absolute Sense of Twist of the C12-C13 Bond of the Retinal Chromophore in Bovine Rhodopsin Based on Exciton-Coupled CD Spectra of 11, 12-Dihydroretinal Analogues, Anxeu Cben7 Inr Ed Engl, vol. 26, No. 19, pp. 2089-2083, 1997.
Targretin® (bexarotene) capsule US Label, 14 pages, 2006.
Tarkhov et al., Study of a Structure-Properly Relationship for Retinal Derivatives Taking Into Account Their Conformational Flexibility, Chemical Abstracts, vol. 128, No. 18, pp. 270, 1998, Abstract No. 128:214600 (abstract only).
Teelmann, Retinoids: Toxicity and Teratogenicity to Date, Pharmac. Ther., vol. 40, pp. 29-43, 1989.
Teller et al., Advances in Determination of a High-Resolution Three-Dimensional Structure of Rhodopsin, A Model of G-Protein-Coupled Receptors (GPCRs), Biochemistry, vol. 40, No. 26, pp. 7731-7772, 2001.
The Eye Digest, Aging Eye in the US, 2 pgs, 2011, printed from http://web.archive.org/web/20060810014820/http://www.agingeye.net/mainnews/usaging.php.
The K-Zone, Biophysical data tables; standard man, Jul. 2004, printed Mar. 14, 2009 from http://www.kevinboone.com/biodat_stdman.html, 1 page.
Thompson et al., Genetic Defects in Vitamin A Metabolism of the Retinal Pigment Epithelium, Genetics in Ophthalmology, vol. 37, pp. 141-154, 2003.
Thompson et al., Genetics and Phenotypes of RPE65 Mutations in Inherited Retinal Degeneration, Invest Ophthal. Vis. Sci., vol. 41, No. 13, pp. 4293-4299, 2000.

(56) References Cited

OTHER PUBLICATIONS

Thompson et al., Mutations in the Gene Encoding Lecithin Retinol Acyltransferace Are Associated With Early-Onset Severe Retinal Dystrophy, Nat. Gen., vol. 28, pp. 123-124, 2001.
Thomson Scientific, London, GB; AN 1995-063773, XP002475888 & JP 06340525 A (Lion Corp); Dec. 13, 1994 (abstract only).
Thomson Scientific, London, GB; AN 1996-408307, XP002475889 & JP 08198746 A (Lion Corp); Aug. 6, 1996 (abstract only).
Thomson Scientific, London, GB; AN 1998-518867, XP002475890 & RU 2106843 C1 (Krasy Med Acad); Mar. 20, 1998 (abstract only).
Toctino™ (alitretinoin) capsule Canadian Product Monograph, 34 pages, 2011.
Maeda et al., A Critical Role of CaBP4 in the Cone Synapse, Invest. Opthalmol. Vis. Sci., vol. 46, No. 11, pp. 4320-4327, 2005.
Maeda et al., Effects of Long-Term Administration of 9-cis-Retinyl Acetate on Visual Function in Mice, Invest. Opthalmol. Vis. Sci., vol. 50, No. 1, pp. 322-333, 2009.
Maeda et al., Evaluation of 9-cis-Retinyl Acetate Therapy in Rpe65-/- Mice, Invest. Opthal. Vis. Sci., vol. 50, No. 9, pp. 4368-4378, 2009.
Maeda et al., Evaluation of the Role of the Retinal G Protein-coupled Receptor (RGR) in the Vertebrate Retina in Vivo, J. Neurochemistry, vol. 85, pp. 944-956, 2003.
Maeda et al., Improvement in Rod and Cone Function in Mouse Model of Fundus Albipunctatus After Pharmacologic Treatment with 9-cis-Retinal, IOVS, vol. 47, No. 10, pp. 4540-4546, 2006.
Maeda et al., Loss of Cone Photoreceptors Caused by Chromophore Depletion is Partially Prevented by the Artificial Chromophore Pro-drug, 9-cis-retinyl Acetate, Human Molecular Genetics, vol. 18, No. 12, pp. 2277-2287, 2009 (published on-line Apr. 1, 2009).
Maeda et al., QLT91001, a 9-cis-Retinal Analog, Is Well-Tolerated by Retinas of Mice with Impaired Visual Cycles, Invest. Ophthal. Vis. Sci., vol. 54, No. 1, pp. 455-466, 2013.
Maeda et al., Role of Photoreceptor-Specific Retinol Dehydrogenase in the Retinoid Cycle in Vivo, J. Bio. Chem., vol. 280, No. 19, pp. 18822-18832, 2005.
Maguire et al., Safety and Efficacy of Gene Transfer for Leber Congenital Amaurosis, Supplementary Appendix from N. Engl. J. Med., vol. 358, pp. 2240-2248, 2008.
Maguire et al., Safety and Efficacy of Gene Transfer for Leber's Congenital Amaurosis, N. Engl. J. Med., vol. 358, pp. 2240-2248, 2008.
Margaron et al., Evaluation of Intravitreal cis-Retinoid Replacement Therapy in a Canine Model of Leber's Congenital Amaurosis, Invest. Ophthalmol. Vis. Sci., vol. 50, E-Abstract 6280, 2009.
Marlhens et al., Autosomal Recessive Retinal Dystrophy Associated with Two Novel Mutations in the RPE65 Gene, Eur. J. Hum. Genet., vol. 6, No. 5, pp. 527-531, 1998.
Marlhens et al., Mutations in RPE65 Cause Leber's Congenital Amaurosis, Nature Genetics, vol. 17, pp. 139-141, 1997.
Marmor et al., Abipunctate Retinopathy With Cone Dysfunction and No Abnormality in the RDH5 or RLBP1 genes, Retina, vol. 23, No. 4, pp. 543-546, 2003.
Massoud et al., Plasma Vitamin A and Beta-Carotene in Retinitis Pigmentosa, Brit. J. Opthal., vol. 59, pp. 200-204, 1975.
Mata et al., Substrate Specificity of Retinyl Ester Hydrolase Activity in Retinal Pigment Epithelium, Journal of Lipid Research, vol. 39, pp. 604-612, 1998.
Matsukawa et al., Role of Purpurin as a Retinal-Binding Protein in Goldfish Retina During the Early State of Optic Nerve Regeneration: Its Riming Action on Neurite Outgrowth, J. Neurosci., vol. 24, No. 38, pp. 8346-8353, 2004.
Maugard et al., Enzymatic Synthesis of Derivatives of Vitamin A in Organic Media, J. Mol. Cat. B, vol. 8, pp. 275-280, 2000.
Maugard et al., Synthesis of Water-Soluble Retinol Derivatives by Enzymatic Method, Biotechnol. Prog., vol. 18, pp. 424-428, 2002.
Maxwell et al., Photodynamic Response in Rhodotorula Glutinis in the Absence of Added Sensitizers, Photochemistry and Photobiology, vol. 13, pp. 259-273, 1971.

Mayo Clinic, Retinal Detachment, 8 pgs, 2010, printed from http://www.mayoclinic.com/health/retinal-detachment/DS00254/METHOD=print&DSECTION=all.
McBee et al., Confronting Complexity: the Interlink of Phototransduction and Retinoid Metabolism in the Vertebrate Retina, Prog. Retin. Eye Res., vol. 20, pp. 469-529, 2001.
McBee et al., Isomerization of 11-cis-Retinoids to All-Trans-Retinoids in Vitro and in Vivo, J. Biol. Chem., vol. 276, No. 51, pp. 48483-48493, 2001.
MedlinePlus, Diabetic Retinopathy, 5 pages, 2011, printed from http://www.nim.nih.gov/medlineplus/ency/article/00212.htm.
Mendes et al., Pharmacological Manipulation of Rhodopsin Retinitis Pigmentosa, Advances in Experimental Medicine and Biology, Chapter 36, pp. 317-323, DOI 10.10071978-1-4419-1399-9_36, Springer Science+Business Media, LLC, 2010.
Mizukami et al., Photoisomerization Mechanism of the Rhodopsin Chromophore: Picosecond Photolysis of Pigment Containing 11-cis-locked Eight-Membered Ring Retinal, Proc. Natl. Acad. Sci. USA, vol. 90, pp. 4072-4076, May 1993.
Moise et al., Delivery of Retinoid-Based Therapies to Target Tissues, Biochemistry, vol. 46, No. 15, pp. 4449-4458, 2007.
Moiseyev et al., RPE65 is the Isomerohydrolase in the Retinoid Visual Cycle, Proc. Natl. Acad. Sci. USA, vol. 102, No. 35, pp. 12413-12418, 2005.
Morimura et al., Mutations in the RPE65 Gene in Patients with Autosomal Recessive Retinitis Pigmentosa or Leber Congenital Amaurosis, Proc. Natl. Acad. Sci. USA, vol. 95, No. 6, pp. 3088-3093, 1998.
Myhre et al., Water-Miscible, Emulsified and Solid Forms of Retinol Supplements are More Toxic Than Oil-Based Preparations, Am. J. Clin. Nutr., vol. 78, No. 6, pp. 1152-1159, 2003.
Nakamura et al., A High Association With Cone Dystrophy in Fundus albipunctatus Caused by Mutations of the RDH5 Gene, Invest. Opthalmol. Vis. Sci., vol. 41, No. 12, pp. 3925-3932, 2000.
Newton et al., Structure-Activity Relationships of Retinoids in Hamster Tracheal Organ Culture, Cancer Res., vol. 40, pp. 3413-3425, 1980.
Nishiguchi et al., A Novel Mutation (I143NT) in Guanylate Cyclase-Activating Protein 1 (GCAP1) Associated with Autosomal Dominant Cone Degeneration, Invest. Opthalmol. Vis. Sci., vol. 45, No. 11, pp. 3863-3870, 2004.
Noell, Suitability of Retinol, Retinal, and Retinyl Palmitate for the Regeneration of Bleached Rhodopsin in the Isolated Frog Retina, XP002486105, STN Database Accession No. 1985:164043 and Vision Research, vol. 24, No. 11, pp. 1615-1622, CODEN:VISRAM; ISSN:0042-6989, 1984 (Abstract only).
Noorwez et al., Pharmacological Chaperone-Mediated in Vivo Folding and Stabilization of the P23H-opsin Mutant Associated with Autosomal Dominant Retinitis Pigmentosa, J. Biol. Chem., vol. 278, No. 16, pp. 14442-14450, 2003.
Noorwez et al., Retinoids Assist the Cellular Folding of the Autosomal Dominant Retinitis Pigmentosa Opsin Mutant P23H, J. Biol. Chem., vol. 279, No. 16, pp. 16278-16284, 2004.
Norum and Blomhoff, McCollum Award Lecture, 1992: Vitamin A Absorption, Transport, Cellular Uptake, and Storage, Am. J. Clin. Nutr., vol. 56, pp. 735-744, 1992.
O'Bryne et al., Retinoid Absorption and Storage is Impaired in Mice Lacking Lecithin:Retinol Acyltransferase (LRAT), J. Biol. Chem., vol. 280, No. 42, pp. 35647-35657, Oct. 2005.
Ohgane et al., Retinobenzaldehydes as Proper-Trafficking Inducers of Folding-Defective P23H Rhodopsin Mutant Responsible for Retinitis Pigmentosa, Bioorg. Med. Chem., vol. 18, pp. 7022-7028, 2010.
Owsley et al., Delays in Rod-Mediated Dark Adaption in Early Age-Related Maculopathy, Ophthalmology, vol. 108, No. 7, pp. 1196-1202, 2001.
Owsley et al., Development of a Questionnaire to Assess Vision Problems under Low Luminance in Age-Related Maculopathy, Invest. Ophthalmol. Vis. Sci., vol. 47, No. 2, pp. 528-535, 2006.
Owsley et al., Effect of Short-Term, High-Dose Retinol on Dark Adaption in Aging and Early Age-Related Maculopathy, Invest. Ophthalmol. Vis. Sci., vol. 47, No. 4, pp. 1310-1318, 2006.

(56) References Cited

OTHER PUBLICATIONS

Paik et al., 9-cis-Retinoids: Biosynthesis of 9-cis-Retinoic Acid, Biochemistry, vol. 39, No. 27, pp. 8073-8084, 2000.
Palczewski, G Protein-Coupled Receptor Rhodopsin, Annual Rev. Biochem., vol. 75, pp. 743-767, 2006.
Pang et al., Retinal Degeneration 12 (rd12): A New, Spontaneously Arising Mouse Model for Human Leber Congenital Amaurosis (LCA), Molecular Vision, vol. 11, pp. 152-162, 2005.
Park et al., Toward a Clinical Protocol for Assessing Rod, Cone and Melanopsin Contributions to the Human Pupil Response, Invest. Ophthalmol. Vis Sci., vol. 52, No. 9, pp. 6624-6635, 2011.
Parry et al., Visual Pigment Reconstitution in Intact Goldfish Retina Using Synthetic Retinaldehyde Isomers, Vision Research, vol. 40, No. 17, pp. 2241-2247, 2000.
Pearlman et al., Visual Pigments of the Vitamin A-Deficient, Thyroidectomized Rat Following Vitamin A2 Administration, Vision Research, vol. 11, No. 3, pp. 177-187, 1971.
Perrault et al., Leber Congenital Amaurosis, Mol. Genet. Metab., vol. 68, pp. 200-208, 1999.
Perusek et al., Vitamin A Derivatives as Treatment Options for Retinal Degenerative Diseases, Nutrients, vol. 5, pp. 2646-2666, 2013.
Huttunen et al., Prodrugs—from Serendipity to Rational Design, Pharmacological Reviews, vol. 63, No. 3, pp. 750-771, 2011.
Illing et al., A Rhodopsin Mutant linked to Autosomal Dominant Retinitis Pigmentosa is Prone to Aggregate and Interacts with Ubiquitin Proteasome System., J. Biol. Chem., vol. 277, No. 37, pp. 34150-34160, 2002.
Imai et al., Probing for the Threshold Energy for Visual Transduction: Red-Shifted Visual Pigment Analogs from 3-Methoxy-3-Dehydroretinal and Related Compounds, Photochemistry and Photobiology, vol. 70, No. 1, pp. 111-115, 1999.
Imamoto et al., Structure Around C6—C7 Bond of the Chromophore in Bathorhodopsin: Low-Temperature Spectroscopy of 6s-cis-Locked Bicyclic Rhodopsin Analogs, Biochemistry, vol. 35, pp. 6257-6262, 1996.
Imanishi et al., Noninvasive Two-Photon Imaging Reveals Retinyl Ester Storage Structures in the Eye, The Journal of Cell Biology, vol. 164 No. 3, pp. 373-383, 2004.
International Search Report from related PCT patent Application No: PCT/US2004/007937 dated Dec. 3, 2004, application now published as International Publication No: WO2004/082622, published on Sep. 30, 2004.
International Search Report from related PCT patent Application No: PCT/US2005/021812 dated Dec. 28, 2005, application now published as International Publication No: WO2006/002097, published on Jan. 5, 2006.
International Search Report from related PCT patent Application No: PCT/US2009/000824 dated Nov. 5, 2009, application now published as International Publication No: WO2009/102418, published on Aug. 20, 2009.
International Search Report and Written Opinion dated Apr. 15, 2013 for PCT/CA2013/050155.
Jackson et al., Aging and Dark Adaptation, J. Vision Research, vol. 39, pp. 3975-3982, 1999.
Jackson et al., Aging and Scotopic Sensitivity, Vis. Res., vol. 38, pp. 3655-3662, 1998.
Jackson et al., Photoreceptor Degeneration and Dysfunction in Aging and Age-Related Maculopathy, Aging Res. Rev., vol. 1, No. 3, pp. 381-396, 2002.
Jacobson et al., Defining the Residual Vision in Leber Congenital Amaurosis Caused by RPE65 Mutations, Investigative Ophthalmology & Visual Science, vol. 50, No. 5, pp. 2368-2375, May 2009.
Jacobson et al., Identifying Photoreceptors in Blind Eyes Caused by RPE65 Mutations: Prerequisite for Human Gene Therapy Success, PNAS USA, vol. 102, No. 17, pp. 6177-6182, 2005.
Jacobson et al., Night Blindness in Sorsbys Fundus Dystrophy Reversed by Vitamin A, Nat. Genet., vol. 11, pp. 27-32, 1995.
Jacobson et al., Phenotypic Marker for Early Disease Detection in Dominant Late-Onset Retinal Degeneration, IOVS, vol. 42, No. 8, pp. 1882-1890, 2001.
Jacobson et al., Retinal Degenerations with Truncation Mutations in the Cone-Rod Homeobox (CRX) Gene, Invest. Opthalmol. Vis. Sci., vol. 39, No. 12, pp. 2417-2426, 1988.
Jang et al., Characterization of Dehydrogenase Activity Responsible for Oxidation of 11-cis-Retinol in the Reitnal Pigment Epithelium of Mice with a Disrupted RDH5 Gene. A Model for the Human Heredity Disease Fundus Albunctatus, J. Biol. Chem., vol. 276, No. 35, pp. 32456-32465, 2001.
Jang et al., Mechanism of Rhodopsin Activation as Examined with Ring-constrained Retinal Analogs and Crystal Structure of the Ground State Protein, The Journal of Biological Chemistry, vol. 276, No. 28, pp. 26148-26153, Jul. 13, 2001.
Jin et al, Noncovalent Occupancy of the Retinal-Binding Pocket of Opsin Diminishes Bleaching Adaption of Retinal Cones, Neuron, No. 11, pp. 513-522, 1993.
Jin et al., RPE65 is the Retinoid Isomerase in Bovine Retinal Pigment Epithelium, Cell, vol. 122, pp. 449-459, 2005.
Karnaukhova et al., Bioactivity of Visual Pigments with Stericalty Modified Retinal Analogs, Bioorganic Chemistry, vol. 27, pp. 372-382, 1999.
Kefalov el al., Role of Noncovalent Binding of 11-cis-retinal of Opsin in Dark Adaption of Rod and Cone Photoreceptors, Neuron, vol. 29, pp. 749-755, 2001.
Kemp et al., Visual Function and Rhodopsin Levels in Humans with Vitamin A Deficiency, Exp. Eye Res., vol. 46, pp. 195-197, 1988.
Kirillova et al., Cyclopentene and Cyclohexene Retinal Analogues React Differently with Bacteriorhodopsin, Chemical Abstracts, vol. 120, pp. 557, 1994 (abstract No. 120:187138, abstract only).
Klein et al., Psychophysical Assessment of Low Visual Function in Patients with Retinal Degenerative Diseases (RODs) With the Diagnosys Full-Field Stimulus Threshold (D-FST), Doc. Ophthalmol., vol. 119, pp. 217-224, 2009.
Koenekoop et al., Oral Synthetic cis-Retinoid Therapy in Subjucts with Leber Congenital Amauarosis (LCA) due to Lecithin-Retinol Acyltransferase (LRAT) of Retinal Pigment Epithelial 65 Protein (RPE65) Mutations: Preliminary Results of a Phase 1b Open-Label Trial, Poster presented at Annual Meeting of the Association for Research in Vision and Opthamology (ARVO), May 2011, http://qltinc.com/development/products/documents/QLT091001-LCA-ARVO_2011_poster.pdf See entire document.
Koenekoop et al., Oral 9-cis Retinoid for Childhood Blindess due to Leber Congenital Amaurosis caused by RPE65 or LRAT mutations: an Open-Lable Phase 1b Trial, Lancet, 8 pages, published online http://dx.doi.org/10.1016/S0140-6736(14)60153-7, published Jul. 14, 2014.
Koenekoop, Oral Synthetic Cis-Retinoid Therapy in Subjects with Leber Congenital Amaurosis (LCA) due to Lecithin:Retinol Acyltransferase (LRAT) or Retinal Pigment Epithelial 65 Protein (RPE65) Mutations: Preliminary Results of a Phase 1b Open Label Trial, Invest. Ophthalmol. Vis. Sci., vol. 52, E-Abstract 3323, 2011.
Koenekoop, Update on the Safety and Efficacy of a Novel Oral Retinoid for the Treatment of Childhood Vision Loss Due to RPE65 or LRAT Mutations, powerpoint presentation.
Koutalos, Regeneration of Bovine and Octopus Opsins in Situ with Natural and Artificial Retinals, Biochemistry, vol. 28, pp. 2732-2739, 1989.
Kozlov et al., Oxidation of Vitamin A Acetate in Soybean Oil, Khimio-Farmatsevti-cheskii-Zhurnal, vol. 10, pp. 24-29, 1971 (english translation).
Kubo et al., Effect of Vitamin A Palmitate on Vitamin A-Deficient Rabbits, XP002475885, STN database accession No. 2000:172779 & Nippon Ganka Gakkai Zasshi, vol. 103, No. 10, pp. 729-733, CODEN:NGZAA6: ISSN: 0029-0203, 1999, Abstract only.
Kuksa et al., Biochemical and Physiological Properties of Rhodopsin Regenerated with 11-cis-6-Ring- and 7-Ring-Retinals, The Journal of Biological Chemistry, vol. 277, No. 44, pp. 42315-42324, Nov. 1, 2002.
Kuksa et al., Retinoid Cycle in the Vertebrate Retina: Experimental Approaches and Mechanisms of Isomerization, Vision Research, vol. 43, pp. 2959-2981, 2003.

(56) References Cited

OTHER PUBLICATIONS

Kupfer et al., Information for doctors who follow patients with retinitis pigmentosa, National Eye Institute, 1993, printed from http://www.nei.nih.gov/news/clinicalalerts/alert-rp.asp on Jan. 15, 2009, 2 pages.
Kuse et al., Change in Retinal Rod Function in Age-Related Macular Degeneration, Japanese Review of Clinical Ophthalmology, vol. 10, No. 100, pp. 59, 2006 (english abstract only).
Lamb and Pugh, Phototransduction, Dark Adaptation, and Rhodopsin Regeneration, IOVS, vol. 47, No. 12, pp. 5138-5152, 2006.
Lamb et al., Dark Adaptation and the Retinoid Cycle of Vision, J. Prog. Retin Eye Res., vol. 23, pp. 307-380, 2004.
Lang, Ocular Drug Delivery Conventional Ocular Formulations, Adv. Drug Del. Rev., vol. 16, No. 1, pp. 39-43, 1995.
Lawson et al., Retinal Analog Restoration of Photophobic Responses in a Blind Chlamydomonas-reinhardtii Mutant Evidence for an Archaebacterial Like Chromophore in a Eukarayotic Rhodopsin, Biophysical Journal, vol. 60, No. 6, pp. 1490-1498, 1991.
Lewin et al., Synthesis and Characterization of Trans-, 13-cis, and 11-cis, 13-cis-12- (Hydroxymethyl) Retinols, J. Org. Chem., vol. 49, pp. 649-652, 1984.
Lewis et al., Steric Barrier to Bathorhodopsin Decay in 5-Demethyl and Mesityl Analogues of Rhodopsin, J. Am. Chem. Soc. vol. 123, pp. 10024-10029, 2001.
Li et al., Delivery of 9-cis Retinal to Photoreceptors from Bovine Serum Albumin, Photochem. Photobiol., vol. 69, No. 4, pp. 500-504, 1999.
Li et al. Effect of Vitamin A Supplementation of Rhodopsin Mutants Threonine-17->Methionine and proline-347-> Serine in Transgenic Mice and in Cell Cultures, Proc. Natl. Acad. Sci. USA, vol. 95, pp. 11933-11938, 1998.
Lin et al., Vibrational Assignment of Torsional Normal Modes of Rhodopsin: Probing Excited-State Isomerization Dynamics Along the Reactive C11dC12 Torsion Coordinate, J. Phys. Chem. B, vol. 102, pp. 2787-2806, 1998.
Littink et al., A Homozygous Frameshift Mutation in LRAT Causes Retinitis Punctata Albescens, Ophthalmology, vol. 119, pp. 1899-1906, 2012.
Liu et al., The Nature of Restrictions in the Binding Site of Rhodopsin. A Model Study, J. Am. Chem. Soc., vol. 106, No. 26, pp. 8298-8300, 1984.
Lorenz et al., A Comprehensive Clinical and Biochemical Functional Study of a Novel RPE65 Hypomorphic Mutation, Invest. Ophthalmol. Vis. Sci., vol. 49, pp. 5235-5242, 2008.
Lorenz et al., Early-onset Severe Rod-Cone Dystrophy in Young Children with RPE65 Mutations, Invest. Ophthalmol. Vis. Sci., vol. 41, pp. 2735-2742, 2000.

\* cited by examiner

THERAPEUTIC REGIMENS AND METHODS FOR IMPROVING VISUAL FUNCTION IN VISUAL DISORDERS ASSOCIATED WITH AN ENDOGENOUS RETINOID DEFICIENCY

RELATED APPLICATIONS

This application is a continuation of U.S. application Ser. No. 15/096,048, filed Apr. 11, 2016, which is a continuation of U.S. application Ser. No. 14/382,235, filed Aug. 29, 2014, which is a national stage application under 35 U.S.C. § 371 of International Application No. PCT/CA2013/050155, filed Mar. 1, 2013, which claims the benefit of priority to U.S. provisional patent application No. 61/605,729, filed Mar. 1, 2012; U.S. provisional patent application No. 61/642,212, filed May 3, 2012; and U.S. provisional patent application No. 61/644,360, filed May 8, 2012; the disclosures of which are incorporated herein by reference in their entirety.

FIELD OF THE DISCLOSURE

This disclosure is directed to therapeutic regimens and methods for improving visual function in a subject with a visual disorder associated with an endogenous retinoid deficiency comprising administering a synthetic retinal derivative to the subject.

BACKGROUND

Inherited retinal diseases (IRD) caused by gene mutations that disrupt or interfere with the production, conversion and/or regeneration of 11-cis-retinal result in severe visual impairment and childhood blindness. 11-cis-Retinal is an endogenous retinoid produced in and by the retinal pigment epithelium (RPE) from the isomerization and oxidation of the all-trans-retinol (Vitamin A derived from the diet). 11-cis-Retinal functions as a chromophore and convalently binds to the protein opsin to form isorhodopsin. Vision is initiated when a light photon is captured by 11-cis-retinal, resulting in the isomerization to all-trans-retinal and disassociation from opsin. Vision is sustained by the cycling of all-trans-retinal back into 11-cis-retinal, which occurs by a complex series of biochemical reactions involving multiple enzymes and proteins in the retinoid or visual cycle.

Endogenous retinoid deficiencies, such as those caused by mutations in the genes encoding the enzymes and proteins utilized in the visual cycle, impair the synthesis of 11-cis-retinal, the result of which leads to visual disorders due to the shortage or depletion of 11-cis-retinal.

For example, Retinitis Pigmentosa (RP) is an inherited retinal disease that features degeneration of rod and cone photoreceptor cells (Hartong, D. T. et al., Lancet, 368, 1795-1809 (2006)). There are a variety of forms of RP all of which show various limitations of visual performance over time and the course and progression of the disease show considerable variability between individuals. RP is typically characterized by initial symptoms of night blindness, with onset in adolescence or early adulthood, loss of peripheral vision and, as the disease progresses, loss of central vision that can lead to blindness or severe visual impairment. The age-at-onset of symptoms is highly variable and ranges from childhood to mid-adulthood. RP Disease Classification can be by made by age of onset, for example, congenital RP (sometimes referred to as LCA), juvenile onset RP, teenage onset RP, adult onset RP, and late onset RP. ERG responses are an early indicator of loss of rod and cone function in RP and diminution of ERG responses can be evident within the first few years of life, even though symptoms appear much later.

Typical RP presents as primary degeneration of rods, with secondary degeneration of cones, and is consequently described as a rod-cone dystrophy, with rods being more affected than cones. This sequence of photoreceptor involvement explains why some RP subjects initially present with night blindness, and only in later life become visually impaired in all light conditions. Alternatively, in about 10-20% of subjects with RP exhibit cone-rod dystrophy.

RP can be caused by defects in many different genes and their related disease pathways. At present, more than 200 causative RP mutations have been detected in more than 100 different genes.

RP genotypes are heterogeneous, and RP subjects with the same mutation can exhibit different phenotypes. RP may be classified by inheritance type, for example, autosomal dominant (ad) RP, autosomal recessive (ar) RP, X-linked (XL) or sex-linked recessive RP, sporadic RP (simplex RP; most are recessive), or Digenic RP. RP is currently estimated to affect at least 300,000 individuals worldwide, of which approximately 20%-30% are autosomal recessive (arRP).

In recent years, mutations in the LRAT and RPE65 genes have been discovered in RP subjects with arRP or adRP. These specific mutations, as well as mutations in ABCA4 and RDH12 are linked to defects in retinoid metabolism of the visual cycle and may result in photoreceptor degeneration. Endogenous retinoid deficiencies, such as those caused by mutations in the genes encoding the enzymes and proteins utilized in the visual cycle impair the synthesis of 11-cis-retinal, the result of which leads to visual disorders due to the shortage or depletion of 11-cis-retinal.

The protein encoded by the RPE65 gene has a biochemical association with retinol binding protein and 11-cis-retinol dehydrogenase and is essential for 11-cis-retinal production (Gollapalli, D. R. et al., Biochemistry. 42(19): 5809-5818 (2003) and Redmond, T. M. et al., Nat Genet. 20(4):344-351 (1998)). 11-Cis-retinal is an endogenous retinoid produced in and by the retinal pigment epithelium (RPE) from the isomerization and oxidation of the all-trans-retinol (Vitamin A derived from the diet). 11-Cis-retinal functions as a chromophore and covalently binds to the protein opsin to form rhodopsin. Vision is initiated when a light photon is captured by 11-cis-retinal, resulting in the isomerization to all-trans-retinal and disassociation from opsin. Vision is sustained by the cycling of all-trans-retinal back into 11-cis-retinal, which occurs by a complex series of biochemical reactions involving multiple enzymes and proteins in the retinoid or visual cycle. Preclinical and clinical information show that loss of the function of the RPE65 protein blocks retinoid processing after esterification of vitamin A to membrane lipids and results in loss of vision.

RPE65 mutations are predominantly associated with early-onset severe retinal dystrophy, with rod-cone degeneration, nystagmus and severe visual loss within the first few years of life. The severity of the disease resulting from mutations in RPE65 appears to be largely independent of the mutation types present in the RP subjects. Many RPE65 subjects share a common phenotype characterized by poor but useful visual function in early life (measurable cone ERGs) that declines dramatically throughout the school age years. In addition, a number of these RP subjects retain residual islands of peripheral vision, although considerably compromised, into the third decade of life.

Progressive visual field (VF) loss is one of the hallmarks of RP and is commonly used as a means to monitor the progression of the disease (Grover et al., Ophthalmology, 105: 1069-1075 (1998)). It has been observed that most RP subjects are legally blind by age 40 because of severely constricted visual fields due to loss of rod function exceeding reduction of cone sensitivity.

Visual acuity (VA) impairment may also be noted during the course of the RP although RP subjects with early-onset RP have been reported to have more stable VA than other RP types and the level of VA impairment can vary widely amongst RP subjects. For example, it has been reported for some RP patients with advanced RP with a small island of remaining central VF, that VA may remain normal. In other RP patients, VA decreases can be more pronounced.

By way of another example, Leber congenital amaurosis (LCA), a cause of inherited childhood blindness that affects children from birth or shortly thereafter, is associated with an inherited gene mutation, for example, in the RPE65 gene which encodes the protein retinal pigment epithelial protein 65 (RPE65) and/or an inherited gene mutation in the LRAT gene which encodes the enzyme lecithin:retinol acetyltransferase (LRAT). Patients with LCA lack the ability to generate 11-cis-retinal in adequate quantities and therefore suffer from severe vision loss at birth, nystagmus, poor pupillary responses and severely diminished electroretinograms (ERGs). Significant clinical variability in the severity of LCA presentation exists, including intrafamilial variability in severity. LCA exhibits clinical and genetic heterogenetity in terms of the natural history of vision loss, behavior in low light conditions, and genetic defects responsible for the phenotype.

Retinitis Punctata Albesciens (RPA) is another form of RP that exhibits a shortage of 11-cis-retinal in the rods. Recently, homozygous frameshift mutations in LRAT were identified as a cause of RPA in certain subjects and it has been reported that LRAT is the fourth gene involved in the visual cycle that may cause a white-dot retinopathy (Littink et al., Ophthalmology, 119: 1899-906 (2012)).

Congenital Stationary Night Blindness (CSNB) and Fundus Albipunctatus are a group of diseases that are manifested as night blindness, but there is not a progressive loss of vision as in RP. Some forms of CSNB are due to a delay in the recycling of 11-cis-retinal. Fundus Albipunctatus until recently was thought to be a special case of CSNB where the retinal appearance is abnormal with hundreds of small white dots appearing in the retina. It has been shown recently that this is also a progressive disease although much slower than RP. It is caused by gene defects that lead to a delay in the cycling of 11-cis-retinal, including heterozygous mutations in RPE65 (Schatz et al., Ophthalmology, 118:888-94 (2011)).

The use of synthetic retinal derivatives and compositions thereof in methods of restoring or stabilizing photoreceptor function in a vertebrate visual system is disclosed in International Published Patent Application Nos. WO 2004/082622, WO 2006/002097, WO 2009/102418, and WO 2011/034551, WO 2011/132084, and Published U.S. Application Nos. 2004/0242704, 2008/0221208 (issued as U.S. Pat. No. 7,951,841), and 2010/0035986 (issued as U.S. Pat. No. 8,324,270). A study to evaluate the effects of daily and intermittent dosing of 9-cis-retinyl acetate, a synthetic retinal derivative, in aging mice is disclosed in Maeda, T. et al., Investigative Ophthalmology & Visual Science (2009), Vol. 50, No. 9, pp. 4368-4378).

Animal models have shown that synthetic retinoids which are highly-light sensitive compounds are photoisomerized or "bleached" by light from the retina within just a few hours unless the eyes are covered. These studies were conducted with the animals kept in the dark for specified periods during treatment with synthetic retinoids until the evaluation period in order to minimize photoisomerization/bleaching of the synthetic retinoid, defeating the entire purpose of the treatment. Batten M L et al. "Pharmacological and rAAV Gene Therapy Rescue of Viscual Functions in a Blind Mouse Model of Leber Congenital Amaurosis" PLo-S Medicine vol. 2, p. 333 (2005); Margaron, P., Castaner, L., and Narfstrom, K. "Evaluation of Intravitreal cis-Retinoid Replacement Therapy in a Canine Model Of Leber's Congenital Amaurosis" Invest Ophthalmol Vis Sci 2009; 50:E-Abstract 6280; Gearhart P M, Gearhart C, Thompson D A, Petersen-Jones S M. "Improvement of visual performance with intravitreal administration of 9-cis-retinal in Rpe65-mutant dogs" Arch Ophthalmol 2010; 128(11): 1442-8.

Frequent administration of any retinoid to compensate for the bleaching effect implicates the well-known toxicity of the retinoid class of the compounds. See, Teelmann, K "Retinoids: Toxicity and Teratogenicity to Date," Pharmac. Ther., Vol. 40, pp 29-43 (1989); Gerber, L E et al "Changes in Lipid Metabolism During Retinoid Administration" J. Amer. Acad. Derm., Vol. 6, pp 664-74 (1982); Allen L H "Estimating the Potential for Vit A Toxicity in Women and Young Children" J. Nutr., Vol. 132, pp. 2907-19 (2002); Silverman, A K "Hypervitaminosis A Syndrome: A Paradigm of Retinoid Side Effects", J. Am. Acad. Derm., Vol. 16, pp 1027-39 (1987); Zech L A et al. "Changes in Plasma Cholesterol and Triglyceride Levels After Treatment with Oral Isotretinoin" Arch. Dermatol., Vol. 119, pp 987-93 (1983). Toxicity caused by chronic administration of retinoids can cause changes in lipid metabolism, damage to the liver, nausea, vomiting, blurred vision, damage to bones, interference with bone development and several other serious undesirable effects.

In the context of improving visual function in a subject with an endogenous retinoid deficiency, such as RP or LCA, which is a chronic condition requiring lifetime treatments, these toxic effects can be very important. These side effects are of particular concern in young subjects, whose susceptibility to side effects related to their physical development is well documented.

This combination of a need for repeated administration in response to bleaching, and the undesirable serious side effects of repeated administration, poses a problem for the use of synthetic retinoids to improve visual function in a subject having an endogenous retinoid deficiency, such as RP or LCA. A recent study evaluated the usefulness of retinoids as a treatment for these disorders and concluded that retinoids and similar compounds were not good therapeutic candidates. See, Fan J. et al. "Light Prevents Exogenous 11-cis Retinal from Maintaining Cone Photoreceptors in Chromophore-deficient Mice", Invest. Ophthalmol. Vis Sci. Jan. 12, 2011, 10-6437.

SUMMARY OF INVENTION

The present disclosure provides certain dosing regimens of synthetic retinal derivatives that can provide replacement for endogenously produced 11-cis-retinal, thereby producing meaningful improvement of vision in a subject having an endogenous retinoid deficiency throughout a resting interval of less than one month, such as from 7 to 28 days, while at the same time exhibiting an acceptable safety profile throughout repeat treatment cycles of dosing and resting. In certain embodiments, the acceptable safety profile may be achieved by minimizing and/or reducing the severity of the toxic side effects associated with frequent and subsequent administration of synthetic retinal derivatives through subsequent dosing cycles. In certain embodiments, the endogenous retinoid deficiency is caused by mutations in the genes encoding the enzymes and proteins utilized in the visual cycle, such as in retinitis pigmentosa (RP) or Leber congenital amaurosis (LCA) subjects. Accordingly, therapeutic regimens and methods for improving visual function in a subject with RP, LCA, or another visual disorder associated with an endogenous 11-cis-retinal deficiency comprising administering a synthetic retinal derivative to the subject, are provided.

In certain embodiments, the present disclosure provides a method of improving visual function in a subject having a deficiency in endogenously produced 11-cis-retinal comprising a) administering a first therapeutic dose of a synthetic retinal derivative to a subject in need thereof; b) providing a resting period of less than one month, such as from about 7 to about 28 days; and c) administering a second therapeutic dose of the 9- or 11-cis-retinyl ester to said subject following the end of the resting period.

In certain embodiments, the present disclosure provides a method of improving visual function in a subject comprises: a) administering a first therapeutic dose of a 9- or 11-cis-retinyl ester to a subject in need thereof; b) providing a resting period of less than one month, such as from about 7 to about 28 days; and c) administering a second therapeutic dose of the 9- or 11-cis-retinyl ester to said subject following the end of the resting period.

In certain embodiments, the subject is deficient in endogenously produced 11-cis-retinal. In some embodiments, the 9- or 11-cis-retinyl ester provides replacement of endogenously produced 11-cis-retinal.

In some embodiments, the subject has a LRAT gene mutation. In other embodiments, the subject has a RPE65 gene mutation.

In certain embodiments, the subject has moderate to severe RP. In other embodiments, the subject has mild RP. In some embodiments, the subject has early onset or juvenile RP. In some embodiments, the subject has congenital RP. In some embodiments, the subject has juvenile onset RP. In other embodiments, the subject has teenage onset RP. In other embodiments, the subject has adult onset RP, or late onset RP. In certain embodiments, the subject has autosomal recessive RP. In some embodiments, the subject has autosomal dominant RP.

In certain embodiments, the subject has LCA.

In some embodiments, the method of improving visual function in a subject, including a subject with RP, further comprises repeating the steps of b) and c) one or more times.

In certain embodiments, the first therapeutic dose is administered as a divided dose over a period of from 2 to 7 days. In some embodiments, the first therapeutic dose is administered as a divided dose over a period of 7 days. In other embodiments, the first therapeutic dose is administered as a divided dose over a period of 5 days.

In some embodiments, the resting period is from about 7 days to about 21 days. In some embodiments, the resting period is about 21 days. In other embodiments, the resting period is about 14 days. In other embodiments, the resting period is about 7 days.

In certain embodiments, the first therapeutic dose is from about 280 mg/m$^2$ to about 420 mg/m$^2$. In some embodiments, the first therapeutic dose is about 280 mg/m$^2$. In some embodiments, the first therapeutic dose is about 420 mg/m$^2$.

In certain embodiments, the therapeutic doses are administered orally.

In certain embodiments, the first therapeutic dose is about 5 mg/m$^2$ per day, or about 10 mg/m$^2$ per day, or about 20 mg/m$^2$ per day, or about 40 mg/m$^2$ per day. In other embodiments, the first therapeutic dose is about 60 mg/m$^2$ per day.

In certain embodiments, the second therapeutic dose is administered for substantially the same period and in substantially the same amount as the first therapeutic dose.

In certain embodiments, the retinyl ester is a 9-cis-retinyl ester. In some embodiments, the retinyl ester is 9-cis-retinyl acetate. In some embodiments, the retinyl ester is 11-cis-retinyl acetate.

In certain embodiments, improving visual function comprises increasing visual field in an eye by at least 20% from baseline as measured by Goldmann Visual Field (GVF) analysis. In other embodiments, improving visual function comprises increasing visual acuity in an eye by greater than or equal to 5 letters from baseline as measured using an Early Treatment Diabetic Retinopathy Study (ETDRS) eye chart. In other embodiments, improving visual function comprises a clinically significant increase in retinal sensitivity from baseline.

The present disclosure also provides a method of improving visual function in a subject with an endogenous retinoid deficiency, such as RP, comprising: a) administering a first therapeutic dose of a 9-cis-retinyl acetate, wherein the first therapeutic dose is administered at about 40 mg/m$^2$ per day to about 60 mg/m$^2$ per day over a period of 7 days to a subject in need thereof; b) providing a resting period from about 7 days to about 21 days; and c) administering a second therapeutic dose of a 9-cis-retinyl acetate following the end of the resting period to a subject in need thereof.

In certain embodiments, the subject is deficient in endogenously produced 11-cis-retinal. In certain embodiments, the 9-cis-retinyl acetate provides replacement of endogenously produced 11-cis-retinal.

In certain embodiments, the subject has a LRAT gene mutation. In some embodiments, the subject has a RPE65 gene mutation.

In certain embodiments, the subject has moderate to severe RP. In other embodiments, the subject has mild RP. In some embodiments, the subject has early onset or juvenile RP.

In some embodiments, the method of improving visual function in a subject with RP further comprises repeating the steps of b) and c) one or more times.

In some embodiments, the improving visual function comprises increasing visual field in an eye by at least 20% from baseline as measured by Goldmann Visual Field (GVF) analysis, or increasing visual acuity in an eye by greater than or equal to 5 letters from baseline as measured using an Early Treatment Diabetic Retinopathy Study (ETDRS) eye chart, or both.

In some embodiments, the second therapeutic dose is administered for substantially the same period and in substantially the same amount as the first therapeutic dose.

In some embodiments, the therapeutic doses are administered orally.

In certain embodiments, the subject is a human subject.

The present disclosure also provides a method of improving visual function of a subject with an endogenous retinoid deficiency, such as RP, comprising administering at least a first and second therapeutic dose of 9- or 11-cis-retinyl ester to a subject in need thereof wherein a resting time period between the first dose and the second does is less than one month, such as from about 7 to about 28 days, and wherein improving visual function comprises increasing visual field in an eye by at least 20% from baseline as measured by Goldmann Visual Field (GVF) analysis, increasing visual acuity in an eye by greater than or equal to 5 letters from baseline as measured using an Early Treatment Diabetic Retinopathy Study (ETDRS) eye chart, or both.

In certain embodiments, the 9- or 11-cis-retinyl ester provides replacement of endogenously produced 11-cis-retinal.

In some embodiments, the subject is deficient in endogenously produced 11-cis-retinal. In certain embodiments, the subject has a LRAT gene mutation. In other embodiments, the subject has a RPE65 gene mutation.

In some embodiments, the subject has moderate to severe RP. In some embodiments, the subject has mild RP. In some embodiments, the subject has early onset or juvenile RP.

In certain embodiments, the subject has LCA.

In certain embodiments, the first therapeutic dose is administered as a divided dose over a period of from 2 to 7 days. In some embodiments, the first therapeutic dose is administered as a divided dose over a period of 7 days. In some embodiments, the first therapeutic dose is administered as a divided dose over a period of 5 days. In some embodiments, the first therapeutic dose is administered as a divided dose over a period of 6 days, or 4 days or 3 days or two days.

In certain embodiments, the resting period, during which no therapeutic dose is administered, is from about 2 days to about 21 days, from about 2 days to about 25 days, or from about 2 days to about 28 days. In certain such embodiments, the resting period, during which no therapeutic dose is administered, is from about 7 days to about 21 days, from about 7 days to about 25 days, or from about 7 days to about 28 days. In some embodiments, the resting period is from about 7 days to about 21 days. In some embodiments, the resting period is about 21 days. In other embodiments, the resting period is about 14 days. In other embodiments, the resting period is about 7 days.

In certain embodiments, the first therapeutic dose is from about 280 mg/m$^2$ to about 420 mg/m$^2$ total combined dose. In some embodiments, the first therapeutic dose is about 280 mg/m$^2$ total combined dose. In some embodiments, the first therapeutic dose is about 420 mg/m$^2$ total combined dose In some embodiments, the therapeutic dose is administered orally.

In certain embodiments, the first therapeutic dose is about 10 mg/m$^2$ per day. In certain embodiments, the first therapeutic dose is about 20 mg/m$^2$ per day. In certain embodiments, the first therapeutic dose is about 40 mg/m$^2$ per day. In other embodiments, the first therapeutic dose is about 60 mg/m$^2$ per day.

In some embodiments, the second therapeutic dose is administered for substantially the same period and in substantially the same amount as the first therapeutic dose.

In certain embodiments, the retinyl ester is a 9-cis-retinyl ester. In some embodiments, the retinyl ester is 9-cis-retinyl acetate. In some embodiments, the retinyl ester is 11-cis-retinyl acetate.

The present disclosure also provides a kit for improving visual function in a subject with an endogenous retinoid deficiency, such as RP, the kit comprising: a) at least a first therapeutic dose of a 9- or 11-cis-retinyl ester; and, b) instructions for use that provides a resting period between the first therapeutic dose and a second dose, wherein the resting period is less than a month, such as from about 7 to about 28 days.

In some embodiments, the 9- or 11-cis-retinyl ester provides replacement of endogenously produced 11-cis-retinal.

In certain embodiments, the subject is deficient in endogenously produced 11-cis-retinal. In some embodiments, the subject has a LRAT gene mutation. In other embodiments, the subject has a RPE65 gene mutation.

In some embodiments, the subject has moderate to severe RP. In other embodiments, the subject has mild RP. In some embodiments, the subject has early onset or juvenile RP.

In certain embodiments, the instructions direct that the first dose is administered in a divided dose over a period of from 2 to 7 days, or over a period of from 2 to 5 days. In some embodiments, the instructions direct that the first dose is administered in a divided dose over a period of 7 days. In some embodiments, the instructions direct that the resting period is from about 2 day to about 21 days. In some embodiments, the instructions direct that the resting period is from about 7 days to about 21 days. In some embodiments, the instructions direct that the resting period is about 21 days. In some embodiments, the instructions direct that the resting period is about 14 days. In some embodiments, the instructions direct that the resting period is about 7 days. In some embodiments, the instructions direct the resting period is about 23 days, 25 days, or 28 days. In some embodiments, the instructions direct that the total resting period plus the dosing period combine to add up to 28 days, or 30 days, for each treatment period in the dosing regimen.

In certain embodiments, the first therapeutic dose is from about 280 mg/m$^2$ to about 420 mg/m$^2$. In some embodiments, the first therapeutic dose is about 280 mg/m$^2$. In some embodiments, the first therapeutic dose is about 420 mg/m$^2$.

In certain embodiments, the therapeutic dose is administered orally.

In certain embodiments, the instructions direct that the first therapeutic dose is about 10 mg/m$^2$ per day. In certain embodiments, the instructions direct that the first therapeutic dose is about 20 mg/m$^2$ per day. In certain embodiments, the instructions direct that the first therapeutic dose is about 40 mg/m$^2$ per day. In certain embodiments, the instructions direct that the first therapeutic dose is about 60 mg/m$^2$ per day.

In certain embodiments, the second therapeutic dose is administered for substantially the same period and in substantially the same amount as the first therapeutic dose.

In certain embodiments, the retinyl ester is 9-cis-retinyl acetate. In other embodiments, the retinyl ester is 11-cis-retinyl acetate.

In certain embodiments, improving visual function comprises increasing visual field in an eye by at least 20% from baseline as measured by Goldmann Visual Field (GVF) analysis. In some embodiments, improving visual function comprises increasing visual acuity in an eye by greater than or equal to 5 letters from baseline as measured using an Early Treatment Diabetic Retinopathy Study (ETDRS) eye chart. In some embodiments, improving visual function comprises a clinically significant increase in retinal sensitivity from baseline.

The present disclosure also provides a dosing regimen for improving visual function of a subject with RP, wherein the dosing regimen comprises at least, a first therapeutic dose, a second therapeutic dose and a resting period between the first therapeutic dose and the second therapeutic dose, the regimen comprising: a) administering a first dose of a 9- or 11-cis-retinyl ester over a period of about 2 to about 7 days to a subject in need thereof b) providing a resting period of less than one month, such as from about 7 to about 28 days, between the first therapeutic dose and the second therapeutic dose; and c) administering the second therapeutic dose of a 9- or 11-cis-retinyl ester following the end of the resting period to the subject in need thereof.

In certain embodiments, the 9- or 11-cis-retinyl ester provides replacement of endogenously produced 11-cis-retinal.

In certain embodiments, the subject is deficient in endogenously produced 11-cis-retinal. In certain embodiments, the subject has a LRAT gene mutation. In other embodiments, the subject has a RPE65 gene mutation.

In certain embodiments, the subject has moderate to severe RP. In some embodiments, the subject has mild RP. In some embodiments, the subject has early onset or juvenile RP.

In certain embodiments, the dosing regimen further comprises repeating the steps of b) and c) one or more times.

In some embodiments, the first dose is administered in a divided dose over a period of 7 days.

In some embodiments, the resting period is from about 2 days to about 28 days, such as from about 7 days to about 28 days. In some embodiments, the resting period is from about 7 days to about 21 days. In some embodiments, resting period is about 21 days. In some embodiments, the resting period is about 14 days. In some embodiments, the resting period is about 7 days.

In certain embodiments, the first therapeutic dose is from about 280 mg/m$^2$ to about 420 mg/m$^2$. In some embodiments, the first therapeutic dose is about 280 mg/m$^2$.

In certain embodiments, the therapeutic doses are administered orally.

In certain embodiments, the first therapeutic dose is about 10 mg/m$^2$ per day. In certain embodiments, the first therapeutic dose is about 20 mg/m$^2$ per day. In certain embodiments, the first therapeutic dose is about 40 mg/m$^2$ per day. In other embodiments, the first therapeutic dose is about 60 mg/m$^2$ per day.

In certain embodiments, the second therapeutic dose is administered for substantially the same period and in substantially the same amount as the first therapeutic dose.

In certain embodiments, the retinyl ester is 9-cis-retinyl acetate. In other embodiments, the retinyl ester is 11-cis-retinyl acetate.

In certain embodiments, improving visual function comprises increasing visual field in an eye by at least 20% from baseline as measured by Goldmann Visual Field (GVF) analysis. In some embodiments, improving visual function comprises increasing visual acuity in an eye by greater than or equal to 5 letters from baseline as measured using an Early Treatment Diabetic Retinopathy Study (ETDRS) eye chart. In some embodiments, improving visual function comprises a clinically significant increase in retinal sensitivity from baseline.

The present disclosure also provides a dosing regimen for improving visual function of a subject with RP, wherein the dosing regimen comprises at least, a first therapeutic dose, a second therapeutic dose and a resting period between the first therapeutic dose and the second therapeutic dose, the regimen comprising: a) administering the first therapeutic dose of a 9-cis-retinyl acetate, wherein the first therapeutic dose is administered at about 40 mg/m$^2$ per day over a period of 7 days to a subject in need thereof; b) providing a resting period from about 7 days to about 21 days; and c) administering a second therapeutic dose of a 9-cis-retinyl acetate following the end of the resting period to the subject.

In some embodiments, the 9-cis-retinyl acetate provides replacement of endogenously produced 11-cis-retinal.

In certain embodiments, the subject is deficient in endogenously produced 11-cis-retinal. In some embodiments, the subject has a LRAT gene mutation. In some embodiments, the subject has a RPE65 gene mutation.

In certain embodiments, the subject has moderate to severe RP. In some embodiments, the subject has mild RP. In some embodiments, the subject has early onset or juvenile RP.

In certain embodiments, the dosing regimen further comprises repeating steps b) and c) one or more times.

In certain embodiments, the second therapeutic dose is administered for substantially the same period and in substantially the same amount as the first therapeutic dose.

In certain embodiments, improving visual function comprises increasing visual field in an eye by at least 20% from baseline as measured by Goldmann Visual Field (GVF) analysis, or increasing visual acuity in an eye by greater than or equal to 5 letters from baseline as measured using an Early Treatment Diabetic Retinopathy Study (ETDRS) eye chart, or both.

In certain embodiments, the therapeutic doses are administered orally.

In certain embodiments of any of the foregoing methods, dosing regimens and kits, the subject is a human subject.

Specific embodiments of these aspects of the disclosure are described in more detail below.

DETAILED DESCRIPTION OF THE DRAWINGS

FIG. 1 provides a schematic drawing of the retinoid cycle.

FIGS. 2A and 2B show GVF response as the proportion of eyes with an improvement over baseline in the intent to treat (ITT) (2A) and the per protocol subset (2B) of RP subject eyes at days 7, 14 and 30 after the first day of dosing.

FIGS. 3A and 3B show GVF response based on VF severity (ITT; all subjects included). FIG. 3A shows the proportion of eyes with greater than 20% improvement in GVF wherein the starting GVF is greater than 20 degrees at baseline (least severe), and FIG. 3B shows the proportion of eyes with greater than 20% improvement in GVF wherein the starting GVF is only central and/or less than 20 degrees at baseline.

FIGS. 4A and 4B show GVF response based on VF severity (Per protocol analysis; 3 subjects excluded). FIG. 4A shows the proportion of eyes with greater than 20% improvement in GVF wherein the starting GVF is greater than 20 degrees at baseline (least severe), and FIG. 4B shows the proportion of eyes with greater than 20% improvement in GVF wherein the starting GVF is only central and/or less than 20 degrees at baseline.

FIG. 5 provides GVF results to day 30 in a multilevel, mixed-effects model analysis of the percent change in retinal area from mean baseline calculated for all subjects (ITT) and the evaluable subset, excluding 3 subjects based on major, defined inclusion/exclusion criteria related to their GVF determinations.

Figure 10:
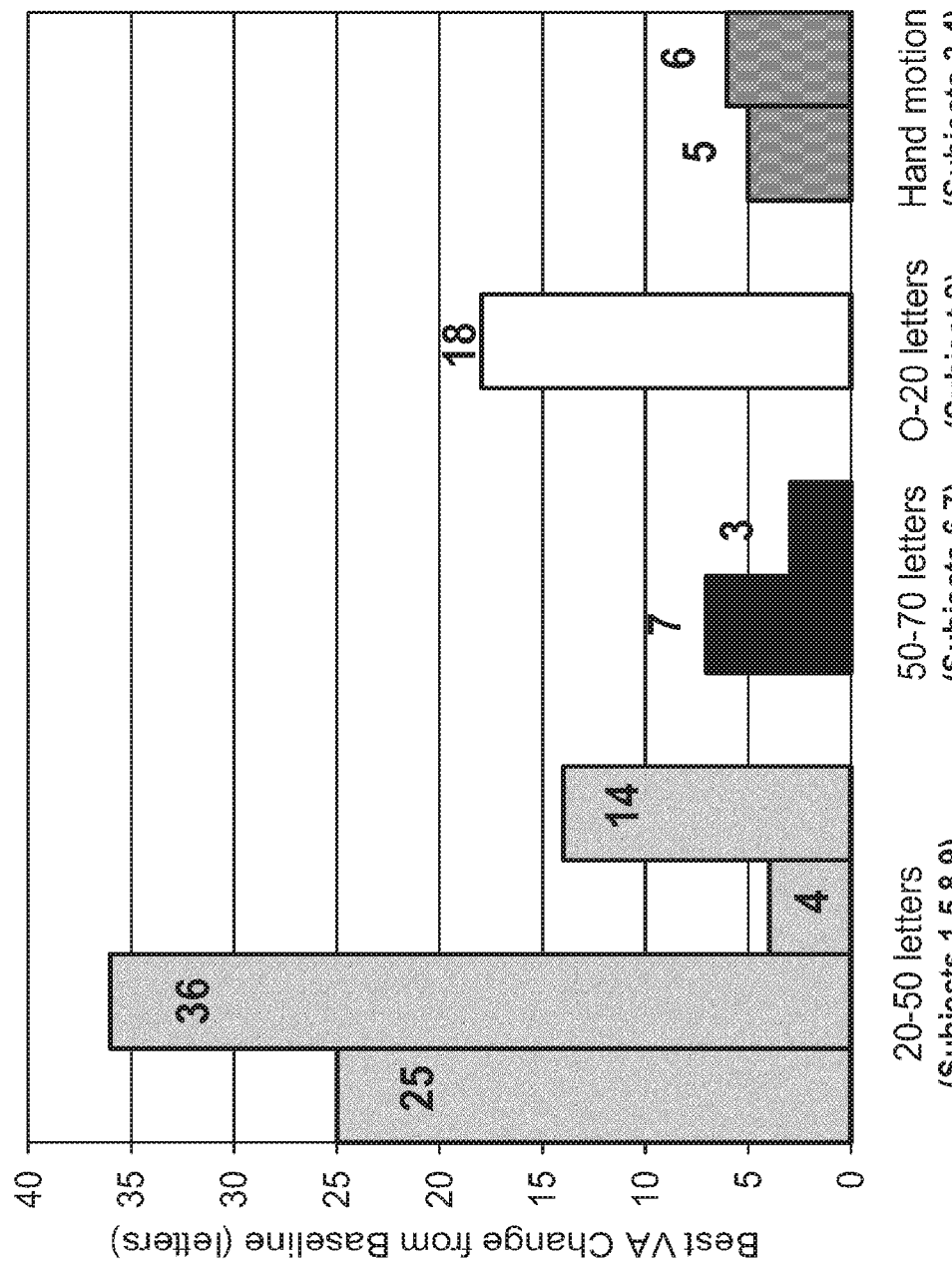

FIG. 10 provide the overall summary of best change in visual acuity (VA) from baseline (ETDRS letter score) from Day 9 to Month 8 post dosing, wherein data has been clustered based on Baseline VA category.

Figure 6:
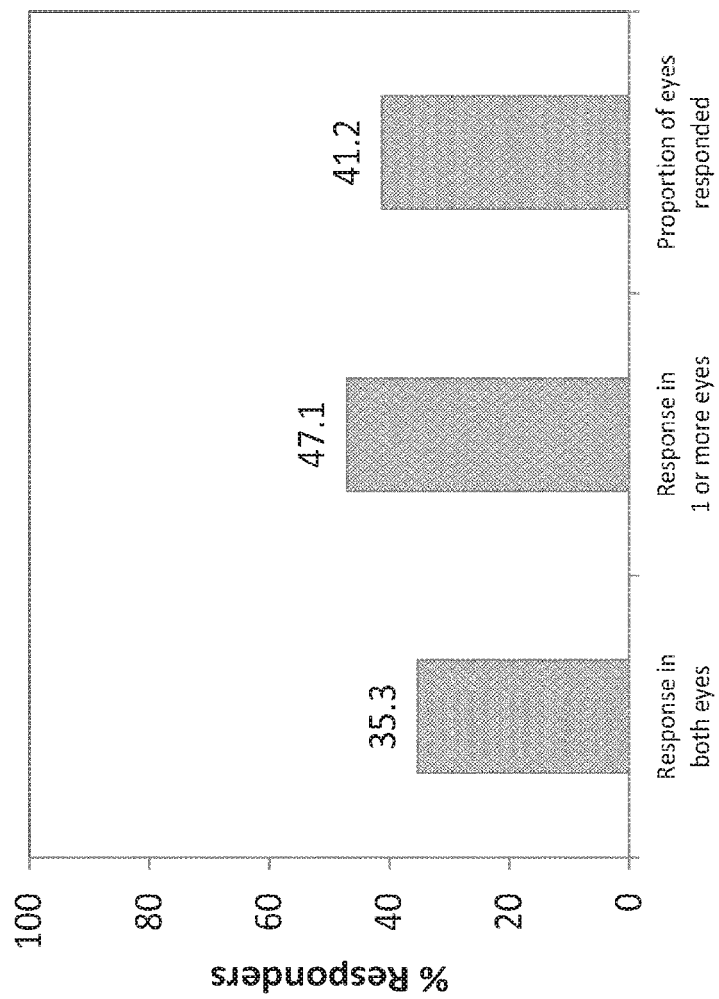
FIG. 6 shows GVF response (ITT) as the percent of GVF responders with response in both eyes, response in one or more eyes, or proportion of eyes responded wherein a responder is defined as patients/eyes for whom retinal area, relative to the mean baseline value, increased by at least 20% on 2 consecutive follow-up visits until month 1.
Figure 11:
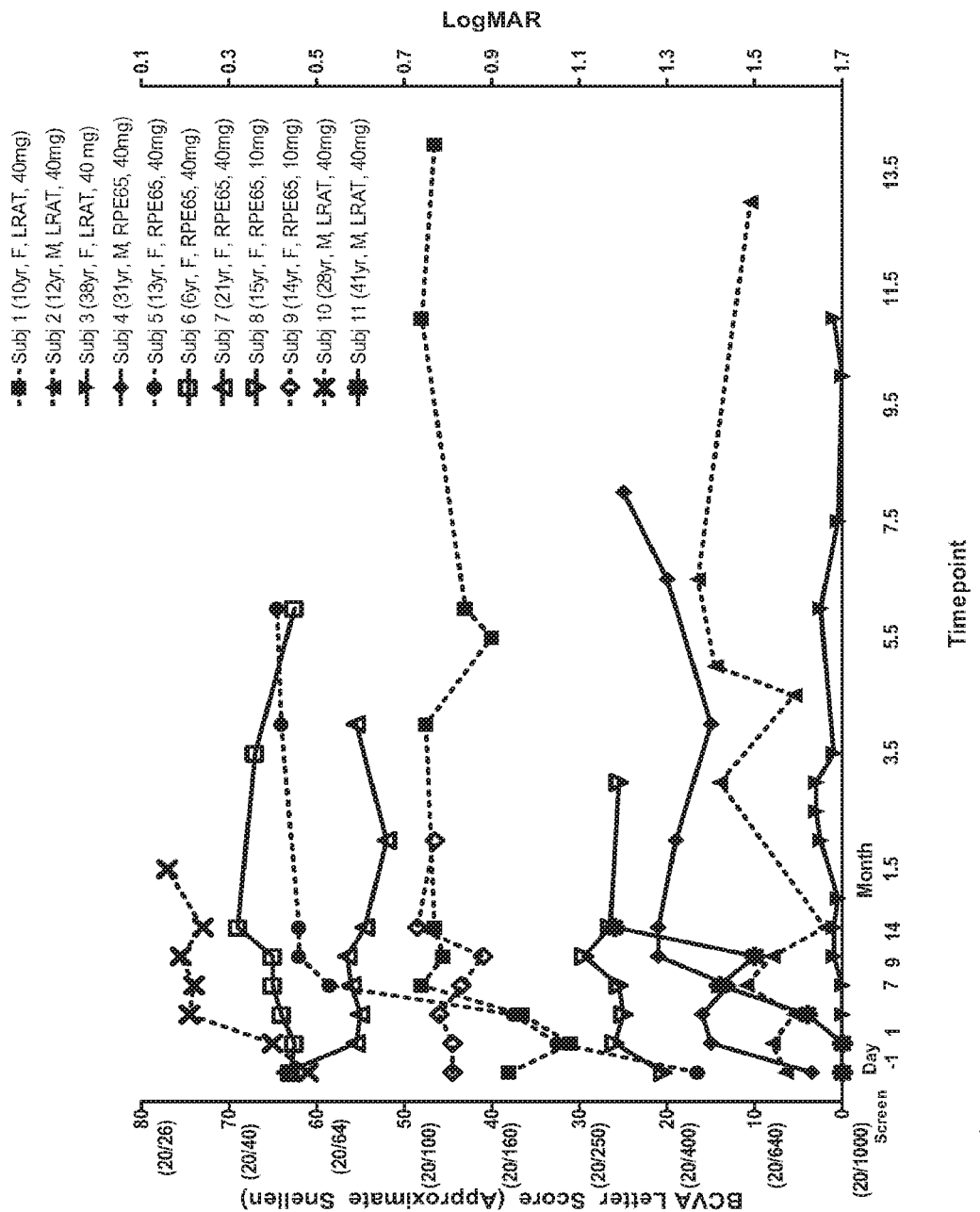

FIG. 11 shows the ETDRS/LogMAR/Snellen equivalent visual acuity (VA) for the eleven subjects of FIG. 6 after treatment with either 40 mg/m2 (40 mg) or 10 mg/m2 (10 mg) of the Composition. Data represents the average letter score for both eyes, with the exception of Subjects 4 and 11, both of which demonstrated measurable letter scores for only one eye.

Figure 12:
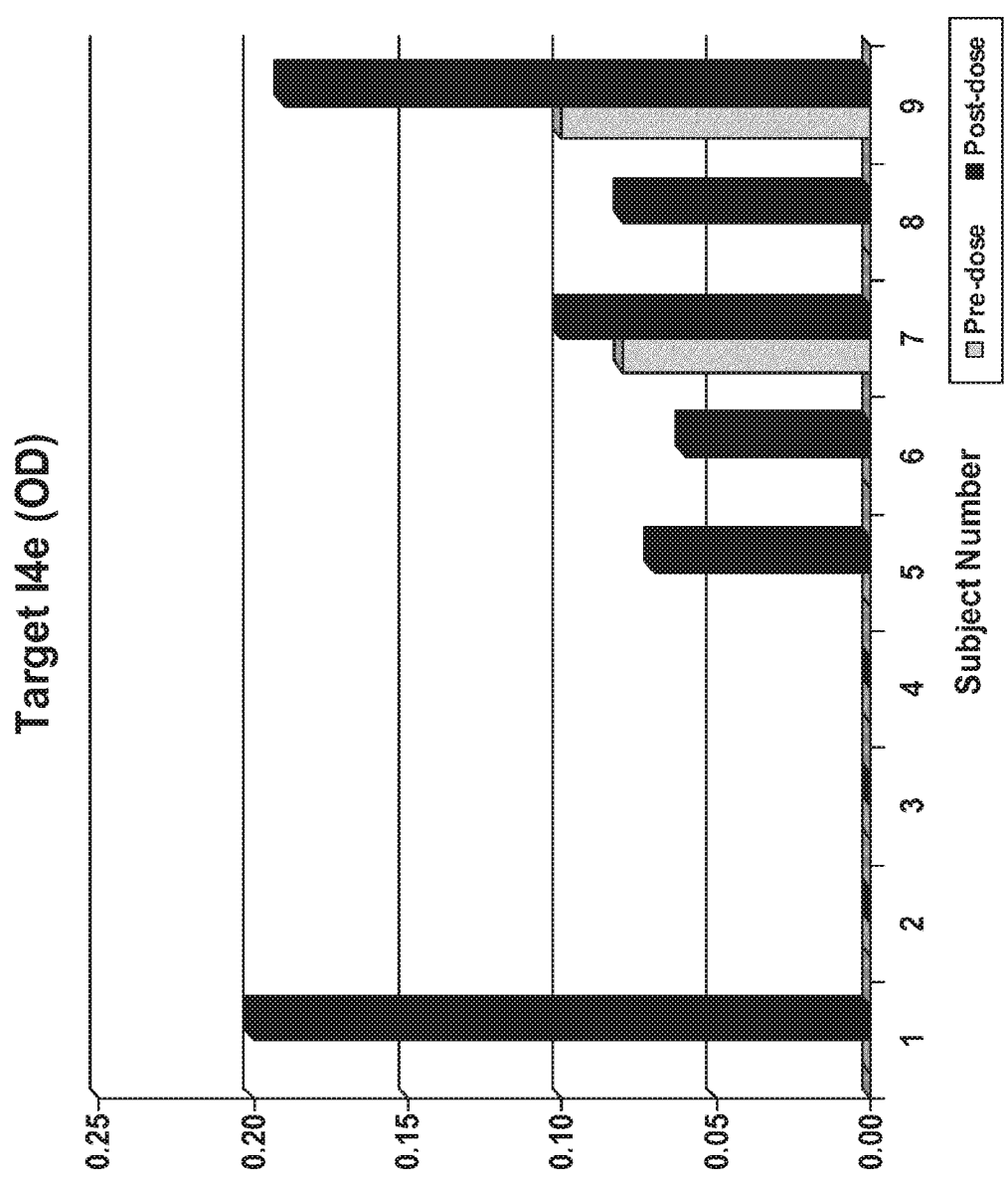

FIG. 12 provides the AMA low vision grid analysis of the Goldmann visual fields (GVF) for Subjects 1-9 wherein analysis was performed of the GVFs observed with the small I4e target (OD) before and at Day 14.

Figure 13:
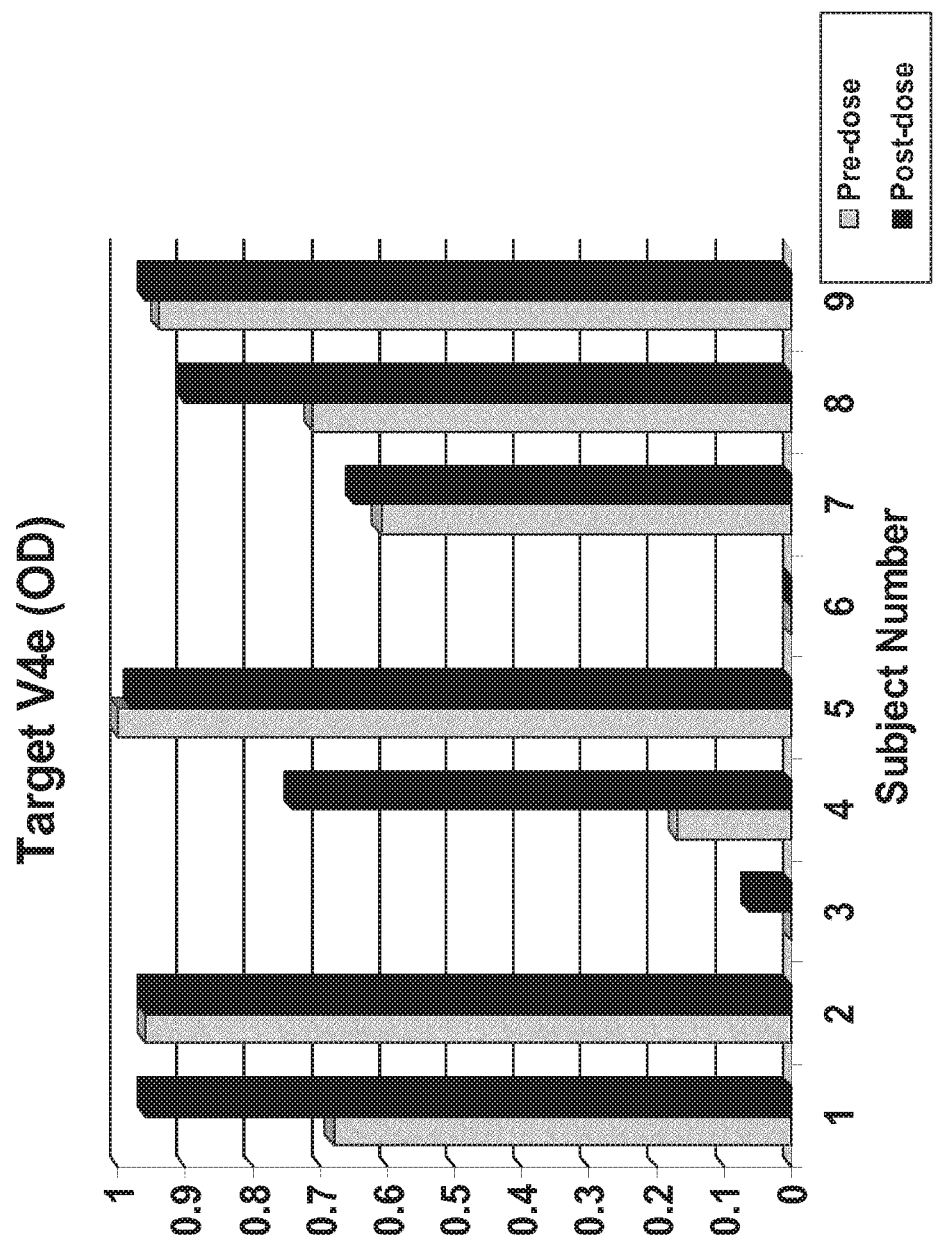

FIG. 13 provides the AMA low vision grid analysis of the Goldmann visual fields (GVF) for Subjects 1-9 wherein analysis was performed of the GVFs observed with the larger V4e target (OD) before and at Day 14.

Figure 14:
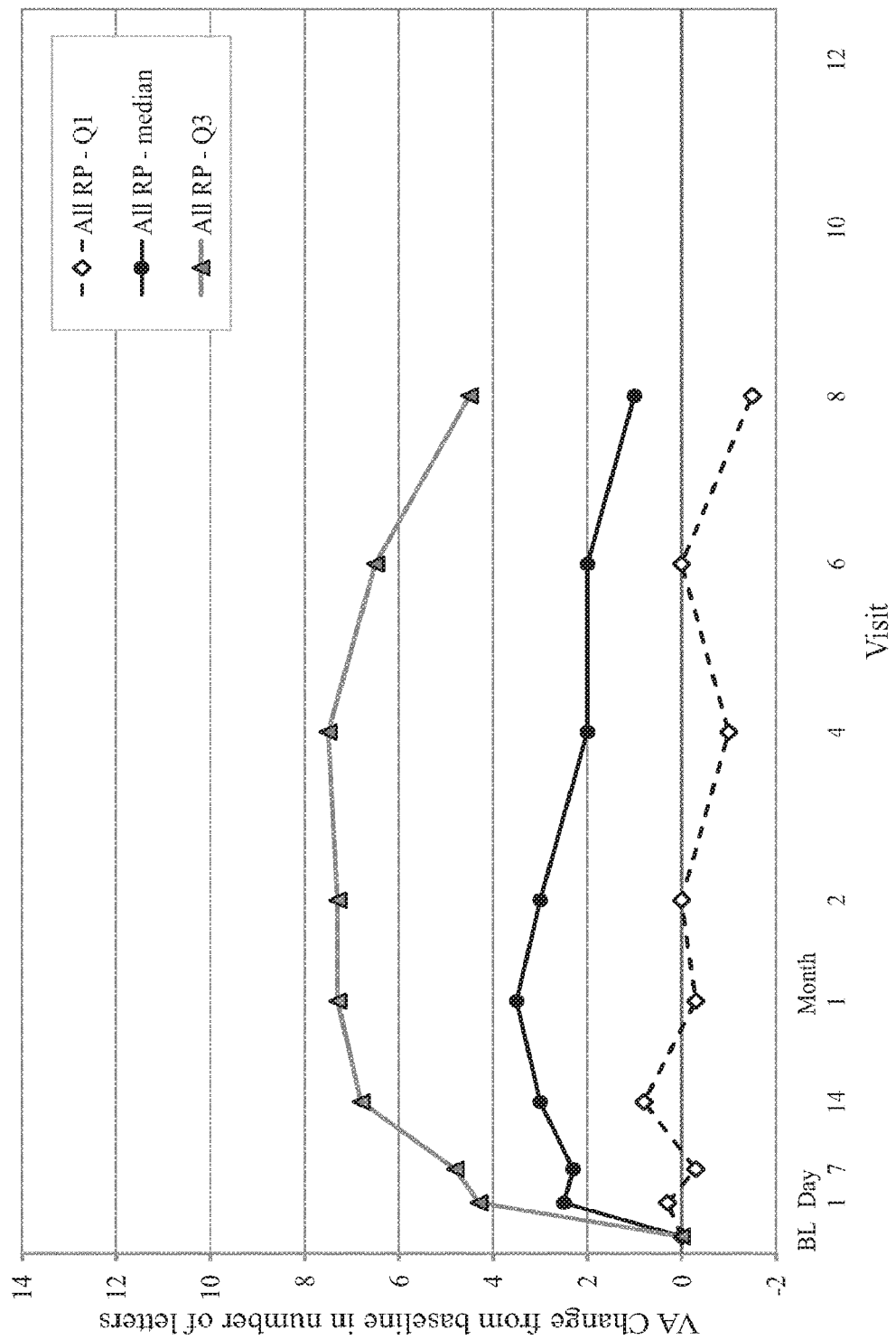

FIG. 14 shows the VA change from baseline in number of ETDRS letters, by quartile, for the RP subjects as defined in Example 4.

DETAILED DESCRIPTION OF THE INVENTION

The present disclosure provides methods, dosing regimens, and kits for improving visual function in a subject with an endogenous retinoid deficiency, such as those caused by mutations in the genes encoding the enzymes and proteins utilized in the visual cycle, such as RP or LCA. The dosing regimens, kits and subsequent methods of improving visual function may be used to provide for efficacy while a clinically relevant safety profile is maintained. Herein, we disclose a dosing regimen comprising a) a first therapeutic dose of a synthetic retinal derivative that provides replacement for deficient endogenously produced 11-cis-retinal, such as a 9- or 11-cis-retinyl ester, wherein the first therapeutic dose is administered for a defined period of time, such as about 1-7 days, b) a resting period of less than one month, such as from 7 to 28 days, following the first therapeutic dose, and c) a second or subsequent therapeutic dose(s) of the synthetic retinal derivative, such as a 9- or 11-cis-retinyl ester. This dosing regimen can provide for clinically efficacious improvement of visual function in a subject with an endogenous 11-cis-retinal deficiency, such as RP or subject, while not providing the synthetic retinal derivative to the patient for a period of time longer than is necessary. In certain embodiments, this dosing regimen avoids the known class-effect safety concerns (e.g. chronic retinoid toxicity) associated with synthetic retinal derivatives.

In one aspect, the present disclosure is directed to a method of improving visual function in a subject having an endogenous retinoid deficiency, such as RP or LCA, comprising a) administering a first therapeutic dose of a synthetic retinoid derivative, such as a 9- or 11-cis-retinyl ester, to a subject in need thereof; b) providing a resting period of less than one month, such as from 7 to 28 days; and c) administering a second therapeutic dose of the synthetic retinoid derivative, such as a 9- or 11-cis-retinyl ester, to said subject following the end of the resting period. The first dose can be administered, typically orally, for one day as a single dose, or over about 2 to about 10 days in a divided dose. Divided dose herein refers to the total therapeutic dose divided over the number of days during the dosing period wherein the dose may be about the same on each day of dosing or the divided dose may be different. In one embodiment the therapeutic dose is administered over a period of about 2 to about 7 days. In another embodiment the therapeutic dose is administered over about 2 days, about 3 days, about 4 days, about 5 days, about 6 days or about 7 days. In one embodiment the therapeutic dose is administered as a divided dose over about 7 days (or one week).

The resting period starts on the day following the last administration of the therapeutic dose and is a time period of less than one month, such as from 7 to 28 days. This disclosure provides that a clinically relevant safety profile is obtained upon repeated dosing with a resting period of less than 30 days. (See Example 5) This safety profile, in combination with a decline of visual function in some subjects, for example in certain RP subjects following administration of the first therapeutic dose after about day 7 to about day 30, indicates that a resting period of less than one month may be desirable. (See Example 2 and FIGS. 2-9) In one aspect, after a first therapeutic dose, visual function testing in certain subjects can identify candidates for early retreatment based on regression or lack of response in parameters of visual function.

In one aspect the resting period is about 2 to about 21 days, about 7 days to about 21 days, or about 14 days to about 21 days. In one aspect the resting period is about 7 to about 28 days, such as about 7 days to about 25 days, or about 7 days to about 23 days. In certain embodiments, the resting period is about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days. In another embodiment, the resting period is about 7 days (or about one week), or about 14 days (or about 2 weeks), or about 21 days (or about 3 weeks). During the resting period a therapeutic dose of a synthetic retinoid derivative is not administered to the subject as part of this dosing regimen.

The second dose or subsequent doses are administered at any time following the end of the resting period. In one aspect, the second dose or subsequent doses are the same as the first therapeutic dose, both in total administration of the synthetic retinal derivative, for example a 9- or 11-cis-retinyl ester (mg/m$^2$) or duration of dosing period. In another aspect, the second or subsequent doses are different than the first therapeutic dose, either in total amount of the synthetic retinal derivative, such as a 9- or 11-cis-retinyl ester, administered (mg/m$^2$) or in the duration of the dosing period.

The resting period and second administration of the synthetic retinal derivative, for example a 9- or 11-cis-retinyl ester, can be repeated as needed to maintain the improvement in the subject's visual function achieved during the first dosing period. It is understood that endogenous retinoid deficiencies, such as RP and LCA, are a chronic conditions, due at least to gene mutations resulting in loss of function of endogenous 11-cis retinal, and that additional dosing beyond the first dose, resting period and second dose may be needed to maintain improvement in the visual function of the subject. It is the combination of the therapeutic dose (amount and duration) with the resting period of less than one month, such as from 7 to 28 days, that provides for a clinically relevant improvement of visual function for a condition associated with an endogenous retinoid with a clinically relevant safety and efficacy profile.

The amount of the therapeutic dose (first, second or subsequent) can be designated either as the total amount administered for a particular dose or as an amount administered over the time period for a particular dose (e.g., first dose or second dose). For example, the first therapeutic dose may be designated as a dose of 280 mg/m$^2$ or as 40 mg/m$^2$ administered per day for 7 days. Thus, in one aspect the therapeutic dose is about 280 mg/m$^2$ to about 420 mg/m$^2$. In another aspect the therapeutic dose is about 40 mg/m$^2$ to about 60 mg/m$^2$ when administered per day for 7 days.

In some embodiments, the therapeutic dose is about, 30-35 mg/m$^2$ per day, 30-40 mg/m$^2$ per day, 40-45 mg/m$^2$ per day, about 40-50 mg/m$^2$ per day, about 45-50 mg/m$^2$ per day, about 45-55 mg/m$^2$ per day, about 50-60 mg/m$^2$ per day or about 55-60 mg/m$^2$ per day.

In some embodiments, the therapeutic dose is about 40 mg/m$^2$ per day, about 45 mg/m$^2$ per day, about 50 mg/m$^2$ per day, about 55 mg/m$^2$ per day or about 60 mg/m$^2$ per day.

In some embodiments, the therapeutic dose is about 5-10 mg/m$^2$ per day, about 10-20 mg/m$^2$ per day, about 20-25 mg/m$^2$ per day, about 20-30 mg/m$^2$ per day, or about 25-30 mg/m$^2$ per day.

In one aspect, the synthetic retinal derivative, such as 9- or 11-cis-retinyl ester, being administered to the subject having an endogenous retinoid deficiency, such as RP or LCA, is 9-cis retinyl acetate, as used in the composition of Example 1, or 11-cis retinyl acetate.

In one embodiment, the present disclosure is directed to a method of improving visual function in a subject having an endogenous retinoid deficiency, such as RP or LCA, wherein the method comprises a) administering a first therapeutic dose of a 9-cis-retinyl acetate, wherein the first therapeutic dose is administered at about 40 mg/m$^2$ per day over a period of 7 days to a subject in need thereof; b) providing a resting period from about 7 days to about 21 days; and c) administering a second therapeutic dose of a 9-cis-retinyl acetate to the subject in need thereof following the end of the resting period.

In another embodiment, the present disclosure is directed to a method of improving visual function in a subject having an endogenous retinoid deficiency, such as RP or LCA, wherein the method comprises a) administering a first therapeutic dose of a 9-cis-retinyl acetate, wherein the first therapeutic dose is administered at about 10 or about 20 or about 40 mg/m$^2$ per day over a period of 5 days to a subject in need thereof; b) providing a resting period from about 21 days to about 25 days; and c) administering a second therapeutic dose of a 9-cis-retinyl acetate to the subject in need thereof following the end of the resting period.

The subject having an endogenous retinoid deficiency, such as RP or LCA, that is being administered a synthetic retinoid derivative, such as an 9- or 11-cis-retinyl ester, can be categorized as having mild, moderate or severe visual impairment based on visual acuity and visual field measurements. Based on World Health Organization (WHO), ICD-9-CM, and medicare benefits criteria, normal vision is defined as a subject with a visual acuity of less than 20/25 and normal visual field, which extends to approximately 60 degrees nasally (toward the nose, or inward) in each eye, to 100 degrees temporally (away from the nose, or outwards), and approximately 60 degrees above and 75 below the horizontal meridian. Mild vision loss is defined as a subject with a visual acuity of 20/30-20/65. Moderate vision loss is defined as a subject with a visual acuity of 20/70-20/190 and a visual field of greater than 20 degrees. Severe vision loss is defined as a subject with a visual acuity of 20/200-20/490 and a visual field of 20 degrees or less. Profound vision loss is defined as a subject with a visual acuity of 20/500-20/1000 and a visual field of 10 degrees or less. Near blindness is defined as a visual acuity of 20/1100-20/2000 and a visual field of 5 degrees or less. Total blindness is defined as a subject with no light perception.

In one aspect, the subject has RP and has been categorized as having moderate to severe RP. In another aspect the RP subject is categorized as having mild RP. In yet another aspect, the RP subject is categorized as having mild to moderate RP.

In one aspect, the improvement in a subject's visual function is measured as a function of baseline. A baseline may be determined for each subject or it may be determined for a group of subjects. In another aspect, a baseline may not be individually determined for a subject but a baseline from a similar group of subjects may be applied to an individual subject.

In one embodiment, the baseline of the subject's visual function is established prior to the administration of the first therapeutic effective dose of the synthetic retinal derivative, such as a 9-cis-retinyl ester or an 11-cis-retinyl ester, or a pharmaceutically acceptable composition thereof by evaluating one or more of the subject's visual field, visual acuity, ability to perform life tasks, retinal sensitivity, dynamic pupillary response, nystagmus, cortical visual function, color vision or dark adaptation. In a further embodiment, the baseline of the subject's visual function is established by evaluating the subject's field of vision. In another embodiment, the baseline of the subject's visual function is established by evaluating the subject's visual acuity. In another embodiment, the baseline is established by evaluating the subject's retinal sensitivity. In another embodiment, the baseline is established by evaluating the subject's visual field, visual acuity and retinal sensitivity.

In another embodiment, establishing the subject's baseline of visual function comprises establishing a baseline of one or more of the subject's visual field, the subject's visual acuity, the subject's retinal sensitivity, the subject's dynamic pupillary response, the subject's nystagmus, the subject's cortical visual function, the subject's ability to perform life tasks, the subject's color vision and the subject's dark adaptation. Preferably, establishing the subject's baseline of visual function comprises establishing the baseline of the subject's visual field, the subject's visual acuity, the subject's ability to perform life tasks, and the subject's retinal sensitivity by established tests.

In one embodiment, the subject's visual function rapidly improves within the dosing period from the baseline of the subject's visual function established prior to administration of the first therapeutic effective amount of the synthetic retinal derivative, for example a 9-cis-retinyl ester or an 11-cis-retinyl ester, to the subject. For purposes of this disclosure, "rapidly improves" refers to a clinically meaningful improvement in a subject's visual functions as compared to the baseline of the subject's visual functions in a period shorter than the first dosing period. Preferably, in one embodiment, the subject's visual functions are significantly improved within one week of the commencement of the dosing period. In another embodiment, the subject's visual functions improve during the dosing period as compared to baseline, and remain above baseline after the completion of the first dosing period and into the resting period. In a further embodiment, the improvement in the subject's visual function in the first dosing period comprises expanding the subject's visual field as compared to the visual field baseline, improving the subject's visual acuity as compared to the visual acuity baseline, and/or improving the subject's retinal sensitivity as compared to the baseline retinal sensitivity.

In one embodiment, the improvement in the subject's visual function comprises an expansion of the subject's visual field or one or more eyes as compared to the baseline. In some embodiments, the improvement in the subject's visual function during the first dosing period comprises increasing visual field in one or more eyes of the subject by at least 30%, 25%, 20% or 15% from baseline as measured by Goldmann Visual Field (GVF) analysis. In some embodiments, the improvement in the subject's visual function comprises increasing visual field in an eye of the subject by at least 20% from baseline as measured by Goldman Visual Field analysis.

In another embodiment, the improvement in the subject's visual function in one or more eyes comprises an improvement in the subject's visual acuity as compared to the baseline. In some embodiments, the improvement in the subject's visual function comprises increasing visual acuity in one or more eyes of the subject by greater than or equal to 5 letters from baseline as measured using an Early Treatment Diabetic Retinopathy Study (ETDRS) eye chart.

In another embodiment, the improvement in the subject's visual function in one or more eyes in the first dosing period comprises an improvement in the subject's retinal sensitivity in one or more eyes as compared to the baseline.

In another embodiment, the improvement in the subject's visual function in the resting period comprises an improvement in the subject's retinal sensitivity in one or more eyes as compared to the improvement in the subject's retinal sensitivity during the first dosing period.

In another embodiment, the improvement in the subject's visual function comprises an improvement in the RP subject's dark adapted perimetry from baseline in one or more eyes.

In one aspect, the present disclosure is directed to a method of improving visual function of a subject with RP or LCA comprising administering at least a first and second therapeutic dose of a synthetic retinal derivative, such as a 9- or 11-cis-retinyl ester, to a subject in need thereof wherein a resting time period between the first dose and the second does is less than one month, such as from 7 to 28 days, and wherein improving visual function comprises increasing visual field in an eye by at least 20% from baseline as measured by Goldmann Visual Field (GVF) analysis, increasing visual acuity in an eye by greater than or equal to 5 letters from baseline as measured using an Early Treatment Diabetic Retinopathy Study (ETDRS) eye chart, or both.

In some embodiments, the resting period is from about 2 days to about 25 days, about 7 days to about 21 days, or about 14 days to about 21 days. In certain embodiments, the resting period is about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, or about 28 days.

In some embodiments, the methods of the present invention provide dosing regimens that combine a clinically relevant safety profile in combination with a plurality of therapeutic dosing periods and resting periods is established. In some embodiments, up to 6, up to 5, up to 4, or up to 3 therapeutic doses are administered in up to 6 months, up to 5 months, up to 4 months or up to 3 months. In some embodiments, up to 12, up to 11, up to 10, up to 9, up to 8, up to 7, up to 6, up to 5, up to 4, or up to 3 therapeutic doses are administered to a subject in up to 12 months, up to 11 months, up to 10 months, up to 9 months, up to 8 months, up to 7 months, up to 6 months, up to 5 months, up to 4 months, or up to 3 months. In another embodiment, up to 3 therapeutic doses are administered in about 3 months. In another embodiment, up to 6 therapeutic doses are administered in about 6 months. In certain instances of the foregoing, no more than one therapeutic dose is administered per month.

In another embodiment, the resting time period between the first dose and the second does is less than one month, such as from 7 to 28 days, and wherein the subject's visual field in an eye is maintained at least 20% over baseline as measured by Goldmann Visual Field (GVF) analysis, and wherein the subject's triglyceride levels and/or HDL levels, cholesterol levels, and LDL levels have not exceeded more than 50% over baseline. In other embodiments, the resting time period between the first dose and the second does is less than one month such as from 7 to 28 days, and the subject's triglyceride levels and/or HDL levels, cholesterol levels, and LDL levels have not exceeded more than 40% over baseline, or 30% or 20% or 10% over baseline. In other embodiments, the resting time period is the period after which the subject's triglyceride levels and or HDL levels, cholesterol levels, and LDL levels have returned to clinically safe and acceptable levels, prior to administering a subsequent therapeutic dose.

In one embodiment, the subject's loss of vision is due to a LRAT or RPE65 gene mutation. In one preferred embodiment, the subject has one or more LRAT gene mutations. In another preferred embodiment, the subject has one or more RPE65 gene mutations. In another preferred embodiment, the subject has one or more null or missense LRAT mutations. In another embodiment, the subject has one or more null or missense RPE65 mutations.

In one embodiment, the subject has autosomal recessive retinitis pigmentosa (arRP). In another embodiment, the subject has autosomal dominant retinitis pigmentosa (adRP). In another embodiment, the subject has moderate to severe RP. In yet another embodiment, the subject has early-onset RP. In yet another embodiment, the subject has juvenile RP.

In another embodiment, the RP subject is an adult. In another embodiment, the RP subject is a pediatric RP subject, for example, an infant, a child or an adolescent.

In one embodiment, the first and any subsequent therapeutic effective amount is administered orally to the subject having an endogenous retinoid deficiency, such as RP or LCA.

In one embodiment, the present disclosure is directed to a dosing regimen for improving visual function of a subject having an endogenous retinoid deficiency, such as RP or LCA, wherein the dosing regimen comprises at least a first therapeutic dose, a second therapeutic dose and a resting period between the first therapeutic dose and the second therapeutic dose, the regimen comprising; a) administering a first dose of a 9- or 11-cis-retinyl ester over a period of about 1 day to about 7 days, such as from 2 to 7 days, to a subject in need thereof; b) providing a resting period of less than one month, such as from 7 to 28 days, between the first therapeutic dose and the second therapeutic dose; and c)

administering the second therapeutic dose of a 9- or 11-cis-retinyl ester to the subject in need thereof following the end of the resting period.

In one embodiment, the 9- or 11-cis-retinyl ester provides replacement of endogenously produced 11-cis retinal. In another embodiment, the 9- or 11-cis-retinyl ester is administered orally to the subject. In yet another embodiment, the dosing regimen further comprises repeating steps b) and c) one or more times as needed. In another embodiment, the dosing regimen further comprises repeating steps b) and c) up to 3 times in a 3 month period. In another embodiment, the dosing regimen further comprises repeating steps b) and c) up to 6 times in a 6 month period. In another embodiment, the dosing regimen further comprises repeating steps b) and c) up to 12 times in a 12 month period. In certain instances of the foregoing, no more than one therapeutic dose is administered per month.

In another embodiment, the present disclosure provides a dosing regimen for improving visual function of a subject having an endogenous retinoid deficiency, such as RP or LCA, wherein the dosing regimen comprises at least a first therapeutic dose, a second therapeutic dose and a resting period between the first therapeutic dose and the second therapeutic dose, the regimen comprising: a) administering the first therapeutic dose of a 9-cis-retinyl acetate, wherein the first therapeutic dose is administered at about 40 mg/m$^2$ per day over a period of 7 days to a subject in need thereof; b) providing a resting period from about 7 days to about 21 days; and c) administering a second therapeutic dose of a 9-cis-retinyl acetate following the end of the resting period to the subject.

In yet another aspect, the present disclosure provides a kit for improving visual function in a subject having an endogenous retinoid deficiency, such as RP or LCA, wherein the kit comprises at least a) a first therapeutic dose of a synthetic retinal derivative, for example a 9- or 11-cis-retinyl ester; and b) instructions for use that provides a resting period between the first therapeutic dose and a second dose, wherein the resting period is less than a month, such as from 7 to 28 days.

In one embodiment, the instructions direct that the first dose is administered over a period of from about 1 to 7 days, such as from about 2 to 7 days. In one aspect, the instructions direct that the first dose is administered over a period of 7 days. In one aspect, the instructions direct that the first dose is administered over a period of 5 days. In another embodiment, the instructions direct that the resting period is from about 2 to about 21 days or from about 7 to about 21 days, or about 7 to about 25 days. In yet another embodiment, the instructions direct that the resting period is about 25 days, or about 23 days, or about 21 days, about 14 days or about 7 days. In another embodiment, the instructions further direct that up to 3 doses are administered in a 3 month period. In another embodiment, the instructions further direct that up to 6 doses are administered in a 6 month period. In another embodiment, the instructions further direct that up to 12 doses are administered in a 12 month period. In certain instances of the foregoing, no more than one therapeutic dose is administered per month.

In an embodiment, the therapeutic dose provided in the kit is from about 280 mg/m$^2$ to about 420 mg/m$^2$. In one aspect, the instructions direct that the therapeutic dose is administered at about 40 mg/m$^2$ per day to about 60 mg/m$^2$ per day. In another aspect, the therapeutic dose comprises 9- or 11-cis retinyl acetate.

The synthetic retinal derivative, for example a 9- or 11-cis-retinyl ester, can be delivered by any pharmacologic vehicle in which it is stably delivered to the subject having an endogenous retinoid deficiency, such as RP or LCA, and effectively released upon administration. The pharmaceutical vehicle art is well familiar with the chemistry of retinoids and the formulations of pharmacologic vehicles for them. These known delivery vehicles include those which have physical properties, chemical properties and release rates that are suited to delivery synthetic retinal derivatives. Liquid delivery vehicles, such as vegetable oils (including soybean, olive, and rapeseed or canola oils) can be used.

In one embodiment, the synthetic retinal derivative is a 11-cis-retinyl ester and is selected from 11-cis-retinyl acetate, 11-cis-retinyl succinate, 11-cis-retinyl citrate, 11-cis-retinyl ketoglutarate, 11-cis-retinyl fumarate, 11-cis-retinyl malate or 11-cis-retinyl oxaloacetate. Preferably the synthetic retinal derivation is 11-cis retinyl acetate.

In another embodiment, the 9-cis-retinyl ester is selected from 9-cis-retinyl acetate or 9-cis-retinyl succinate. In one embodiment, the 9-cis-retinyl ester is 9-cis-retinyl acetate.

In other embodiments, the synthetic retinal derivative is 9-cis retinal, 11-cis-retinal, 9-cis-retinol, or 11-cis-retinol.

In certain embodiments, the pharmaceutically acceptable composition further comprises a lipid vehicle.

In certain embodiments, the pharmaceutically acceptable composition comprises the synthetic retinal derivative, such as a 9-cis-retinyl ester, and soybean oil. Another embodiment of this aspect is wherein the pharmaceutically acceptable composition comprises a 9-cis-retinyl acetate and soybean oil. Yet another embodiment of this aspect is wherein the pharmaceutically acceptable composition comprises a 9-cis-retinyl acetate and soybean oil (USP grade).

In certain embodiments, the pharmaceutical composition further comprises an antioxidant. Another embodiment of this aspect is wherein the pharmaceutically acceptable composition comprises 9-cis-retinyl acetate, soybean oil, and butylated hydroxyanisole (BHA). Yet another embodiment of this aspect is wherein the pharmaceutically acceptable composition comprises 9-cis-retinyl acetate, soybean oil (USP grade), and butylated hydroxyanisole (BHA).

Unless defined otherwise in the specification, the following terms and phrases shall have the following meanings:

As used herein, "visual disorders" refers broadly to disorders in the photoreceptors, tissue or structures of the eye. Visual disorders include, but are not limited to, retinal degeneration, retinal dystrophy, loss of photoreceptor function, photoreceptor cell death and structural abnormalities. Visual disorders of the disclosure are typically characterized by impaired or less than normal (including complete loss of) visual functions in a subject, which include, for example, poor visual acuity, low or lack of retinal sensitivity, narrow or undetectable visual fields, and the like.

"Therapeutically effective amount" refers to that amount of a compound which, when administered to a subject having an endogenous retinoid deficiency, preferably a human, is sufficient to cause a clinically meaningful therapeutic effect.

The term "therapeutic effect" as used herein refers to the improvement of the vision of a subject, in one or both eyes of the subject, wherein an improvement in the subject's visual function in one or both eyes during a therapeutic regimen of the disclosure can be demonstrated by comparing the subject's visual functions of one or both eyes with a baseline measure of the subject's visual functions of one or both eyes prior to administration of a therapeutic regimen of the disclosure or by comparing the subject's visual functions of one or both eyes with a comparable human visual system not receiving the therapeutic regimen.

The loss of vision in RP subjects with retinoid deficiency is typically severe, but can be present in degree and forms that vary from RP subject to RP subject. Subjects can lose their peripheral vision, they can lose their ability to see in low to moderate light, their overall acuity can decline, or other vision loss can occur. This loss can be progressive (especially in adult onset case(s) of retinoid deficiency) eventually leading to very little vision or to complete blindness.

The type and extent of loss can be roughly correlated to the degree of retinoid deficiency, affected cell type (e.g. rods or cones), and/or localization of the retinoid deficiency in the retina. Where the deficiency effect is strongest at the periphery of the retina, peripheral vision losses can be seen earliest and most profoundly. When the deficiency effect is more generalized throughout the retina, an overall loss of acuity is more commonly observed. When the deficiency is great or of long standing, the vision loss (in whatever form) can be more severe and more difficult to successfully improve. Because the nature and degree of vision loss caused by the retinoid deficiency disorder varies from subject to subject, the nature and degree of meaningful improvement of vision will also vary from subject to subject. For example, regaining the ability to see in moderate light can be a meaningful improvement that is manifested in some subjects, for example in some RP patients. For other subjects, for example in some RP patients, a meaningful improvement will be to enhance peripheral vision, or a general improvement in acuity. In certain embodiments, progressive loss of vision may be arrested or reversed by this disclosure. However, in cases where diagnosis and therapeutic intervention occur early, administration of a dosing regimen according to this disclosure may simply limit or slow the progression of vision loss.

Clinically meaningful improvements can be documented by any of several known clinical measures discussed in this application, including acuity, field of vision, light sensitivity, the ability to perform life tasks or a combination of some or all of these. These measures and others are all well known to the clinicians and are routinely used in clinical practice. Clinicians are easily able to identify and observe these changes as part of routine clinical evaluations of subject with visual disorders associated with an endogenous retinoid deficiency, including RP and LCA subjects. Consequently, clinicians are also easily able to observe the identify improvements in vision that are meaningful in the context of a given subject.

Visual Disorders Associated with Endogenous Retinoid Deficiency

The therapeutic regimens and methods of the disclosure are for the improvement of visual function in a subject, having loss of visual functions due to endogenous retinoid deficiency. In some embodiments, the visual disorders are inherited retinal diseases (IRD) caused by gene mutations that disrupt or interfere with the production, conversion and/or regeneration of 11-cis-retinal, resulting in visual impairment or blindness. Such deficiencies are characterized by an absent, deficient or depleted level of one or more endogenous retinoids, such as 11-cis-retinal. Thus, "endogenous retinoid deficiency" refers to prolonged lower levels of endogenous retinoids as compared to the levels found in a healthy eye of a subject of the same species. In some cases, a healthy eye of a subject may experience transient shortage of 11-cis-retinal, which leads to a brief period of blindness followed by vision recovery, while in subjects with an endogenous retinoid deficiency, the subject is deficient in its ability to reliably or rapidly regenerate the endogenous level of 11-cis-retinal, which leads to prolonged and/or pronounced 11-cis retinal deficits.

In one embodiment, the therapeutic regimens and methods of the disclosure are for the improvement of visual function in a subject, having an inherited retinal disorder, such as RP, LCA and subtypes thereof. In other embodiments, the subject has Retinitis *Punctata* Albesciens, or Congenital Stationary Night Blindness (CSNB) or Fundus Albipunctatus, or subtypes thereof.

Figure 1:
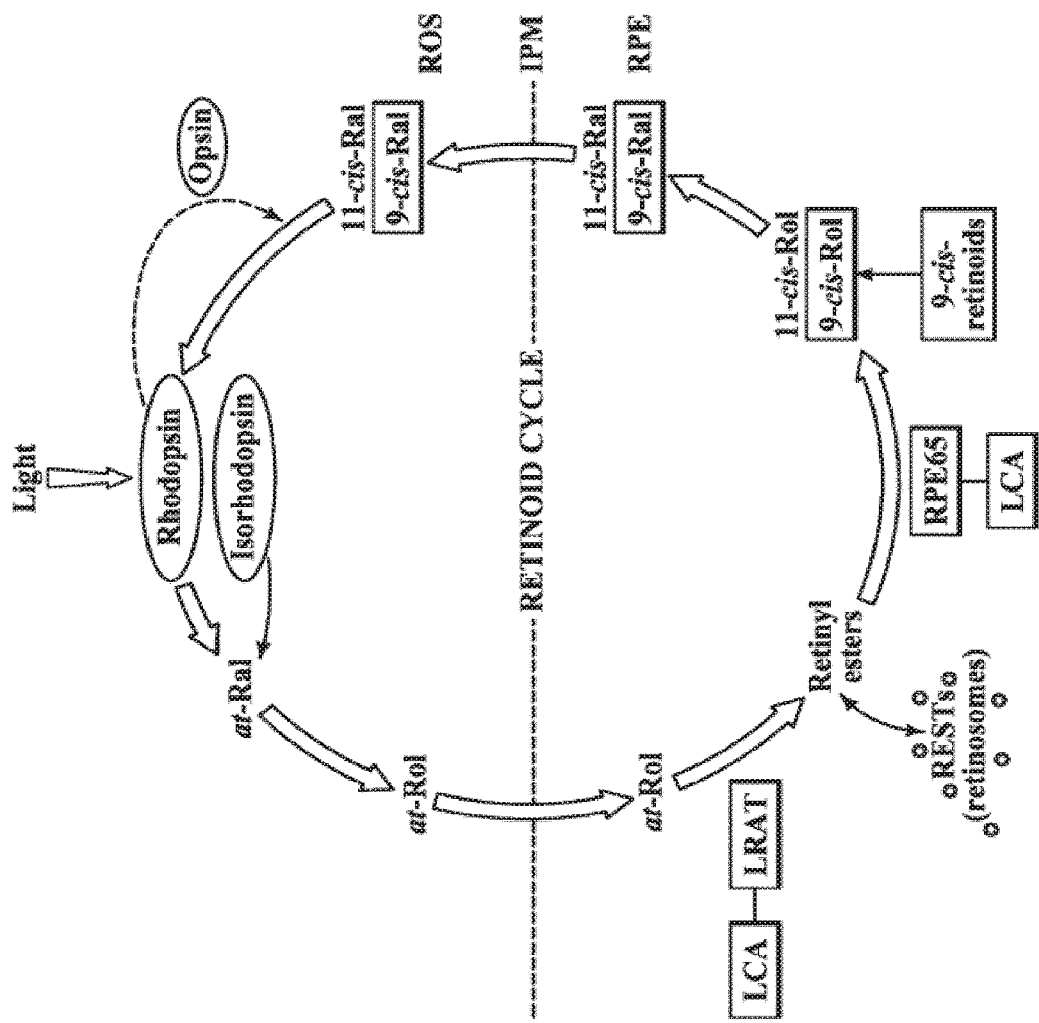

Endogenous retinoid deficiency can be caused by one or more defects in the visual cycle which includes enzymatic deficiencies and impaired transport processes between the photoreceptors and retinal pigment epithelial cells (RPE). FIG. 1 schematically shows a vertebrate, preferably the human, visual cycle (or retinoid cycle), which operates between the RPE and the outer segments of photoreceptors. 11-cis-retinal is regenerated through a series of enzymatic reactions and transport processes to and from the RPE after which it binds to opsin to form rhodopsin in the photoreceptor. Rhodopsin is then activated by light to form metarhodopsin which activates the phototransduction cascade while the bound cis-retinoid is isomerized to all-trans-retinal (von Lintig, J. et al., Trends Biochem Sci Feb. 24 (2010)).

Mutations in more than a dozen genes encoding retinal proteins have been identified that participate in several biochemical pathways in the visual cycle. For example, mutations in genes that encode lecithin:retinoid acetyl transferase (the LRAT gene) and retinal pigment epithelium protein 65 kDa (the RPE65 gene) disrupt the retinoid cycle, resulting in a deficiency of 11-cis-retinal, an excess of free opsin, an excess of retinoid waste (e.g., degradation) products and/or intermediates in the recycling of all-trans-retinal, or the like.

Endogenous retinoid levels in a subject's eyes, for example an RP or LCA subject's eyes, and deficiencies of such levels may be determined in accordance with the methods disclosed in, for example, U.S. Published Patent Application No. 2005/0159662 (the disclosure of which is incorporated by reference herein in its entirety). Other methods of determining endogenous retinoid levels in a vertebrate eye and a deficiency of such retinoids include, for example, analysis by high pressure liquid chromatography (HPLC) of retinoids in a blood sample from a subject. For example, a blood sample can be obtained from a subject and retinoid types and levels in the sample can be separated and analyzed by normal phase high pressure liquid chromatography (HPLC) (e.g., with a HP 1100 HPLC and a Beckman, Ultrasphere-Si, 4.6 mm×250 mm column using 10% ethyl acetate/90% hexane at a flow rate of 1.4 ml/minute). The retinoids can be detected by, for example, detection at 325 nm using a diode-array detector and HP Chemstation A.03.03 software. A deficiency in retinoids can be determined, for example, by comparison of the profile of retinoids in the sample with a sample from a control subject (e.g., a normal subject).

Various conditions can cause a subject to be predisposed to or develop endogenous retinoid deficiency. For example, a subject that has an RPE65 gene mutation or an LRAT gene mutation is genetically predisposed to endogenous retinoid deficiency and visual impairment that ultimately lead to complete vision loss and severe retinal dystrophy. In particular, RPE65 and LRAT gene mutations are found in RP and LCA subjects.

RP can be caused by defects in many different genes with more than 200 causative RP mutations detected in more than 100 different genes to date. RP genotypes are heterogeneous, and RP subjects with the same mutation can exhibit different phenotypes. RP may be inherited by autosomal dominant, autosomal recessive, or X-linked traits. In recent years, mutations in the LRAT and RPE65 genes have been discovered in RP subjects with arRP or adRP. These specific mutations are linked to defects in retinoid metabolism of the visual cycle and may result in photoreceptor degeneration.

As noted herein, the protein encoded by the RPE65 gene has a biochemical association with retinol binding protein and 11-cis-retinol dehydrogenase and is essential for 11-cis-retinal production (Gollapalli, D. R. et al., Biochemistry. 42(19):5809-5818 (2003) and Redmond, T. M. et al., Nat Genet. 20(4):344-351 (1998)). Preclinical and clinical information show that loss of the function of the RPE65 protein blocks retinoid processing after esterification of vitamin A to membrane lipids and results in loss of vision.

RPE65 mutations are predominantly associated with early-onset severe retinal dystrophy, with rod-cone degeneration, nystagmus and severe visual loss within the first few years of life. The severity of the disease resulting from mutations in RPE65 appears to be largely independent of the mutation types present in the patients. Many RPE65 patients share a common phenotype characterized by poor but useful visual function in early life (measurable cone ERGs) that declines dramatically throughout the school age years. In addition, a number of these patients retain residual islands of peripheral vision, although considerably compromised, into the third decade of life.

Progressive visual field (VF) loss is one of the hallmarks of RP and is commonly used as a means to monitor the progression of the disease. It has been observed that most RP subjects are legally blind by age 40 because of severely constricted visual fields due to loss of rod function exceeding reduction of cone sensitivity.

Visual acuity (VA) impairment may also be noted during the course of the RP although RP subjects with early-onset RP have been reported to have more stable VA than other RP types and the level of VA impairment can vary widely amongst RP subjects. For example, it has been reported for some RP patients with advanced RP with a small island of remaining central VF, that VA may remain normal. In other RP patients, VA decreases can be more pronounced.

Subject Populations

While a subject having a visual disorder associated with an endogenous retinoid deficiency (as defined herein) may be treated by the therapeutic regimens and methods of the disclosure, in some embodiments, there may be a physiological window of opportunity wherein the therapeutic regimen or method is the most effective in slowing the rate of decline or improving visual function to the subject. In one embodiment, the window of opportunity for the therapeutic regimens of the disclosure to be the most effective in a subject is defined as the interval between loss of visual function and retinal degeneration, particularly with respect to photoreceptor cell degeneration. Subjects in certain age groups may particularly benefit from the therapeutic regimens of the disclosure. More specifically, subjects with a lesser degree of retinal/photoreceptor degeneration tend to have a better or faster response to the therapeutic regimen of the disclosure and/or may have a longer resting period before a subsequent dosing period is needed. For example, in certain embodiments, younger subjects with a loss of visual function due to an endogenous retinal deficiency, such as LCA or RP, may retain a higher percentage of dormant photoreceptors. Such dormant photoreceptors are capable of responding to the therapeutic regimens of the invention. In particular, in improving visual function in a subject arising from inherited childhood blindness such as LCA or early onset RP, such as arRP, younger subjects may expect a greater recovery of visual functions because their retinal degeneration is less advanced. Thus, in one embodiment of the invention, the subject is a human juvenile, i.e., younger than 15 years, old upon commencement of the therapeutic regimen. In other embodiments of the invention, the subject is a human newborn or a human infant younger than 1 year old, younger than 18 months, younger than 24 months or younger than 36 months old when the therapeutic regimen is commenced. In other embodiments, the subject is a human of 5 years old or older when the therapeutic regimen is commenced. In further embodiments, the human subject is 10 years old or older when the therapeutic regimen is commenced.

In some instances, RP may appear in a human subject during the second decade or even later. The average age of diagnosis for arRP in a human is about 36 years old (Tsujikawa M. et al., Arch Ophthalmol 126(3) 337-340 (2008)). Thus, in other embodiments, the human RP subject is 15 years old or older when the therapeutic regimen is commenced. In more specific embodiments, the human RP subject at commencement of the regimens, methods and administration of compositions described herein is 20 years old or older, 30 years old or older, 40 years or older, 50 years or older, 60 years or older or 70 years or older when the therapeutic regimen is initiated. In other embodiments, the human RP subject at commencement of the regimens, methods and administration of compositions described herein is about 20 years of age or less, or about 30 years of age or less, or about 40 years of age or less, or about 50 years of age or less.

In an embodiment, for any of these subjects, the therapeutic regimens and methods of the disclosure should commence as soon as a diagnosis of a visual disorder as defined herein is ascertained, such that any degeneration of the retina, in particular the photoreceptors, has not reached a point where the therapeutic regimens of the disclosure would be ineffective in improving visual function in the subject.

Synthetic Retinal Derivatives

The present disclosure provides methods of improving visual function in a subject. Synthetic retinal derivatives can be administered to improve visual function, and/or to ameliorate the effects of a deficiency in retinoid levels. Visual function can be improved, for example, by providing a synthetic retinoid that can act as an 11-cis-retinoid replacement and/or an opsin agonist. The synthetic retinoid also can ameliorate the effects of a retinoid deficiency on a subject's visual system. A synthetic retinoid can be administered prophylactically (e.g., to a subject diagnosed with an endogenous retinoid deficiency, to prevent, slow, or delay deterioration or further deterioration of the subject's visual function, as compared to a comparable subject not receiving the synthetic retinoid) or therapeutically to a subject.

The synthetic retinal derivatives are retinoids derived from 11-cis-retinal or 9-cis-retinal. In certain embodiments, the synthetic retinal derivative is a synthetic 9- or 11-cis retinoid. In other embodiments, the synthetic retinoid is a derivative of 11-cis-retinal or 9-cis-retinal. In some embodiments, a synthetic retinal derivative can, for example, be a retinoid replacement, supplementing the levels of endogenous retinoid. In other embodiments, the synthetic retinal derivatives are 9- or 11-cis retinyl esters. In other embodiments, the synthetic retinal derivative is 9-cis-retinol or 11-cis-retinol. In other embodiments, the synthetic retinal derivative is 9-cis-retinal or 11-cis-retinal.

Without intending to be bound by any particular theory, in certain embodiments of the present invention, the synthetic retinal derivatives used in the therapeutic regimens of the disclosure provide replacements for endogenously produced 11-cis-retinal, thereby restoring the key biochemical component of the visual cycle. A synthetic retinal derivative suitable for the therapeutic regimens of the disclosure can be a derivative of 9-cis-retinal or 11-cis-retinal. Like 11-cis-retinal, 9-cis-retinal can bind to opsin to form photoactive isorhodopsin which, when bleached, undergoes conformational changes via the same photoproducts as 11-cis-retinal regenerated rhodopsin (Yoshizawa, T. et al., Nature 214, 566-571 (1967) and Filipek S. et al., Annu Rev Physiol 65:851-79 (2003)). 9-cis-retinal and its derivatives are generally more thermodynamically stable than their 11-cis retinal counterparts.

The synthetic retinal derivatives can be converted directly or indirectly into a retinal or a synthetic retinal analog. Thus, in some aspects, the compounds according to the present disclosure can be described as pro-drugs, which upon metabolic transformation are converted into 9-cis-retinal, 11-cis-retinal or a synthetic retinal derivative thereof. Metabolic transformation can occur, for example, by acid hydrolysis, esterase activity, acetyltransferase activity, dehydrogenase activity, or the like. For example, without wishing to be bound by theory, it is thought that a synthetic 9-cis-retinal derivative (e.g., a 9-cis-retinyl ester, such as 9-cis-retinyl acetate), is converted to 9-cis-retinol in the alimentary pathway, transported to the retina through the bloodstream and converted to 9-cis-retinal in the RPE.

In one embodiment, 9- and 11-cis-retinyl esters suitable for the methods of the present disclosure can be the 9-cis-retinyl esters or 11-cis-retinyl esters described in International Published Patent Application No. and WO 2006/002097 and Published U.S. Application No. 2010/0035986, which applications are incorporated herein by reference in their entireties. In certain embodiments of the present invention, the synthetic retinal derivatives can directly, or via a metabolite thereof, bind to opsin and function as an opsin agonist. As used herein, the term "agonist" refers to a synthetic retinal derivative that binds to opsin and facilitates the ability of the opsin/synthetic retinal derivative complex to respond to light. As an opsin agonist, a synthetic retinal derivative can create a pharmacological bypass of a blocked retinoid cycle, thus sparing the requirement for endogenous retinoid (e.g., 11-cis-retinal).

In certain embodiments, the 9- or 11-cis-retinyl ester for use in the present invention is not a naturally occurring retinyl ester normally found in the eye. In some embodiments, the 9- or 11-cis-retinyl ester is an isolated retinyl ester. As used herein, "isolated" refers to a molecule that exists apart from its native environment and is therefore not a product of nature. An isolated molecule may exist in a purified form or may exist in a non-native environment. In additional embodiments, the synthetic retinal derivative is 9-cis-retinol, 9-cis-retinal, 11-cis-retinol or 11-cis-retinal.

In one aspect, the 9- or 11-cis-retinyl ester can be a 9-cis-retinyl ester of formula I:

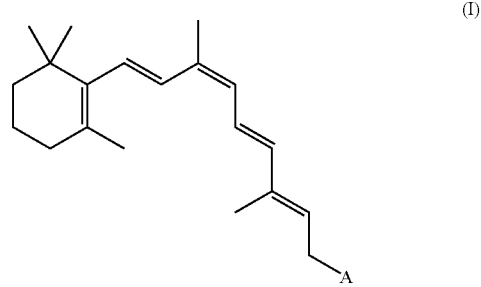

wherein A is —OC(O)R, and
R is an optionally substituted alkyl group or alkenyl group.

In certain embodiments, R is a C1 to C24 straight chain or branched alkyl group, such as a C1 to C14 or C1 to C12 straight chain or branched alkyl group. In other embodiments, R can be a C1 to C10 straight chain or branched alkyl group, such as a C1 to C8 or a C1 to C6 straight chain or branched alkyl group. Exemplary alkyl groups include methyl, ethyl, n-propyl, n-butyl, n-pentyl, n-hexyl, n-heptyl, n-octyl, n-nonyl, n-decyl, n-undecanyl.

In certain embodiments, R is methyl.

In certain embodiments, R is a C15 alkyl group. In certain such embodiments, the compound of formula I is 9-cis-retinyl palmitate.

In certain embodiments, R is a C17 alkyl group. In certain such embodiments, the compound of formula I is 9-cis-retinyl stearate.

In certain embodiments, R is a C17 alkenyl group. In certain such embodiments, the compound of formula I is 9-cis-retinyl oleate.

In certain embodiments, R is a substituted alkyl or alkenyl group, such as an alkyl or alkenyl group substituted with one or more carboxylic acids. In certain embodiments, the alkyl or alkenyl group substituted with one or more carboxylic acids is further substituted with one or more hydroxyl groups. In certain embodiments of the foregoing, A is a polycarboxylic acid group, such as a di-, tri- or higher order carboxylic acid. For example, in some embodiments, A is a C2-C22, C3-C22, C2-C10, C3-C10, C4-C10, C4-C8, C4-C6 or C4 polycarboxylic acid group. Certain exemplary embodiments of the foregoing include embodiments wherein A is an oxalic acid (ethanedioic acid), malonic acid (propanedioic acid), succinic acid (butadedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid or ketoglutaratic acid group, or the like. In some embodiments, the polycarboxylic acid group is not tartaric acid. (In this context, the term "group" refers to a radical which may be covalently linked to the terminal carbon of the polyene chain of formula I.)

Examples of suitable synthetic 9-cis retinyl esters include, for example, 9-cis-retinyl acetate, 9-cis-retinyl succinate, 9-cis-retinyl citrate, 9-cis-retinyl ketoglutarate, 9-cis-retinyl fumarate, 9-cis-retinyl malate or 9-cis-retinyl oxaloacetate. In certain embodiments, the 9-cis-retinyl ester is 9-cis-retinyl acetate,

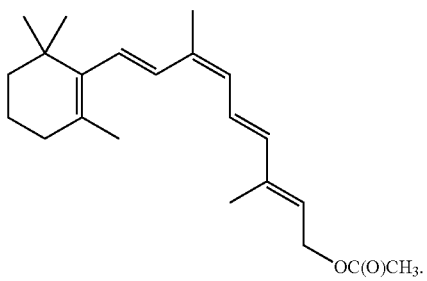

In a related aspect, the 11-cis-retinyl ester may be an 11-cis-retinyl ester of formula II:

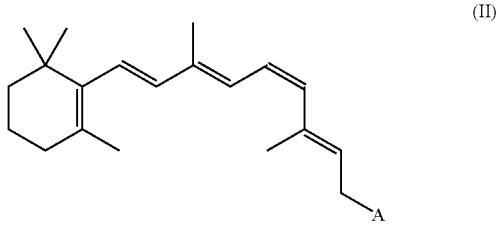

(II)

wherein A is —OC(O)R, and

R is an optionally substituted alkyl group or alkenyl group.

In certain embodiments, R is a C1 to C24 straight chain or branched alkyl group, such as a C1 to C14 or C1 to C12 straight chain or branched alkyl group. In other embodiments, R can be a C1 to C10 straight chain or branched alkyl group, such as a C1 to C8 or a C1 to C6 straight chain or branched alkyl group. Exemplary alkyl groups include methyl, ethyl, n-propyl, n-butyl, n-pentyl, n-hexyl, n-heptyl, n-octyl, n-nonyl, n-decyl, n-undecanyl.

In certain embodiments, R is methyl.

In certain embodiments, R is a C15 alkyl group. In certain such embodiments, the compound of formula II is 11-cis-retinyl palmitate.

In certain embodiments, R is a C17 alkyl group. In certain such embodiments, the compound of formula II is 11-cis-retinyl stearate.

In certain embodiments, R is a C17 alkenyl group. In certain such embodiments, the compound of formula II is 11-cis-retinyl oleate.

In certain embodiments, R is a substituted alkyl or alkenyl group, such as an alkyl or alkenyl group substituted with one or more carboxylic acids. In certain embodiments, the alkyl or alkenyl group substituted with one or more carboxylic acids is further substituted with one or more hydroxyl groups. In certain embodiments of the foregoing, A is a polycarboxylic acid group, such as a di-, tri- or higher order carboxylic acid. For example, in some embodiments, A is a C2-C22, C3-C22, C2-C10, C3-C10, C4-C10, C4-C8, C4-C6 or C4 polycarboxylic acid group. Certain exemplary embodiments of the foregoing include embodiments wherein A is an oxalic acid (ethanedioic acid), malonic acid (propanedioic acid), succinic acid (butadedioic), fumaric acid (butenedioic acid), malic acid (2-hydroxybutenedioic acid), glutaric acid (pentanedioic acid), adipic acid (hexanedioic acid), pimelic acid (heptanedioic), suberic acid (octanedioic), azelaic acid (nonanedioic acid), sebacic acid (decanedioic acid), citric acid, oxaloacetic acid or ketoglutaratic acid group, or the like. In some embodiments, the polycarboxylic acid group is not tartaric acid. (In this context, the term "group" refers to a radical which may be covalently linked to the terminal carbon of the polyene chain of formula II.).

Examples of suitable synthetic 11-cis retinyl esters include, for example, 11-cis-retinyl acetate, 11-cis-retinyl succinate, 11-cis-retinyl citrate, 11-cis-retinyl ketoglutarate, 11-cis-retinyl fumarate, 11-cis-retinyl malate or 11-cis-oxaloacetate. In certain preferred embodiments, the 11-cis-retinyl ester is 11-cis-retinyl acetate,

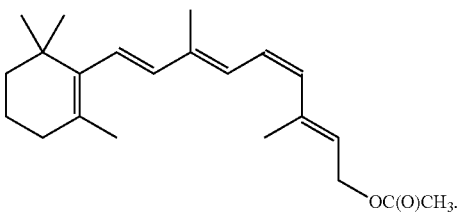

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic", as used herein, includes straight, chained, branched or cyclic hydrocarbons which are completely saturated or contain one or more units of unsaturation. Aliphatic groups may be substituted or unsubstituted.

The term "alkoxy" refers to an oxygen having an alkyl group attached thereto. Representative alkoxy groups include methoxy, ethoxy, propoxy, tert-butoxy and the like.

"Alkenyl" refers to a straight or branched hydrocarbon chain radical consisting solely of carbon and hydrogen atoms, containing at least one unsaturation (i.e., C=C), having from two to up to twenty carbon atoms. In various embodiments, R is C12-17 alkenyl, C1-8 alkenyl, C1-6 alkenyl or C1-4 alkenyl. Unless stated otherwise specifically in the specification, an alkyl group may be optionally substituted with one or more substituents. Such substituents may occur on one or more carbons that are included or not included in one or more double bonds. Exemplary substituents include halo (including —F, —Br, —Cl and —I), cyano (—CN), nitro (—NO2), oxo (=O), and hydroxyl (—OH).

In certain embodiments, "alkyl" refers to the radical of saturated aliphatic groups, including straight-chain alkyl groups and branched-chain alkyl groups. In certain embodiments, an alkyl may comprise twelve to seventeen carbon atoms (also referred to as "C12-17 alkyl"). In certain embodiments, an alkyl may comprise twelve to fifteen carbon atoms (also referred to as "C12-15 alkyl"). In certain embodiments, an alkyl may comprise one to eight carbon atoms (also referred to as "C1-8 alkyl"). In other embodiments, an alkyl may comprise one to six carbon atoms (also referred to as "C1-6 alkyl"). In further embodiments, an alkyl may comprise one to four carbon atoms (also referred to as "C1-4 alkyl"). The alkyl is, for example, methyl, ethyl, n-propyl, 1-methylethyl (iso-propyl), n-butyl, n-pentyl, 1,1-dimethylethyl (t-butyl), 3-methylhexyl, 2-methylhexyl, and the like.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety. In certain embodiments, an alkyl group may be optionally substituted by one or more of the following substituents: halo (including —F, —Br, —Cl and —I), cyano (—CN), nitro (—NO2), oxo (=O), and hydroxyl (—OH).

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. Co alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "amide", as used herein, refers to a group

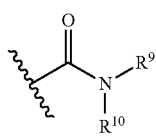

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

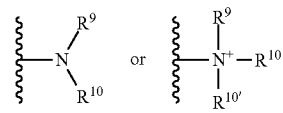

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "carbamate" is art-recognized and refers to a group

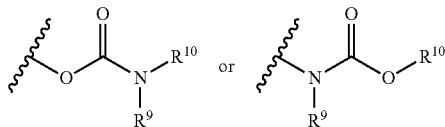

wherein $R^9$ and $R^{10}$ independently represent hydrogen or a hydrocarbyl group, such as an alkyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —$OCO_2$—$R^9$, wherein $R^9$ represents a hydrocarbyl group, such as an alkyl group.

The term "carboxy", as used herein, refers to a group represented by the formula —$CO_2H$.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen", as used herein, means halogen and includes chloro, fluoro, bromo, and iodo.

The term "heteroalkyl", as used herein, refers to a saturated or unsaturated chain of carbon atoms including at least one heteroatom (e.g., O, S, or $NR^{50}$, such as where $R^{50}$ is H or lower alkyl), wherein no two heteroatoms are adjacent.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitation aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt or ester thereof.

The term "sulfonamide" is art-recognized and refers to the group represented by the general formulae

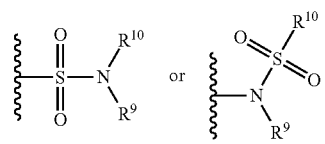

wherein $R^9$ and $R^{10}$ independently represents hydrogen or hydrocarbyl, such as alkyl.

The term "sulfoxide" is art-recognized and refers to the group —S(O)—R$^9$, wherein R$^9$ represents a hydrocarbyl, such as alkyl, aryl, or heteroaryl.

The term "sulfonate" is art-recognized and refers to the group —SO$_3$H, or a pharmaceutically acceptable salt or ester thereof.

The term "sulfone" is art-recognized and refers to the group —S(O)$_2$—R$^9$, wherein R$^9$ represents a hydrocarbyl, such as alkyl, aryl, or heteroaryl.

The term "thioester", as used herein, refers to a group —C(O)SR$^9$ or —SC(O)R$^9$ wherein R$^9$ represents a hydrocarbyl, such as alkyl.

The term "thioether", as used herein, is equivalent to an ether, wherein the oxygen is replaced with a sulfur.

The term "urea" is art-recognized and may be represented by the general formula

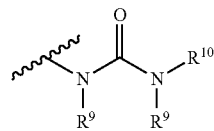

wherein R$^9$ and R$^{10}$ independently represent hydrogen or a hydrocarbyl, such as alkyl.

At various places in the present specification substituents of compounds of the disclosure are disclosed in groups or in ranges. It is specifically intended that the disclosure include each and every individual subcombination of the members of such groups and ranges. For example, the term "C1-C6 alkyl" is specifically intended to individually disclose methyl, ethyl, propyl, isopropyl, n-butyl, sec-butyl, isobutyl, etc.

In certain embodiments, the 9-cis-retinyl esters can be converted by the liver to a metabolic pro-drug form, namely fatty acid 9-cis-retinyl esters, which are stored in the liver in hepatic lipid droplets. Fatty acid 9-cis-retinyl esters and retinol are mobilized from the liver and enter the circulation where they travel to the eye and RPE. There, they are converted to 9-cis-retinal which ultimately combines with photoreceptor opsins to form active visual pigments.

A preferred 9-cis-retinyl ester is 9-cis-retinyl acetate. Also referred to as "9-cis-R—Ac", 9-cis-retinyl acetate is which is metabolized by the liver to fatty acid 9-cis-retinyl esters, such as 9-cis-retinyl palmitate. Fatty acid 9-cis-retinyl esters and retinol are then converted to 9-cis-retinal in the eye and RPE as replacement of deficient chromophores such as 11-cis-retinal.

In one embodiment, 9-cis-R—Ac can be prepared by initially converting all-trans-retinyl acetate (Sigma-Aldrich) to a mixture of 9-cis-retinyl acetate and all-trans-retinyl acetate in the presence of a palladium catalyst (e.g., palladium salts, palladium oxides). The mixture of 9-cis-retinyl acetate and all-trans-retinyl acetate are then hydrolyzed to produce a mixture of 9-cis-retinol and all-trans-retinol. The pure 9-cis-retinol can be isolated by selective recrystallization and further esterified to pure 9-cis-R—Ac. A detailed description of the processes for preparing and purifying 9-cis-R—Ac can be found, for example, in GB Patent No. 1452012.

In certain embodiments, the 9-cis-retinyl esters described herein can be prepared from 9-cis-retinol using appropriate esterifying agents in a manner similar to the preparation of 9-cis-R—Ac, the methods of which are within the knowledge of one skilled in the art.

In certain embodiments, 9- and 11-cis-retinyl esters can be formed by methods known in the art such as, for example, by acid-catalyzed esterification of a retinol with a carboxylic acid, by reaction of an acyl halide with a retinol, by transesterification of a retinyl ester with a carboxylic acid, by reaction of a primary halide with a carboxylate salt of a retinoic acid, by acid-catalyzed reaction of an anhydride with a retinol, or the like. In an exemplary embodiment, 9- and 11-cis-retinyl esters can be formed by acid-catalyzed esterification of a retinol with a carboxylic acid, such as, acetic acid, propionic acid, butyric acid, valeric acid, caproic acid, caprylic acid, pelargonic acid, capric acid, lauric acid, oleic acid, stearic acid, palmitic acid, myristic acid, linoleic acid, succinic acid, fumaric acid or the like. In another exemplary embodiment, retinyl esters can be formed by reaction of an acyl halide with a retinol (see, e.g., Van Hooser et al., Proc. Natl. Acad. Sci. USA, 97:8623-28 (2000)). Suitable acyl halides include, for example, acetyl chloride, palmitoyl chloride, or the like.

In certain embodiments, trans-retinoids can be isomerized to cis-retinoids by exposure to UV light. For example, all-trans-retinal, all-trans-retinol, all-trans-retinyl ester or all-trans-retinoic acid can be isomerized to 9-cis-retinal, 9-cis-retinol, 9-cis-retinyl ester or 9-cis-retinoic acid, respectively. Trans-Retinoids can be isomerized to 9-cis-retinoids by, for example, exposure to a UV light having a wavelength of about 365 nm, and substantially free of shorter wavelengths that cause degradation of cis-retinoids, as further described herein.

In another embodiment of the disclosure, trans-retinoids can be isomerized to cis-retinoids by exposure to UV light. For example, all-trans-retinal, all-trans-retinol, all-trans-retinyl ester or all-trans-retinoic acid can be isomerized to 9-cis-retinal, 9-cis-retinol, 9-cis-retinyl ester or 9-cis-retinoic acid, respectively, by exposure to a UV light having a wavelength of about 365 nm, and substantially free of shorter wavelengths that cause degradation of cis-retinoids, as further described herein.

The synthetic retinal derivative of the disclosure can be substantially pure in that it contains less than about 5% or less than about 1%, or less than about 0.1%, of other retinoids. One or more synthetic retinal derivatives may be used in the therapeutic regimens of the disclosure.

Pharmaceutically Acceptable Compositions of the Disclosure

Synthetic retinal derivatives, including 9- and 11-cis-retinyl esters, of the disclosure can be formulated for oral administration using pharmaceutically acceptable vehicles as well as techniques routinely used in the art. In certain embodiments, the synthetic retinal derivative is formulated into a formulation suitable for oral administration. Most of the synthetic retinal derivatives are oily substances and lipophilic and are therefore easily miscible with one or more lipid vehicles.

Synthetic retinal derivatives, including 9- and 11-cis-retinyl esters, of the disclosure (e.g., 9-cis-retinyl esters) are light- and oxygen-sensitive. It is therefore desirable to maintain the stability and maximize the efficacy and shelf-life of the formulation. A suitable lipid vehicle may be selected based on its ability to stabilize the synthetic retinal derivatives suspended or solubilized therein. As used herein, "lipid" or "lipid vehicle" refers to one or a blend of fatty acid esters. In various embodiments, the lipid vehicle comprises one or more triglycerides, which are formed when a single glycerol is esterified by three fatty acids. Triglycerides include both vegetable oils and animal fats. In various embodiments, the lipid vehicle comprises more than 50 w/w % polyunsaturated fatty acids, the polyunsaturated fatty acids including an omega-6 fatty acid and an omega-3 fatty acid in a ratio (by weight) of less than 15.

In a preferred embodiment, the synthetic retinal derivatives, for example 9- or 11-cis-retinyl esters, are formulated into an oral formulation comprising a retinal derivative, such as a 9- or 11-cis-retinyl ester, and a lipid vehicle. In a further embodiment, the 9- or 11-cis-retinyl ester is 9-cis-retinyl acetate, and the lipid vehicle is soy bean oil. In a further embodiment, the formulation further comprises an antioxidant. In certain such embodiments, the antioxidant is butylated hydroxyanisole (BHA). The description of additional lipid vehicles and formulations suitable for use with the present invention can be found in, for example, International Patent Application No. PCT/US2009/059126 in the name of QLT Inc., the relevant disclosure of which is incorporated herein in its entirety.

The present disclosure also provides kits that contain a synthetic retinal derivative, preferably a 9- or 11-cis-retinyl ester or a pharmaceutically acceptable composition thereof. The kit also includes instructions for the use of the synthetic retinal derivative in the therapeutic regimens and methods of the disclosure. Preferably, a commercial package will contain one or more unit doses of the synthetic retinal derivative, for example, one or more unit doses of a 9- or 11-cis-retinyl ester or the pharmaceutically acceptable composition for use in a therapeutic regimen or method of the disclosure. It will be evident to those of ordinary skill in the art that the synthetic retinal derivative, for example a 9- or 11-cis-retinyl ester or pharmaceutically acceptable compositions thereof which are light and/or air sensitive may require special packaging and/or formulation. For example, packaging may be used for the kit which is opaque to light, and/or sealed from contact with ambient air, and/or formulated with suitable excipients.

Dosage, Dosage Frequency and Modes of Administration

The synthetic retinal derivatives and pharmaceutically acceptable pharmaceutical compositions comprising the synthetic retinal derivatives used in the therapeutic regimens of the disclosure may be in the form of an oral dose. In one embodiment, a pharmaceutically acceptable composition of the disclosure comprising a 9- or 11-cis-retinyl ester and a lipid vehicle is administered orally to the subject in the therapeutic regimen of the disclosure. In another embodiment of the disclosure, the orally-administered pharmaceutically acceptable composition of the disclosure comprises a 9-cis-retinyl ester and soybean oil. In another embodiment of the disclosure, the orally-administered pharmaceutically acceptable composition comprises 9-cis-retinyl acetate or 9-cis-retinyl succinate and soybean oil (USP grade).

Oral administration of the synthetic retinal derivative, for example a 9- or 11-cis-retinyl ester, of the disclosure has several potential advantages, including exposure of all photoreceptors in both eyes of the subject undergoing the therapeutic regimen of the disclosure to therapy, lack of surgical intervention, and cessation of administration at any time. In other embodiments, therapeutic regimens of the disclosure may be used in combination with vector-mediated gene transfer therapy for replacement of one or more genes, for example, RPE65 or LRAT, associated with the visual cycle in a subject, for example in subjects who have already received gene therapy as a method for treating or ameliorating visual disorders associated with endogenous retinoid deficiency in a subject.

The therapeutic regimens of the present disclosure produce meaningful improvement of visual function, while exhibiting an acceptable safety profile, in, and thus in one embodiment, the therapeutic regimens of the present disclosure may be suitable as a long-term (chronic) therapeutic regimen.

The length of the resting period of time between the first therapeutic dose and the second therapeutic dose is less than one month, such as from 7 to 28 days, and may be optionally selected be based on the persistence or increase in one or more of the subject's visual function parameters, as defined herein during the less than one month resting period. Dosing-dependent effects or improvement in the subject's visual functions may be observed and assessed on an individual basis to allow for customization of the subject's dosing requirements within the less than one month resting period. Alternatively, administration of a second therapeutic dose may be based on a decrease in one or more of the subject's visual function parameters relative to previous efficacy assessments during a first dosing period and any resting period. For instance, the efficacy of the subject's dosing may be assessed at, for example, about 3 days, 4 days, 5 days, 6 days, 7 days, 8 days, 9 days, 10 days, 11 days, 12 days, 13 days, 14 days, 15 days, 16 days, 17 days, 18 days, 19 days, 20 days or 21 days following the first therapeutic dose. At any point of the assessment, a subsequent therapeutic dose may be administered based on a regression of one or more of the subject's visual function parameters during any resting period.

In some embodiments, the clinically relevant safety profile in combination with a plurality of therapeutic dosing periods and resting periods is established. In some embodiments, up to 6, up to 5, up to 4, or up to 3 therapeutic doses are administered in up to 6 months, up to 5 months, up to 4 months or up to 3 months. In some embodiments, up to 12, up to 11, up to 10, up to 9, up to 8, up to 7, up to 6, up to 5, up to 4, or up to 3 therapeutic doses are administered to a subject in up to 12 months, up to 11 months, up to 10 months, up to 9 months, up to 8 months, up to 7 months, up to 6 months, up to 5 months, up to 4 months, or up to 3 months. In another embodiment, up to 3 therapeutic doses are administered in about 3 months. In another embodiment, up to 6 therapeutic doses are administered in about 6 months. In certain instances of the foregoing, no more than one therapeutic dose is administered per month.

In some embodiments, the therapeutic regimens and methods established for an RP subject may be applied to an LCA subject.

Following oral administration of the composition, without wishing to be bound by any particular theory, it is believed that the drug is incorporated into lipid droplets in the liver and in the RPE (called retinosomes) from which it is mobilized. Imanishi Y. et al. J Cell Biol 166:447-53 (2004). It is secreted by the liver bound to retinol binding-protein 4 (RBP4) and delivered to peripheral tissues, whereas in the eye it is oxidized to 9-cis-retinal which feeds back into the retinoid cycle (FIG. 1). Moise A. R. et al. Biochemistry 46:4449-58 (2007). Retinols, regardless of their isomeric form, are also stored in adipocytes and mobilized as needed into the circulation. O'Byrne S. M. et al. J Biol Chem 280:35647-57(2005). Thus, the long-term effects of this chromophore analog may derive from the fact that active drug is slowly released from adipocytes in the periphery.

Evaluation of Therapeutic Effect

The effectiveness of the therapeutic regimens of the disclosure in improving visual function in a subject with RP or LCA or with other visual disorders associated with an endogenous retinoid deficiency, can be evaluated based on several measures of vision function, including those as described below.

Improvements in the subject's visual functions in one or both eyes may be evaluated based on measures of visual field, visual acuity, and retinal sensitivity testing, as well as electroretinograms, dynamic pupillary response, nystagmus, cortical visual function, color vision, visual mobility testing, and patient-reported outcomes of quality of life/ability to perform life tasks. The degree of retinal and photoreceptor degeneration can be further evaluated by optical coherence topography (OCT) and fundus autofluorescence (FAF) analysis at baseline and post-treatment. Improvements in the subject's visual functions in one or both eyes during a therapeutic regimen of the disclosure can be demonstrated by comparing the subject's visual functions of each eye with a baseline measure of the subject's visual functions of each eye prior to administration of a therapeutic regimen of the disclosure or by comparing the subject's visual functions of each eye with a comparable human visual system not receiving the therapeutic regimen.

1. Visual Field

Progressive visual field loss is one of the hallmarks of endogenous retinoid deficiencies, for example RP and LCA, and is commonly used as a means to monitor the progression of the disease. For example, it has been reported that most RP subjects are legally blind because of severely constricted visual fields.

Visual field is an individual's entire scope of vision, including the central and peripheral (side) vision of each eye. Normal human visual field extends to approximately 60 degrees nasally (toward the nose, or inward) in each eye, to 100 degrees temporally (away from the nose, or outwards), and approximately 60 degrees above and 75 below the horizontal meridian.

Visual field can be tested by art-recognized techniques and standards, such as Kinetic Perimetry by Goldmann Visual Field testing (GVF), Fundus Controlled Perimetry (Microperimetry—MP1), or Static Perimetry by Humphrey Visual Field Analyzer (HFA). GVF as generally measured on a standard calibrated Goldmann perimeter. Fields are measured by moving a stimulus (isopter or target) from nonseeing to seeing regions, thereby generating a map of peripheral visual field locations. Due to planimetric distortion in the testing procedure, GVF chart results may be digitized and converted to retinal surface area to most accurately capture changes in the peripheral VF in subjects with retinal degeneration. Baseline measures may be used to identify one VF isopter which provided a VF log retinal area closest to the midpoint 1.5 log mm$^2$ of the 0.7 to 2.4 log mm$^2$ range, for assessment of VF over time. Changes in log retinal area of the selected isopter size may be assessed using a mixed effects model which uses the log retinal area from each eye. Correlation and extent of the correlation between the two eyes of the same subject were accounted for in the analysis. Improvements in visual field of greater than 20% are accepted as clinically significant improvements based on evaluation of test-retest variability (Bittner et al., IOVS 52:8042-8046 (2011)). VF may also be calculated as a solid angle measure in steradians, as a volume measure, combining the results of 2 or more isopters, or as an approximate Hill of Vision for 3 or more sequential isopters by finding the volume of the stacked isopters (Christoforidis, Clin. Ophthalmol., 5: 535-541 (2011)). Changes in visual field calculated by any method may be determined by comparison to the subject's baseline measures.

Subjects having the endogenous retinoid deficiencies described herein may have various degrees of impairments that can span from non-detectable to significantly contracted visual field. For example, identifiable, distinctive patterns of VF loss in RP subjects has been defined (Grover et al., Ophthalmology 105:1069-1075 (1998)). Typical, less advanced RP may demonstrate a VF>20 degrees detectable with the V4e target. Atypical RP may demonstrate large VF>20 degrees with V4e and reduced central sensitivity. These RP subjects only detect the V4e in the macula/foveally. Typical RP subjects with advanced degeneration may demonstrate small VF<20 degrees with V4e, or small VF<20 with V4e and reduced central sensitivity, with detection of V4e target only in the macula/foveally.

In one embodiment of the therapeutic regimens of the invention, the subject's visual field improves in the dosing period as compared to the baseline of the subject's visual field obtained prior to the dosing period. In certain embodiments, the subject's visual field continues to improve during the resting period as compared to the improvement in the subject's visual field during the dosing period. In certain embodiments, the improvement in the subject's visual field observed during the initial dosing period is sustained at a level above the subject's baseline visual field during the resting period. In another embodiment, the improvement in the subject's visual field improves during the dosing and/or resting period, but returns to about baseline by the end of the resting period.

In various embodiments of the present invention, for example for RP subjects with LRAT or RPE65 mutation, including without limitation, arRP patients, the subject's visual field may expand by at least 20 degrees, of the baseline retinal area.

Commencement of a subsequent dosing period may begin upon assessment of the improvement of the subject's visual field during the initial dosing period and during the resting period. For example, the subsequent dosing period may commence if the subject's visual field returns to a level prior to the initial dosing period or to a pre-determined level during the initial resting period. In one embodiment, a subsequent dosing period may begin upon assessment of an improvement of <20% from baseline of the subject's visual field after the initial dosing period.

2. Visual Acuity

Decline in visual acuity (VA) can be noted during the course of RP or other visual disorders associated with an endogenous retinoid deficiency, including LCA. Subjects with early-onset RP have been shown to have more stable VA than other RP types. VA can remain normal even in individuals with advanced RP with a small island of remaining central VF, although decrease in VA can be also observed in some RP subjects.

Visual acuity refers to acuteness or clearness of vision, especially form vision, which is dependent on the sharpness of the retinal focus within the eye and the sensitivity of the interpretative faculty of the brain. Visual acuity is a measure of the spatial resolution of the visual processing system and is usually tested in a manner to optimize and standardize the conditions.

LogMAR charts, particularly the Early Treatment Diabetic Retinopathy Study (ETDRS) charts have become the gold-standard for measuring treatment effects on VA in clinical trials. Protocols are well established such that subjects able to read less than 20 letters at 4 meters are tested at 1 meter. This method measures vision under high contrast and standard room lighting conditions. The Smith-Kettlewell Institute Low Luminance (SKILL) Chart was designed to assess vision under conditions of low contrast that simulates low lighting, through a test performed with standard indoor lighting. The SKILL Chart has a high-contrast near-acuity chart on one side (black letter on white), and a low-luminance, low-contrast chart on the other (gray letters on a dark background). The low reflectance of the dark side of the card simulates testing in a dim environment.

In certain embodiments of the present invention, the degree of improvement in visual acuity over baseline may be dependent on the subject's baseline visual acuity. For patients with very low visual acuity (light perception or hand waving, zero letters), clinically meaningful improvement may be associated with an improvement of 1-5 ETDRS letters. In certain embodiments, the subject may have a VA improvement of ≥5 ETDRS letters upon administration of a first therapeutic dose. In certain embodiments, the subject may have a VA improvement of ≥5 to <10 upon administration of a first therapeutic dose. In certain embodiments, the subject may have a VA improvement of ≥10 to <15 letters upon administration of a first therapeutic dose. In certain embodiments, the subject may have VA improvements of ≥15 to <20 letters upon administration of a first therapeutic dose. In certain embodiments, the subject may have VA improvements of ≥20 letters upon administration of a first therapeutic dose. Thus, in one embodiment of the therapeutic regimens of the invention, the subject's visual acuity improves during the initial dosing period as compared to the subject's visual acuity level prior to the treatment during the initial dosing period, i.e, the subject's visual acuity baseline. In certain embodiments, the subject's visual acuity continues to improve during the resting period as compared to the improvement in the subject's visual acuity level observed at the end of the initial dosing period. In certain embodiments, the improvement in the subject's visual acuity is sustained above the subject's baseline level during the resting period.

In one embodiment, a subsequent dosing period may begin upon assessment of an improvement of <5 letters from baseline, for subjects with a baseline VA>0 letters, of the subject's visual acuity after the initial dosing period.

3. Retinal Sensitivity

A subject's retinal sensitivity can be measured by determining the absolute intensity threshold, that is, the minimum luminance of a test spot required to produce a visual sensation. Retinal sensitivity is related to the eye's ability to adjust to various levels of darkness and light and to detect contrast.

Full-field stimulus testing (FST) was developed to measure dark-adapted sensitivity using commercial equipment in patients unable to fixate (Roman, A. J. et al., Physiol. Meas. 28(8):N51-N56 (2007)). The test uses a full-field (Ganzfeld) white-flash stimulus presentation available in a commercial ERG dome (Diagnosys) and available software allows for reliable, efficient psycho-physical measures of absolute threshold, expressed in log luminance (log cd/m2). FST may also be performed using light stimuli delivered with a Colordome Ganzfeld stimulator (Diagnosys LLC, Littleton, Mass.). In this test method, repeated measurements of sensitivity to a full-field stimulus are obtained in the dark-adapted state with white, red and blue flashes.

Two color threshold perimetry has been previously described (Lorenz et al., Invest Ophthal Vis Sci. 49(12): 5235-5242 (2008)). To assess the spatial distribution of rod- and cone-mediated function, 2-colour threshold perimetry is performed under scotopic and photopic conditions. A modified Humphrey field analyzer or equivalent may be used. The scoptopic thresholds are measured after dark adaptation. The sensitivity loss may be calculated as the difference between the measured value in the subject and the 10th percentile of normal subjects for each test locus. Photopic thresholds are measured with a background illumination of 10 cd/m$^2$. Cone sensitivity may be calculated as the difference between the measured value to the long wavelength stimulus and the 10th percentile of normal subjects for each test locus.

Dark adapted static perimetry measures dark-adapted (including extended dark adaptation of up to 6 hours or longer) threshold sensitivity in subjects, at a range of individual loci throughout the visual field area, which is particularly useful in subjects unable to fixate. The test utilizes the full-field stimulus presentation available in Goldmann perimeter or the commercial ColorDome, which can present flashes as bright as 4.5 log troland-seconds.

FST has previously been shown to measure rod and cone sensitivity to white, blue, and red stimuli in RPE65-deficient LCA patients who had limited or no ERG responses (Jacobson, S. G. et al., Invest Ophthalmol Vis Sci. 50(5):2368-2375 (2009)). Dark-adapted static perimetry methods may be used to more accurately identify residual vision in the visual field of these subjects. Optimization of retinal sensitivity assessments relevant for subjects with RPE65 gene mutations has been performed previously (Cideciyan, A. V. et al., Proc Natl Acad Sci USA. 105(39): 15112-15117). Thus, in one embodiment of the therapeutic regimens of the invention, the subject's retinal sensitivity improves during the initial dosing period as compared to the subject's retinal sensitivity baseline prior to the treatment during the initial dosing period. In certain embodiments, the subject's retinal sensitivity continues to improve during the resting period as compared to the improvement in the subject's retinal sensitivity at the end of the initial dosing period. In certain embodiments, the improvement in the subject's retinal sensitivity is sustained during the resting period at about the subject's retinal sensitivity level at the end of the initial dosing period. In certain embodiments, the improvement in the subject's retinal sensitivity is sustained at a level above the subject's baseline retinal sensitivity during the resting period.

4. Electroretinograms (ERG)

ERG testing is a well-accepted standard test and is used routinely to diagnose and monitor progression of most inherited retinal diseases (IRD), including visual disorders associated with an endogenous retinoid deficiency. Physicians specializing in IRD agree that significant, repeatable improvements in ERG responses are indicative of improved visual function. For example, ERG responses are an early indicator of loss of rod and cone function in RP and a decrease in ERG response can be evident within the first few years of life, even though symptoms appear much later. It has been reported that RP patients have decreased or undetectable rod and cone responses, typically with a greater loss of rod than cone ERG responses.

The three main types of traditional global or full-field ERG that evaluate general retinal response are scotopic (dark adapted, dim flash, rod-mediated ERG), photopic (light adapted, bright flash, con-mediated ERG), and flicker (light adapted, bright flash, 31-Hertz Flicker ERG) testing. Dark adapted, bright flash, rod/cone-mediated ERG may also be evaluated. A limitation of full-field ERG is that the recording is a massed potential from the whole retina. Unless 20% or more of the retina is affected with a diseased state, ERG recordings are usually normal (e.g., a legally blind person with macular degeneration, enlarged blind spot or other central scotomas may have normal global ERGs). Early-onset RP is generally defined as demonstrating an extinguished or markedly reduced ERG response typical of a rod-cone degeneration before the age of 6 years.

In one embodiment of the therapeutic regimens of the invention, the subject's ERG response improves during the initial dosing period as compared to the subject's ERG response prior to the treatment during the initial dosing period. In certain embodiments, the subject's ERG response continues to improve during the resting period as compared to the improvement in the subject's ERG response observed at the end of the initial dosing period. In certain embodiments, the improvement in the subject's ERG response is sustained above the subject's baseline level during the resting period.

5. Dynamic Pupillary Response (Pupillometry)

Pupillary responses (constriction of the pupil in response to a bright light stimulus) may be abnormal in subjects having a visual disorder as described herein. Dynamic pupillometry is a non-invasive method to record the pupillary response and monitor potential changes in response to treatment. Pupillary reflexes improved in LCA subjects with RPE65 deficiency after receiving gene therapy (Maguire, A. M. et al., New Engl J Med. 358:2240-2248 (2008)). Chromatic pupillometry, in which light stimuli of varying color, intensity, stimulus duration and time between stimuli, has been established (Park et al., Invest Ophthal Vis Sci. 52(9): 6624-6635 (2011)), with light delivered with a Colordome Ganzfeld stimulator (Diagnosys LLC, Littleton, Mass.) or equivalent. The examination for rod-weighted recordings and the intrinsic photosensitive retinal ganglion cell recordings are performed after dark adaptation. Video signals of the recordings may be relayed to a processing board that records the pupil diameter in real time into a text file. Relative sustained and transient pupil constriction data are analyzed for clinical significance.

Thus, in one embodiment of the therapeutic regimens of the invention, the subject's pupillary response improves during the initial dosing period as compared to the subject's pupillary response baseline level prior to the treatment during the initial dosing period. In certain embodiments, the subject's pupillary response continues to improve during the resting period as compared to the subject's pupillary response level at the end of the initial dosing period. In certain embodiments, the improvement in the subject's pupillary response is sustained during the resting period at about the subject's pupillary response level at the end of the initial dosing period. In certain embodiments, the improvement in the subject's pupillary response is sustained at a level above the subject's baseline pupillary response during the resting period.

6. Nystagmus

Nystagmus is a form of involuntary eye movement that is frequently associated with visual impairment, including LCA. Nystagmus amplitude and frequency is measured non-invasively and can be used to monitor potential changes in response to treatment such as by videotaping the eye movements for qualitative clinical analysis of the subject's oscillation and strabismus. (Maguire, A. M. et al., New Engl J Med. 358:2240-2248 (2008)).

Thus, in one embodiment of the therapeutic regimens of the invention, the subject demonstrates a decrease in the amplitude and/or frequency of nystagmus during the initial dosing period. In another embodiment, the subject demonstrates a continued decrease in the amplitude and/or frequency of nystagmus during the resting period.

7. Visual Cortical Function

The therapeutic effectiveness of the therapeutic regimens of the invention may be monitored using effects of the subject's vision on cortical visual function as measured by functional magnetic resonance imaging (fMRI). Functional scans consist of a contrast sensitivity challenge, movement stimulus challenge, and higher level cognitive challenges.

Data are normally displayed as percentage change in MRI signal from baseline. Maps of statistical significance will be displayed on the reconstructed cortical surface from each individual. The pre- and post-treatment scans will be directly compared in terms of the extent and magnitude of activation. Improvement in visual cortical function may be defined based on activation of the visual and/or parietal cerebral cortex.

Thus, in one embodiment of the therapeutic regimens of the invention, the subject's cortical vision function improves during the initial dosing period as compared to the subject's cortical vision function baseline level prior to the treatment during the initial dosing period. In certain embodiments, the subject's cortical vision function continues to improve during the resting period as compared to the subject's cortical vision function level at the end of the initial dosing period. In certain embodiments, the improvement in the subject's cortical vision function is sustained during the resting period at about the subject's cortical vision function level at the end of the initial dosing period. In certain embodiments, the improvement in the subject's visual cortical function is defined by activation of the visual cerebral cortex after treatment. In certain embodiments, the improvement in the subject's visual cortical function is defined by activation of the parietal cortex after treatment.

8. Color Vision

A color vision test checks a subject's ability to distinguish between different colors. Ishihara plates are used to detect, classify and estimate the degree of defect in color vision. Color vision testing is also used to evaluate the function of the optic nerve and hereditary retinal disease.

Color vision may be assessed by methods known in the art, including the Ishihara Color Test, Hardy-Rand-Rittler, or Farnsworth-Munsell 100 Hue test. The test consists of a number of colored plates, each of which contains a circle of dots appearing randomized in color and size. Within the pattern are dots which form a number visible to those with normal color vision.

Thus, in one embodiment of the therapeutic regimens of the invention, the subject's color vision improves during the initial dosing period as compared to the subject's color vision baseline level prior to the treatment during the initial dosing period. In certain embodiments, the subject's color vision continues to improve during resting period as compared to the subject's color vision level at the end of the initial dosing period. In certain embodiments, the improvement in the subject's color vision is sustained during the resting period at about the subject's color vision level at the end of the initial dosing period.

9. Dark Adaptation

Dark adaptation is defined as the recovery of light sensitivity by the retina in the dark after exposure to a bright light. Impairment in dark adaptation rates is associated with a range of visual disease states, and is often an early symptom for RP subjects. Dark adaptation parameters include, but are not limited to, the time constant of the cone-mediated sensitivity recovery, the time constant of rod-mediated sensitivity recovery, the cone plateau, the rod plateau, the rod-cone break, the rod intercept, the slope and/or time constant of the second component of the rod-mediated recovery, the slope and/or time constant of the third component of the rod-mediated recovery, the transition time between the second and third rod-mediated components, and the duration from the bleaching to the final threshold measurement.

Methods to measure dark adaptation are known in the art, including those methods defined in U.S. Pat. Nos. 7,494,222 and 7,798,646, the contents of which are herein incorporated by reference.

Improvements in the rate of dark adaptation may be determined based on a comparison of a subject's rate of dark adaptation after treatment as compared to the subject's baseline rate. Treatment effects on dark adaptation may also be monitored using subjective, patient reported outcomes, which document improvements in activities of daily living related to the rate of a subject's vision to dark-adapt when transitioning from light to dark environments.

In one embodiment of the therapeutic regimens of the invention, the subject's rate of dark adaptation improves during the initial dosing period as compared to the subject's rate of dark adaptation at baseline. In certain embodiments, the subject's rate of dark adaptation continues to improve during the resting period as compared to the subject's rate of dark adaptation at the end of the initial dosing period. In certain embodiments, the improvement in the subject's rate of dark adaptation is sustained during the resting period at about the subject's rate of dark adaptation at the end of the initial dosing period. In certain embodiments, the improvement in the subject's rate of dark adaptation is sustained at a level above the subject's baseline rate of dark adaptation during the resting period.

10. Visual Mobility

Visual mobility may be used as a measure of improved retinal function. Improvements in visual mobility can be determined by methods known in the art, including standardized obstacle courses and mazes, including those described in Bainbridge et al. N Engl J Med. 358:2231-9 (2008) and Maguire, A. M. et al., New Engl J Med. 358: 2240-2248 (2008). Subjects may be assessed based on the time to navigate the course, or based on the number of times a subject bumps into obstacles or walks off course compared to the total number of obstacles present.

Visual mobility may also be monitored based on subjective, patient reported outcomes. Subjective reports of improvement in mobility may be used to monitor treatment effects through comparison on a subject's reported mobility after treatment and during the resting period, as compared to the subject's reported mobility at baseline.

11. Visual Function Questionnaires

Questionnaires may be administered to subjects at certain study visits to assess visual function and its effects on activities of daily living. There are a number of known Visual Function Questionnaires (VFQ's) which may be used to assess improvement in a subject's visual function. One such questionnaire is the Children's Visual Function Questionnaire (CVFQ) (see, e.g., Birch, E. E. et al., J. AAPOS. 11:473-9 (2007)). This is a vision-specific quality-of-life instrument designed for use with parents of infants and young children.

The Low Luminance Questionnaire (LLQ) is a questionnaire that has been developed specifically to assess visual performance of adults in low lighting conditions, such as night-time or darkened rooms (see, e.g., Owsley, C. et al., Invest Ophthalmol Vis Sci 47:528-535 (2006). This questionnaire was validated in a population of older RP subjects similar to the population eligible for the clinical study described below and correlates to rod-mediated parameters of dark adaptation.

The Impact of Vision Impairment (IVI) questionnaire and the Impact of Vision Impairment for Children (IVI_C) questionnaire may also be used. These questionnaires were developed and validated to measure the impact of vision impairment on restriction of participation in daily activities in people with low vision.

The use of the VFQ's assists in identifying subjective improvements in visual function, particularly with respect to activities of daily life following administration of a compound of the invention by the therapeutic regimens described herein through comparison of the subject's questionnaire results after treatment and during the resting period as compared to the subject's questionnaire results at baseline.

12. Spectral Domain-Optical Coherence Tomography

Optical coherence tomography (OCT)/autofluorescence (FAF) machines, such as the Heidelberg Spectralis (Heidelberg Engineering, Germany), may be used to conduct ocular tomography scans. The analyses of the scans may provide information as to the overall retinal health, including visualization of the photoreceptor layer, the outer segments, and measurement of retinal thickness and to assess presence or absence of autofluorescence. Improvement in retinal health may be assessed by comparing a subject's baseline OCT and FAF scans with a subject's OCT and FAF scan after the initial dosing period. A subject's baseline OCT and FAF scans may be correlated to the subject's visual function before and after the initial dosing period.

The following examples are provided merely as illustrative of various aspects of the disclosure and shall not be construed to limit the disclosure in any way.

EXAMPLES

Example 1: Safety Study

An open-label, repeat dose escalation study of an orally-delivered pharmaceutically acceptable composition of the disclosure was conducted in twenty (20) healthy human volunteers to determine the safety and tolerability of repeat daily oral doses of a composition comprising 9-cis-retinyl acetate ((2E, 4E, 6Z, 8E)-3,7-dimethyl-9-(2,6,6-trimethyl-cyclohex-1-en-1-yl) nona-2,4,6,8-tetraen-1-yl acetate) and butylated hydroxyanisole (BHA) dissolved in soybean oil (USP). The concentration of 9-cis-retinyl acetate in the composition was adjusted such that the volume to be administered was convenient. For the dosing range of the study, compositions of 1.25 mg/mL, 5.0 mg/mL and 20 mg/mL 9-cis-retinyl acetate were prepared, containing 0.10% w/w BHA in Soybean oil (USP). Six dose cohorts of healthy subjects received escalating daily doses of the composition orally from 1.25 mg/m$^2$ up to 40 mg/m$^2$, i.e., 1.25, 2.5, 5, 10, 20 and 40 mg/m$^2$.

Eighteen subjects received all 7 days of treatment with the study composition, and 2 subjects had missed doses. The mean average age of subjects was 37 years (range (23-59).

The compositions up to 40 mg/m$^2$ were found to be well tolerated and there were no serious adverse events after 7 days of monitored therapy in a Phase I testing center. The most frequently reported side effects were headache (6 subjects, 12 events), facial flushing (2 subjects, 7 events), and a facial burning sensation (2 subjects, 6 events), which were primarily reported from the 40 mg/m$^2$ dose group and collectively accounted for 25 of the 43 (58%) adverse events (AE) reported. In total, 41 of 43 AEs were of mild intensity.

In some subjects, there was a modest, reversible elevation in triglycerides across all doses and a modest reversible decline in high density lipoproteins (HDL) at the 10-40 mg/m$^2$ doses.

Example 2: Study in RP Patients

Study Protocol

A study was designed to determine the efficacy of the composition of Example 1 orally administered to human RP subjects having RP caused by mutations in either LRAT or RPE65 (also known as early-onset RP). Seventeen RP subjects received a once-daily dose of the composition orally (40 mg/m$^2$) for 7 days. Both eyes of each RP subject were evaluated separately. Protocol-defined assessments of visual function included: best-corrected visual acuity testing using Early Treatment Diabetic Retinopathy Study (ET-DRS), visual field testing, full-field electroretinogram (ERG); retinal sensitivity (FST), dynamic pupillometry, nystagmus testing, OCT and FAF, and subject questionnaire.

Baseline visual function tests were performed, within 21 days of Day 0 of the study, including spectral-domain OCT in low light conditions to determine if there were viable photoreceptors in the retina. On Day 0 each RP subject received the first dose of the composition. Treatment was administered on 7 consecutive days (Day 0 to 6, inclusive). RP subjects had follow-up visits on days 7/8, 14/15, 30, 60 and bimonthly thereafter until retreatment criteria are met. All visual function tests and safety assessments were done on Day 7/8 (24/48 hours after receiving the last dose) as well as on all subsequent visits.

Initial and Preliminary Efficacy Assessment for Two RP Patients

The efficacy of the composition of Example 1 was initially tested in two human subjects having RP. The two subjects received a once-daily initial dose of the Composition (40 mg/m2) for 7 days. Subjects were treated on an outpatient basis, but received study treatment in the research clinic under medical supervision for each day of treatment. During the study, subjects were required to limit vigorous physical activity (to avoid laboratory variability) and avoid excessive vitamin A intake in order to reduce the influence of such factors on the assessment of safety variables in this study.

Both eyes of each subject were evaluated separately. Protocol-defined assessments of visual function included: best-corrected visual acuity testing using Early Treatment Diabetic Retinopathy Study (ETDRS) testing followed by low/high contrast Smith-Kettlewell Institute Low Luminance (SKILL) charts; visual field testing using Goldmann perimetry; full-field electroretinogram (ERG); and full-field stimulus threshold testing (FST). Baseline ERGs, ETDRS, and SKILL tests were repeated twice. During and after treatment, visual function tests were conducted on Day 1, 7, 9/10, and 14/15.

There was no requirement that the subjects wear eye patch on one or both eyes

Subject ID 010110 was a 27-year-old male with RP homozygous mutations in the LRAT gene at c.525T>A; p.Ser175Arg. His ETDRS visual acuity at baseline was 71 letters OD and 60 letters OS (approximately 20/40 and 20/62.5 Snellen equivalent) unaided.

The subject was treated with 40 mg/m$^2$ of Composition A for 7 days. Small improvements in ETDRS visual acuity were observed, with the highest improvement from baseline of 11.5 letters (OD) at Day 9, and 14.5 letters OS at Month 1.5. Large improvements in GVF OD were detected, and supported by subjective reports of improvements in peripheral vision. Objective testing of cortical visual function before and after drug treatment was tested using fMRI, with marked improvements observed. No changes in cone or rod ERG were seen.

The subject reported meaningful improvements in activities of daily living. Sensitivity to daylight and fluorescent lights was noted. Dark adaptation times were also improved. The patient was monitored for 1.5 months beyond the end of the treatment period, with improvements from baseline persisting.

Subject ID 010111 was a 41 year old male with homozygous mutations in the LRAT gene at c.181T>A3; P.TYR61ASP. His ETDRS visual acuity at baseline was 0 letters OD and 1.5 letters OS. The subject was treated with 40 mg/m$^2$ of Composition A for 7 days. Changes in ETDRS visual acuity were observed in one eye, with the highest improvement from baseline of 24.5 letters (OD) and 0 change (OS) at Day 14.

Interim 30 Day Safety and Efficacy Assessments for 17 RP Patients

A total of 17 RP subjects ranging in age from 6 to 55 years, mean 29 years with either RPE65 (12 RP subjects) or LRAT (5 RP subjects) mutations were evaluated with baseline VA and GVF values described in Table 1. Both eyes in each RP subject were evaluated independently. Visual Acuity (VA; ETDRS BCVA) ranged from 0-62 letters for the left eye (OS) with a mean of 29.5 letters (~20/250) and ranged from 0-71 letters for the right eye (OD) with a mean of 32.1 letters (~20/200). Visual Field (GVF) ranged from 0.28-2.46 for the left eye with a mean, log retinal area of 1.7 and ranged from 0.48-2.53 for the right eye with a mean, log retinal area of 1.8.

TABLE 1

| Subject | Age | Sex | Race | Gene | VA OD | VA OS | GVF log retinal area OD | GVF log retinal area OS |
|---|---|---|---|---|---|---|---|---|
| 010110 | 28 | M | Asian | LRAT | 70.5 | 59.5 | 1.62 | 1.41 |
| 010111 | 41 | M | White | LRAT | 0 | 1.5 | 2.47 | 2.48 |
| 010117 | 6 | M | Asian | LRAT | 37 | 39.5 | 2.42 | 2.40 |
| 010118 | 11 | M | Asian | RPE65 | 40.5 | 19 | 1.04 | 0.28 |
| 010201 | 30 | M | White | RPE65 | 64 | 51 | 2.16 | 1.93 |
| 010202 | 20 | F | White | LRAT | 60.5 | 40 | 1.53 | 1.40 |
| 010301 | 37 | M | Asian | RPE65 | 13.5 | 22 | 1.91 | 1.74 |
| 010302 | 55 | F | White | LRAT | 53 | 27.5 | 2.16 | 2.08 |
| 010303 | 29 | M | Asian | RPE65 | 63.5 | 59 | 2.31 | 2.31 |
| 010304 | 36 | F | Asian | RPE65 | 11.5 | 11.5 | 1.56 | 1.74 |
| 010401 | 28 | F | White | RPE65 | 0 | 0 | 0.48 | 0.42 |
| 010402 | 30 | F | White | RPE65 | 39 | 10.5 | 1.09 | 1.77 |
| 010403 | 21 | F | White | RPE65 | 23 | 50 | 1.39 | 1.42 |
| 010501 | 40 | M | White | RPE65 | 11 | 3 | 2.11 | 1.88 |
| 010502 | 24 | F | White | RPE65 | 33 | 29.5 | 2.76 | 1.55 |
| 010601 | 21 | M | White | RPE65 | 8 | 16.5 | 2.00 | 2.24 |
| 010701 | 23 | M | Hispanic | RPE65 | 17 | 61.5 | 1.83 | 1.73 |

At baseline, a total of 13 of the 17 RP subjects reported night blindness with the majority of RP subjects listing night blindness as the first symptom of RP: 5 RP subjects within the first year of life, 3 RP subjects within 2-4 years of age, 1 RP subject at 17 years of age. Visual field loss was reported in 11 of the 17 RP subjects, while 12 of 17 RP subjects reported visual acuity deterioration.

GVF analysis was performed on two data sets. Intent to treat (ITT) including all 17 RP subjects, and the Evaluable (per Protocol) set which included RP subjects who fulfilled major inclusion/exclusion criteria. For each RP subject, the two baseline measures were used to identify one VF target which provided a VF log retinal area closest to the midpoint 1.5 log mm$^2$ of the 0.7 to 2.4 log mm$^2$ range, to allow for assessment of changes in VF over time. Changes in log retinal area of the selected target size were assessed using a mixed effects model which uses the log retinal area from each eye. Correlation and extent of the correlation between the two eyes of the same RP subject were accounted for in the analysis. GVF responders were defined as eyes with at least 20% improvement in VF compared to their baseline measure.

Three distinct visual field patterns were observed across the 17 RP subjects in this study. 1. Typical RP, less advanced (9 RP subjects) demonstrated VF>20 degrees detectable with the V4e target. This pattern was similar to VF baselines for LCA subjects. Mean age was 20.9 years (range 6-30 years). 2. Atypical RP (3 RP subjects, same RPE65 mutations—c, 179; pLeu60Pro homo): large VF>20 degrees with V4e and reduced central sensitivity. These RP subjects could only detect the V4e in the macula/foveally. Mean age was 34.5 years (range 29-37 years). 3. Typical RP/Advanced degeneration: small VF<20 degrees with V4e, or small Vf<20 with V4e and reduced central sensitivity, only detecting the V4e target in macula/foveally. Mean age was 39.2 years (range 28-55 years).

Figure 2:
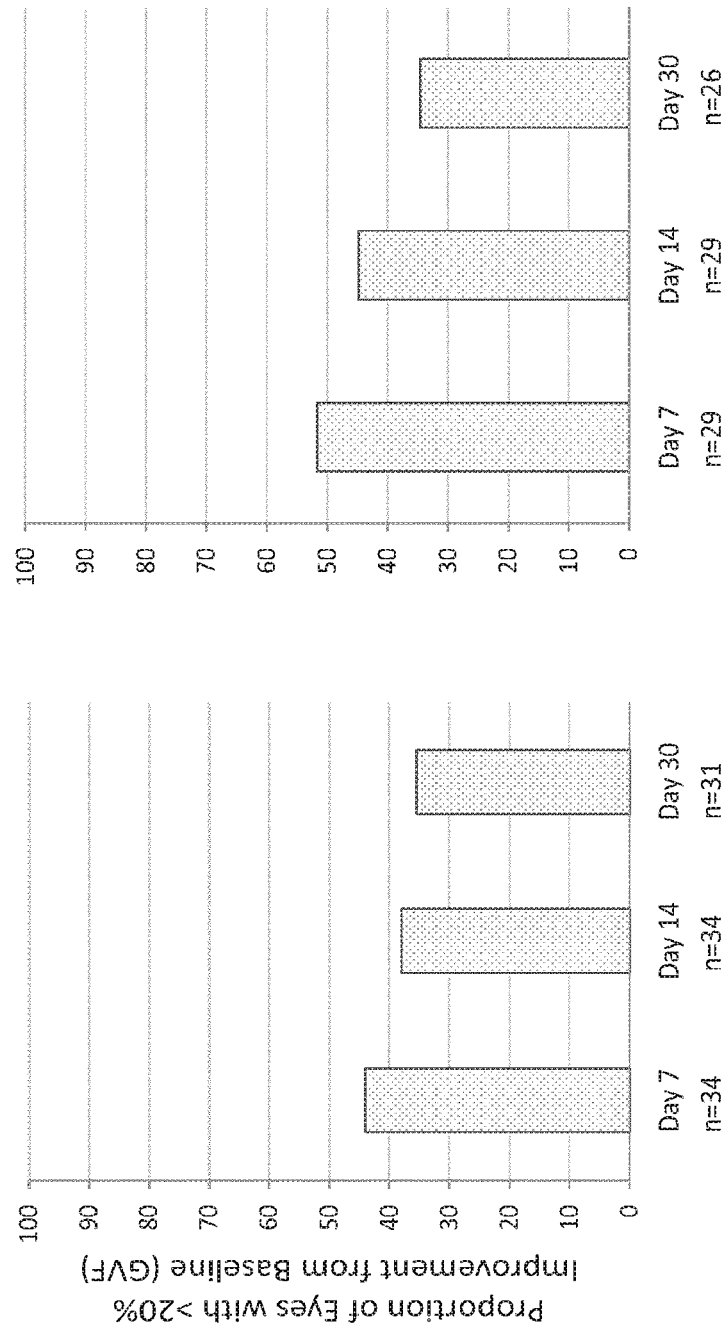
Figure 3:
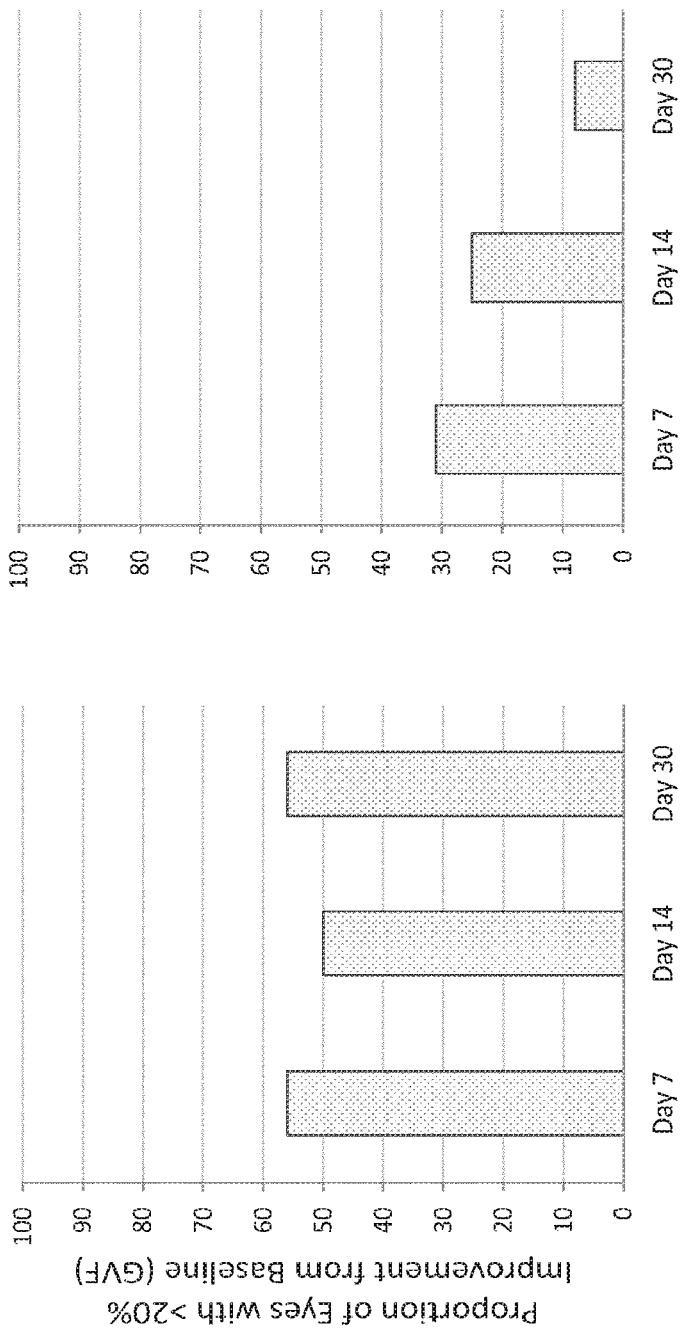
Figure 4:
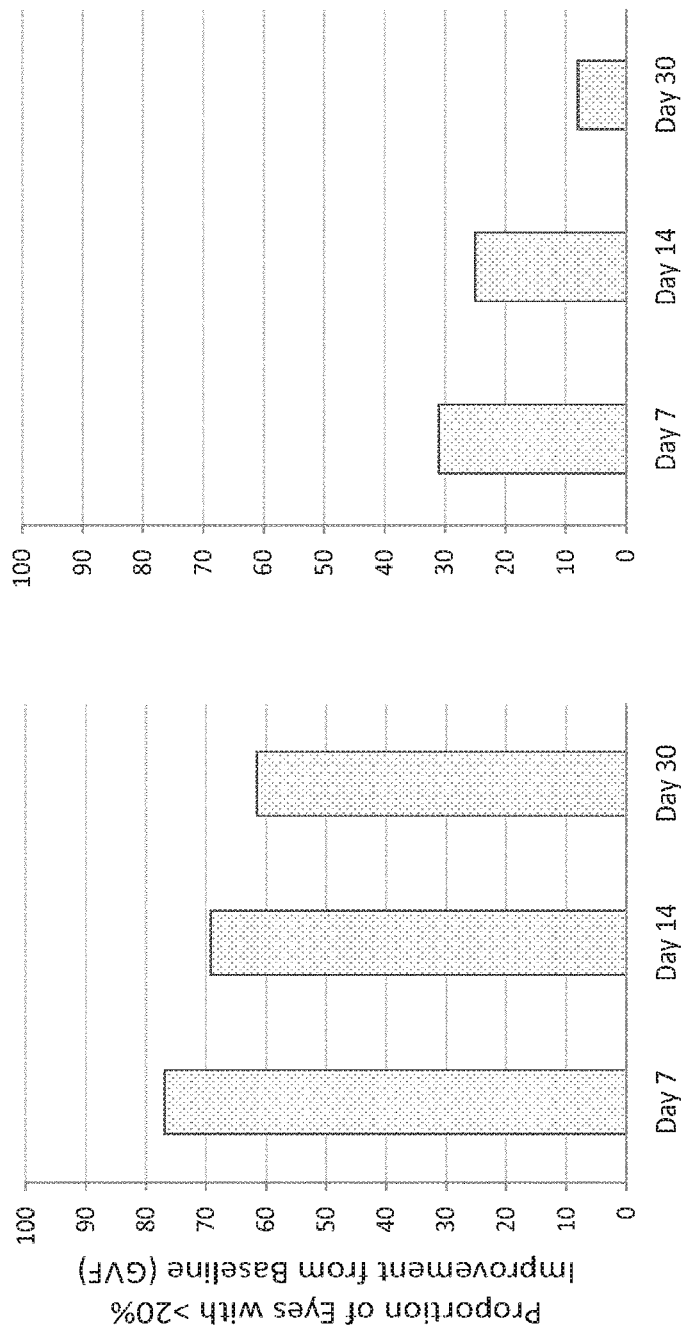
Figure 5:
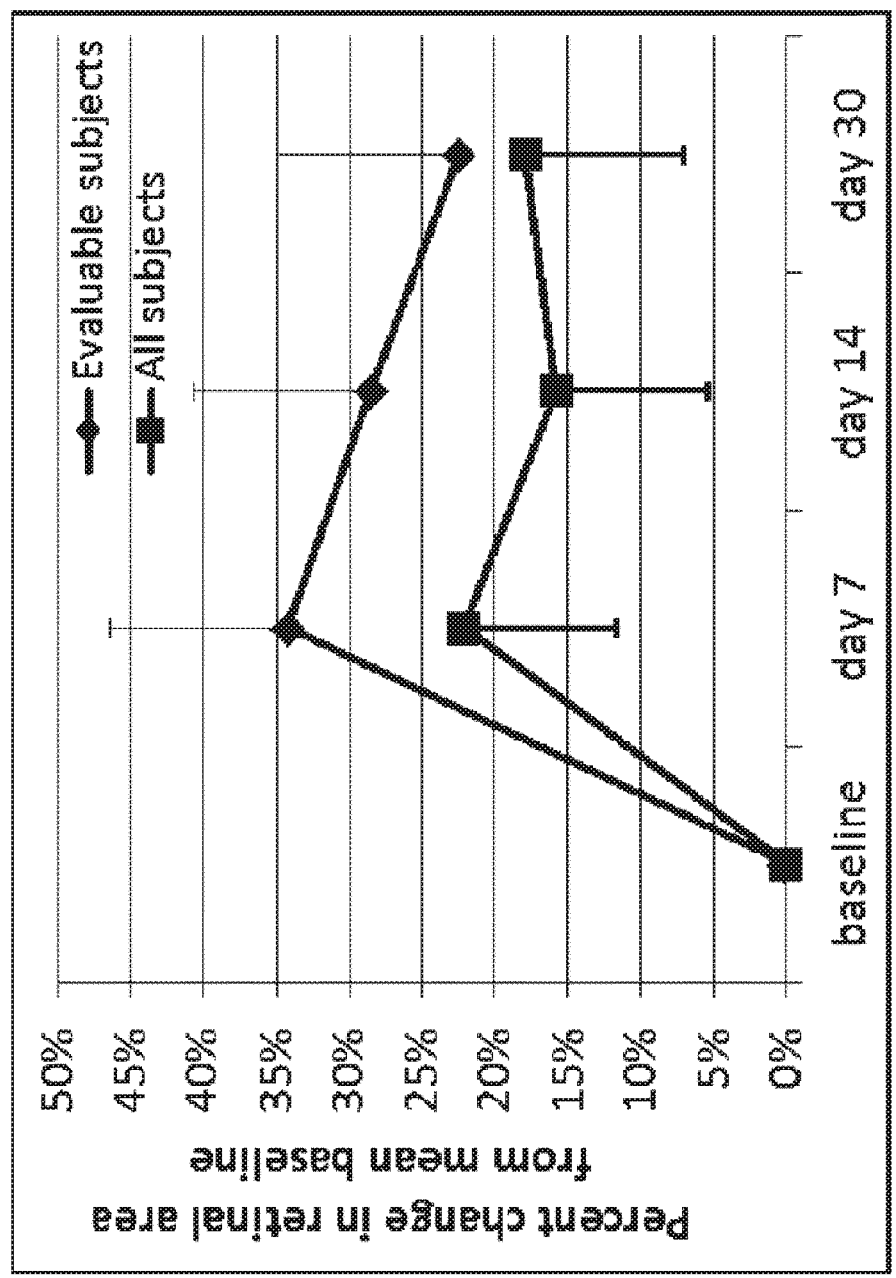

FIG. 2 summarizes the proportion of GVF responders to treatment in both the ITT and per Protocol sets. Dependent on the isopter selected for analysis, the proportion of responders in the ITT group was 44.1-50% at Day 7, 38.2-44.1% at Day 14, and 35.5-41.9% at Day 30. The proportion of responders in the evaluable (per protocol) subset, also dependent on the isopter selected for analysis, was 51.7-60.7% at Day 7, 44.8-53.6% at Day 14, and 34.6-40% at Day 30. When these sets were further separated based on VF severity at baseline, a higher percentage of responders were found in the least severe subgroup, both in the ITT and per protocol sets (FIG. 3, all subjects included, and FIG. 4, 3 subjects excluded). After 7 days of dosing, the average GVF areas from baseline showed statistically significant improvements of 34% at day 7 (p=0.005), 29% at day 14 (p=0.02) and trended towards a statistically significant improvement of 23% at day 30 (p=0.07) in the evaluable (per protocol) RP subjects (n=14). In the ITT set (n=17), average GVF area from baseline improved by 22% at day 7 (p=0.03, statistically significant), 16% at day 14 (p=0.13) and 18% at day 30 (p=0.096) (FIG. 5). FIG. 6 shows the percent of GVF responders to treatment in the ITT set wherein a responder is defined as patients/eyes for whom retinal area, relative to the mean baseline value, increased by at least 20% on 2 consecutive follow-up visits until month 1.

Figure 7:
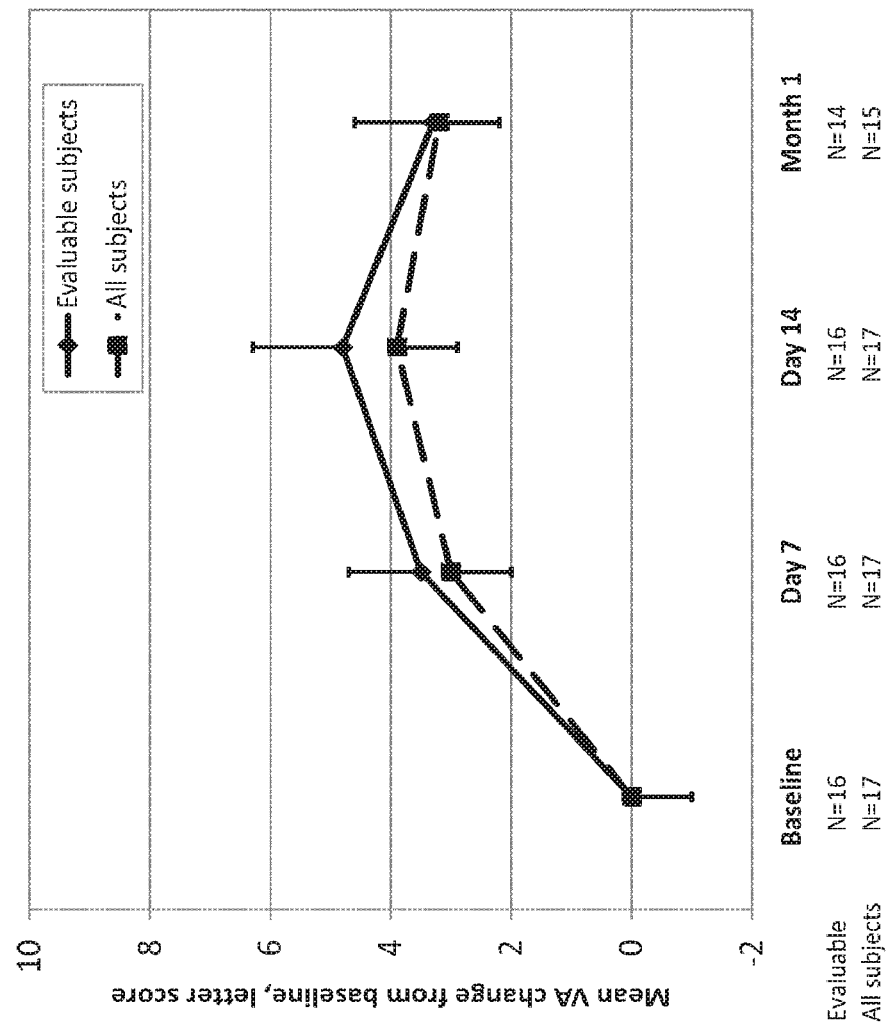
FIG. 7 shows VA results as the mean VA change from baseline, ETDRS letter score, with improvements shown at Day 7, Day 14, or Month 1 for all subjects and the Evaluable subjects, excluding eyes which had baseline VA of zero letters.

Nine of 17 RP subjects (53%) showed an improvement in BCVA over baseline in at least one eye by greater than or equal to 5 ETDRS letters. The VA response was further separated by demographics to evaluate subpopulations which may be more sensitive to the treatment, as shown in Table 2. At day 7, 27% of eyes had a VA improvement of ≥5 ETDRS letters, with 15% of eyes improving by ≥5 to <10 and 12% of eyes improving by ≥10 to <15 letters. At Day 14, 37% of eyes had a VA improvement of ≥5 ETDRS letters, with 28% of eyes improving by ≥5 to <10 and 6% of eyes improving by ≥10 to <15 letters, and 3% of eyes improving by ≥20 letters. At day 30, 34% of eyes had a VA improvement of ≥5 ETDRS letters, with 19% of eyes improving by ≥5 to <10 and 15% of eyes improving by ≥10 to <15 letters. When evaluated based on gene mutation, for the 5 RP subjects with LRAT mutations, 40% of eyes improved by ≥5 at day 7, 60% at day 14, and 50% at day 30. For the 12 RP subjects with RPE65 mutations, 21% of eyes improved by ≥5 at day 7, 23% at day 14, and 30% at day 30. FIG. 7 shows the mean VA change from baseline, ETDRS letter score improvement. At Day 7, Day 14 and Month 1, mean VA improvement for all subjects (ITT group) was found to be 3+/−1 letters, 3.9+/−0.9 letters, and 3.2+/−1.2 letters respectively. The evaluable subset, defined as excluding one eye of one subject and both eyes of another subject, all having baseline VA of zero letters, had mean VA improvement of 3.5+/−1.2 letters, 4.8+/−1.5 letters, and 3.3+/−1.3 letters respectively.

TABLE 2

VA Response* by Baseline Value

| | No. of eyes | % |
|---|---|---|
| Response by age | | |
| <20 years | 2/4 | 50% |
| ≥20 years | 9/30 | 30% |
| Response by gender | | |
| Male | 9/20 | 45% |
| Female | 2/14 | 14% |
| Response by race | | |
| White | 5/20 | 25% |
| Asian | 5/12 | 42% |
| Other | 1/2 | 50% |
| Response by Gene deficiency | | |
| LRAT | 6/10 | 60% |
| RPE65 | 5/24 | 21% |

*VA change from baseline ≥5 letters for 2 consecutive visits between day 7 and month 1.

Figures 8A, 8B:
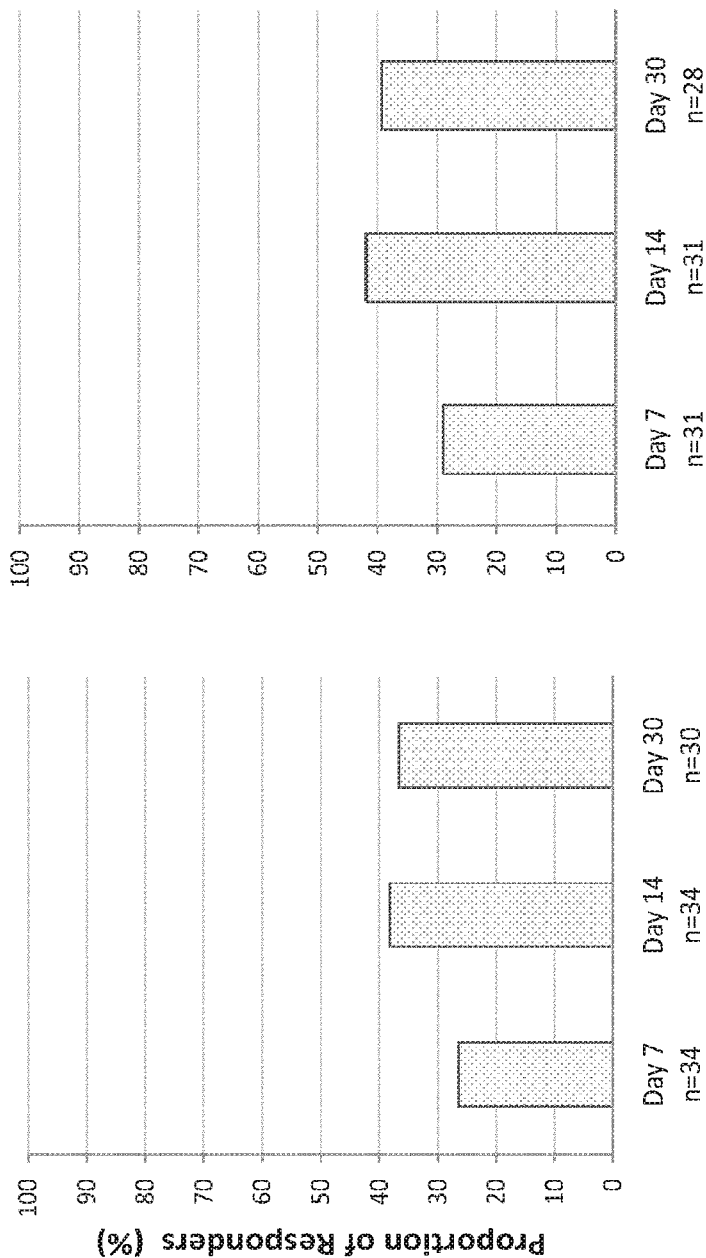
FIGS. 8A and 8B show VA response as the proportion of VA responders with eyes with greater than or equal to 5 letter improvement from baseline in both the ITT (8A) and the Evaluable (8B) subsets.
Figure 9:
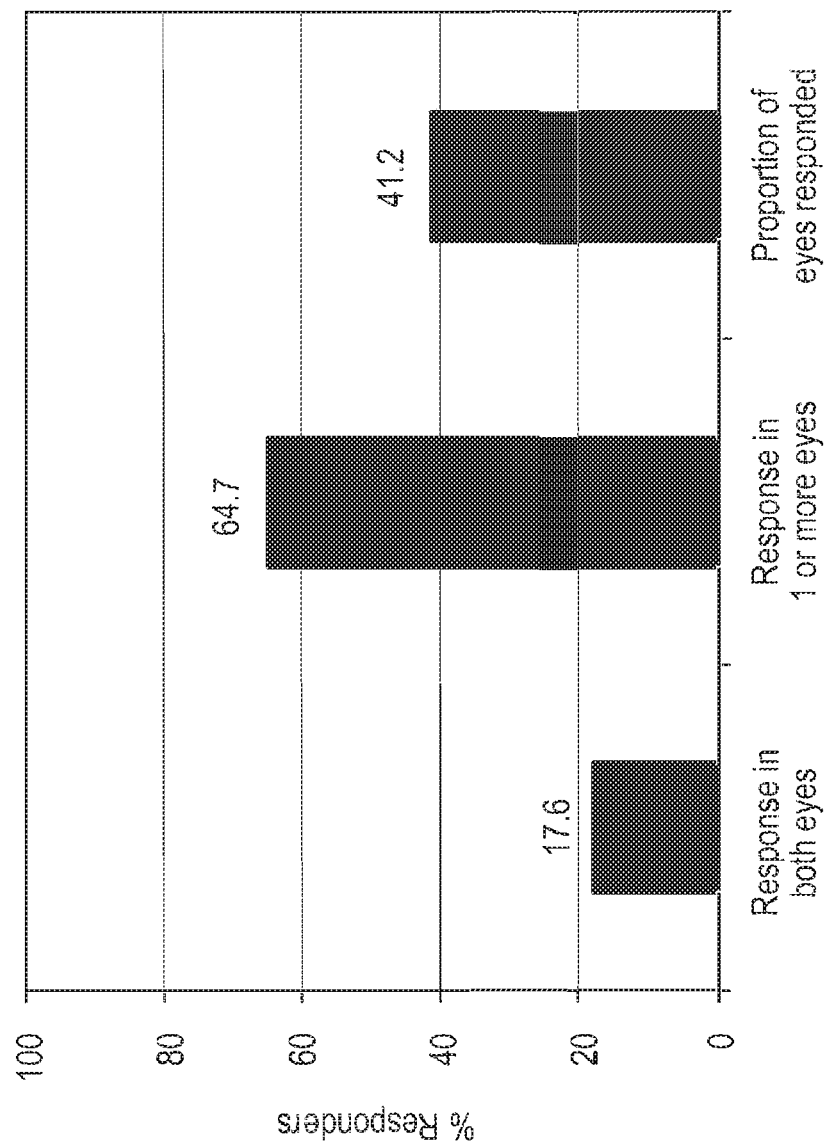
FIG. 9 shows VA response (ITT) as the percent of VA responders with response in both eyes, response in one or more eyes, or proportion of eyes responded, wherein a responder is defined as having an improvement of greater than or equal to 5 ETDRS letters from baseline, or if baseline is zero, a responder is defined as anything above baseline, obtained in two consecutive visits until one month.

FIG. 8A shows the proportion of VA responders in the ITT set when responder is defined as an improvement of greater than or equal to 5 letters from baseline with the exception that if baseline is zero, a responder is defined as anything above baseline. FIG. 8B shows the proportion of VA responders when the evaluable subset excludes eyes with baseline of zero (i.e., such that one eye of one subject and both eyes of another subject are excluded for having a baseline VA=0). FIG. 9 shows the percentage of VA responders in the ITT set when responder is defined as an improvement of greater than or equal to 5 letters from baseline with the exception that if baseline is zero, a responder is defined as anything above baseline, for two consecutive visits until one month.

Baseline visual functions showed a broad range of severely reduced baseline BCVA (0-65 letters) and VF (6-75 degrees) consistent with severe retinal degeneration. In small subsets of RP subjects, the effects of treatment on several parameters of light sensitivity in dim light (night vision), pupillary reflexes, and responses of the visual cortex to potential changes in visual stimuli (functional magnetic resonance imaging, fMRI) were measured.

An fMRI substudy (n=2) of the present study showed activation of several previously quiet areas of the visual and parietal cerebral cortex after treatment, e.g., as measured at day 11.

Several RP subjects across the study self-reported a gain in night vision.

Safety assessments were performed on all RP subjects to provide baseline (pretreatment) and postdose measures. Vital signs were evaluated at screening, on Day −1, predose and 4 hours postdose on treatment days. Triplicate ECG recordings and clinical laboratory tests were performed at screening, on Day −1, and on days 3 and 7. Safety assessments were also done on Day 14/15 and each subsequent visit if the RP subject had ongoing, clinically significant abnormal results at the preceding visit. The clinical laboratory tests performed included hematology, serum chemistry (including total cholesterol, triglycerides, HDL, and LDL), and urinalysis. Analysis of the safety profile indicated that the study treatment was well tolerated, with safety results consistent with the results in healthy adult volunteers (See Example 1). Effects on lipid metabolism, a recognized class effect for retinoids, were observed. Clinically significant laboratory results largely returned to baseline through the resting period. Other adverse events included mild to moderate headache which resolved by the end of the 7-day treatment period for most subjects, nausea which resolved in one day, and photophobia.

Preliminary results in RP subjects with early-onset RP due to mutations in LRAT and RPE65 show a rapid and significant improvement in certain visual function parameters after a 7 day course of treatment with an acceptable safety profile.

Example 3: Safety and Efficacy Study for LCA Subjects

The study of Example 2 was also designed to determine the efficacy of the composition of Example 1 orally administered to human subjects having LCA (caused by mutations of either LRAT or RPE65). Subjects received a once-daily loading dose of the composition orally (40 mg/m$^2$) for 7 days. Subjects were treated on an outpatient basis, but they received study treatment in the research clinic under medical supervision for each day of treatment. Both eyes of each subject were evaluated separately. Protocol-defined assessments of visual function included: best-corrected visual acuity testing using Early Treatment Diabetic Retinopathy Study (ETDRS) testing followed by low/high contrast Smith-Kettlewell Institute Low Luminance (SKILL) charts; visual field testing using Goldmann perimetry; full-field electroretinogram (ERG); and full-field stimulus threshold testing (FST). Baseline ERGs, ETDRS, and SKILL tests were repeated twice. During and after treatment, visual function tests were conducted on Day 1, 7, 9/10, and 14/15.

Summary of Preliminary Efficacy Data in 9 LCA Patients as Well As Two RP Patients of Example 2

A total of 11 subjects were studied, comprising two mutation types (LRAT and RPE65), two disease types (LCA and RP), different age ranges (6 subjects 6-15 years and 5 subjects 21-41 years), and a broad range of baseline visual function, as shown in Table 3. Four distinct ranges of baseline VA were established: hand motion and light perception, VA in the 0-20 letter range, VA in the 20-50 letter range, and VA in the 50-70 letter range. Largest responses in improvement in VA was observed for patients with a modest level of retinal function (VAs in the 20-40 letter range), all of which were treated with 40 mg/m$^2$ of the Composition (FIG. 10). The best responses, 3 lines of improvement, were seen in the younger patients (10-13 years). Relative improvements in visual acuity over baseline for the 11 subjects were monitored for up to 14 months post dosing, demonstrating persistence of clinically meaningful improvements (FIG. 11).

TABLE 3

| Subject | Type | Age | Sex | Race | Dose (mg/m$^2$) | Baseline VA (ltrs) | Best Change from Baseline | Visit |
|---|---|---|---|---|---|---|---|---|
| 1 | LRAT | 10 | F | White | 40 | OD 36 | OD 51 (+15) | Day 8 |
|   | LCA | HOMOZYGOUS C.217_218DELAT, P.MET73ASPFSX47 | | | | OS 26 | OS 51 (+25) | Month 4 |
| 2 | LRAT | 12 | M | White | 40 | OD 9 | OD 18 (+9) | Month 6.5 |
|   | LCA | HOMOZYGOUS C.217_218DELAT, P.MET73ASPFSX47 | | | | OS 7 | OS 25 (+18) | Day 9 |
| 3 | LRAT | 38 | F | White | 40 | OD 0 | OD 5 (+5) | Month 6 |
|   | LCA | HOMOZYGOUS C.217_218DELAT, P.MET73ASPFSX47 | | | | OS 0 | OD 3 (+3) | Month 2.5 |
| 4 | RPE65 | 31 | M | Indian | 40 | OD 0 | OD 1 (+1) | Month 2.5 |
|   | LCA | p.W331X (TGG > TAG) c.992G > A | | | | OS 15 | OS 21 (+6) | Day 14 |
| 5 | RPE65 | 13 | F | Asian | 40 | OD 31 | OD 67 (+36) | Month 4 |
|   | LCA | Leu67Arg CTG > CGG heterozygous - EPP = 3 | | | | OS 34 | OS 63 (+29) | Day 14 |
| 6 | RPE65 | 6 | F | Asian | 40 | OD 64 | OD 70 (+6) | Day 14 |
|   | LCA | Leu67Arg CTG > CGG heterozygous - EPP = 3 | | | | OS 61 | OS 68 (+7) | |
| 7 | RPE65 | 21 | F | Syrian | 40 | OD 60 | OS 60 (0) | Day 14 |
|   | LCA | -/-V19DEL2BP, NT 57 + 58 | | | | OS 52 | OS 55 (+3) | Day 9 |
| 8 | RPE65 | 15 | F | Brazilian | 10 | OD 28 | OD 32 (+4) | Day 9 |
|   | LCA | EXON 4 272 > A R91Q GA/CT EXON 10 1022T > C L341S TC/AG | | | | OS 25 | OS 27 (+2) | |
| 9 | RPE65 | 14 | F | Hispanic | 10 | OD 37 | OD 51 (+14) | Day 14 |
|   | LCA | EXON 4 272G, EXON 10 1022T | | | | OS 47 | OD 46 (−1) | |
| 10 | LRAT | 28 | M | Indian | 40 | OD 71 | OD 82 (+11.5) | Day 9 |
|   | RP | HOMOZYGOUS EXON 2 C.525T > A; P.SER175ARG | | | | OS 60 | OS 74 (+14.5) | Month 1.5 |
| 11 | LRAT | 41 | M | White | 40 | OD 0 | No change | Day 14 |
|   | RP | HOMOZYGOUS EXON 2 C.181T > A3 P.TYR61ASP | | | | OS 1.5 | OD 26 (+24.5) | |

AMA low vision grid analyses of the GVFs from Day 14 for the first 9 patients treated showed that 7 of 9 patients demonstrated marked improvements as detected with either the smaller I4e target (FIG. 12) or the larger V4e target (FIG. 13).

Preliminary data obtained from use of the Children's Visual Function Questionnaire (CVFQ) or Low Luminance Questionnaire (LLQ) have been combined with subjective reports on improvements in activities of daily living, and support the rapid improvement in visual function and prolonged therapeutic benefit of treatment with the Composition.

The study treatment was well tolerated. Adverse events related to treatment included transient photophobia and headaches, vomiting, moderate elevations in triglyceride levels, and a trend toward a decrease in HDL levels in all subjects. Effects on lipid metabolism, a recognized class effect for retinoids, was found to peak at Day 7 of dosing, but returned to baseline within 4 weeks after treatment was completed, as shown in Tables 4-7. Overall, adverse events, including effects on lipid metabolism, were more pronounced in the 40 mg/m2 group relative to the lower dosed 10 mg/m2 group.

TABLE 4

Triglycerides

| | 10 mg/m2 (n = 2) | 40 mg/m2 (n = 9) | Total (n = 11) |
|---|---|---|---|
| Baseline | 0.3 ± 0.0 | 1.0 ± 0.5 | 0.9 ± 0.5 |
| Day 3 | 0.5 ± 0.3 | 1.5 ± 0.7 | 1.3 ± 0.8 |
| % change | 57.1% | 55.8% | 56.0% |
| Day 7 | 0.6 ± 0.2 | 2.0 ± 0.8 | 1.7 ± 1.0 |
| % change | 66.1% | 113.4% | 103.9% |
| Day 9 | 0.4 | 1.6 ± 0.6 | 1.5 ± 0.8 |
| % change | 17.6% | 82.2% | 73.0% |
| Day 14 | — | 1.2 ± 0.5 | 1.2 ± 0.5 |
| % change | — | 12.0% | 12.0% |

TABLE 5

HDL

| | 10 mg/m2 (n = 2) | 40 mg/m2 (n = 9) | Total (n = 11) |
|---|---|---|---|
| Baseline | 1.3 ± 0.1 | 1.1 ± 0.2 | 1.1 ± 0.2 |
| Day 3 | 1.2 ± 0.2 | 0.9 ± 0.2 | 1.0 ± 0.2 |
| % change | −6.3% | −16.2% | −13.7% |
| Day 7 | 1.2 ± 0.2 | 0.8 ± 0.1 | 0.9 ± 0.2 |
| % change | −2.5% | −20.1% | −16.6% |
| Day 9 | 1.3 | 1.0 ± 0.1 | 1.0 ± 0.2 |
| % change | −2.9% | −5.6% | −5.0% |
| Day 14 | — | 1.1 ± 0.2 | 1.1 ± 0.2 |
| % change | — | 5.8% | 5.8% |

TABLE 6

Cholesterol

| | 10 mg/m2 (n = 2) | 40 mg/m2 (n = 9) | Total (n = 11) |
|---|---|---|---|
| Baseline | 4.3 ± 0.0 | 4.0 ± 0.7 | 4.1 ± 0.7 |
| Day 3 | 4.3 ± 0.2 | 3.8 ± 0.6 | 3.9 ± 0.6 |
| % change | −1.2% | −1.3% | −1.3% |
| Day 7 | 4.5 ± 0.3 | 4.3 ± 0.6 | 4.3 ± 0.6 |
| % change | 3.4% | 11.6% | 9.9% |
| Day 9 | 4.5 | 4.5 ± 0.8 | 4.5 ± 0.7 |
| % change | 2.8% | 23.2% | 20.3% |
| Day 14 | — | 4.7 ± 0.6 | 4.7 ± 0.6 |
| % change | — | 18.1% | 18.1% |

TABLE 7

LDL

| | 10 mg/m2 (n = 2) | 40 mg/m2 (n = 9) | Total (n = 11) |
|---|---|---|---|
| Baseline | 2.9 ± 0.1 | 2.5 ± 0.7 | 2.6 ± 0.6 |
| Day 3 | 2.8 ± 0.3 | 2.3 ± 0.4 | 2.4 ± 0.5 |

TABLE 7-continued

LDL

| | 10 mg/m2 (n = 2) | 40 mg/m2 (n = 9) | Total (n = 11) |
|---|---|---|---|
| % change | −2.4% | −0.1% | −0.6% |
| Day 7 | 3.0 ± 0.3 | 2.6 ± 0.7 | 2.7 ± 0.6 |
| % change | 2.2% | 10.3% | 8.7% |
| Day 9 | 2.9 | 3.0 ± 0.7 | 3.0 ± 0.6 |
| % change | 4.6% | 31.3% | 26.0% |
| Day 14 | — | 3.0 ± 0.6 | 3.0 ± 0.6 |
| % change | — | 26.0% | 26.0% |

Example 4: Final Efficacy Assessments in RP and LCA Subjects, Including Those of Examples 2 and 3

A total of 32 subjects were enrolled in the study overall: 14 LCA subjects and 18 RP subjects. All LCA and RP subjects completed the 7-day treatment period. All LCA subjects had at least 6 months of follow-up, with 12 LCA subjects (86%) having at least 12 months of follow-up, and 2 LCA subjects (17%) having at least 2 years of follow-up. The follow-up period for RP subjects tended to be shorter than that of LCA subjects because RP subjects tended to enter the study later and had the option of entering the retreatment study (Example 6 below) before they reached the 12-month time point. All RP subjects had at least 2 months of follow-up, and 13 subjects (72%) had 8 months of follow-up. There were no visits for RP subjects beyond Month 8.

The overall study population had a mean age of 23.9 years (range 6-55) and the majority was female (56%) and Caucasian (56%). LCA subjects were younger on average than RP subjects, with a mean age of 18 years (range 6-38 years) vs 28 years (range 6-55 years) for RP subjects. Nine of 14 LCA subjects were under 18 years, compared to 2 of 18 RP subjects.

The LCA population was predominantly female (71%), whereas the RP population was more balanced (44% female). The racial composition of the two populations was similar, with the LCA population being 50% Caucasian, 21% Asian, 21% Hispanic and 7% other (Syrian), while the RP population was 61% Caucasian, 33% Asian, and 6% Hispanic.

In the overall study population 20 subjects (63%) had a deficiency in RPE65 compared to 12 subjects (38%) with a deficiency in LRAT. The LCA population had an equal number of subjects with each gene mutation, while the RP population had a higher incidence of RPE65 deficiency (13 subjects, 72%). The two LCA subjects who received the 10 mg/m2 dose were both female, Hispanic teenagers with RPE65 deficiency.

The 14 LCA subjects ranged in age from 6 to 38 years, mean 17.9 years with either RPE65 (7 subjects) or LRAT (7 subjects) mutations were evaluated with VA and GVF levels at baseline. Visual Acuity (VA; ETDRS BCVA) ranged from 0-68 letters for the left eye (OS) with a mean of 30.3 letters (~20/250) and ranged from 0-64 letters for the right eye (OD) with a mean of 30.3 letters (~20/250). Visual Field (GVF) for the optimized primary isopter selected for each subject ranged from 0.62-2.81 for the left eye with a mean, log retinal area of 2.0 and ranged from 0.68-2.83 for the right eye with a mean, log retinal area of 2.0.

The 18 RP subjects ranged in age from 6 to 55 years, mean 28.5 years with either RPE65 (13 RP subjects) or LRAT (5 RP subjects) mutations were evaluated with VA and GVF results described in FIG. 2. Both eyes in each RP subject were evaluated independently. Visual Acuity (VA; ETDRS BCVA) ranged from 0-62 letters for the left eye (OS) with a mean of 30.4 letters (~20/250) and ranged from 0-71 letters for the right eye (OD) with a mean of 30.4 letters (~20/250). Visual Field (GVF) for the optimized primary isopter selected for each subject ranged from 0.40-2.53 for the left eye with a mean, log retinal area of 1.8 and ranged from 0.48-2.53 for the right eye with a mean, log retinal area of 1.8.

In the ITT analysis, including all LCA and RP subjects, a substantial majority of LCA subjects (10 of 14, 71%) had an increase in retinal area of at least 20% in at least 1 eye, with a mean duration of response of 269 days (range 5-801 days). Seven LCA subjects (50%) had an increase in retinal area of at least 40% in both eyes, with a mean duration of response of 275 days (range 7-801 days). RPE65-deficient LCA subjects were more likely to respond than LRAT-deficient LCA subjects, but the duration of response was similar for the 2 mutations.

For RP subjects, 8 of 18 subjects (44%) had an increase in retinal area of at least 20% in at least 1 eye, with a mean duration of response of 72 days (range 7-253 days) and 2 subjects (11%) had an increase in retinal area of at least 40% in both eyes, with a mean duration of response of 80 days (range 16-174 days). The response rates were similar for the two gene mutations, but the duration of response was substantially longer in LRAT-deficient eyes than RPE65-deficient eyes (123 vs. 49 days of at least 20% response for LRAT- and RPE65-deficient eyes, respectively, and 104 vs. 67 days of at least 40% response for LRAT- and RPE65-deficient eyes, respectively).

A post hoc analysis was performed to determine the time to initiation of a GVF response occurring within 6 months of treatment. The median time to initiation of a GVF response was 7 days for a response of at least 20%, and 9 days for a response of at least 40%.

Twelve 12 RP subjects (67%) had a VA increase of at least 5 letters from baseline in at least 1 eye, and 1 RP subject (6%) had an increase of at least 10 letters in both eyes. In comparison, 6 LCA subjects (43%) had a VA increase of at least 5 letters from baseline in at least 1 eye, and 3 LCA subjects (25%) had an increase of at least 10 letters in both eyes. The mean duration of both the ≥5 letter and ≥10 letter VA responses was higher in LCA eyes (313 and 316 days, respectively, with a range of 5-801 days for both ≥5 letter and ≥10 letter responses) than in RP eyes (125 days (range 13-246 days) and 112 days (range 13-206 days), respectively). VA response rates were higher for LRAT-deficient RP subjects than RPE65-deficient RP subjects. The median time to initiation of a visual acuity response was 8 days for a response of at least 5 letters, and 7 days for a response of at least 10 letters.

The 2 LCA subjects who received 10 mg/m$^2$ QLT091001 had increases in GVF retinal area of at least 40% in both eyes; however, neither of these subjects had a VA response.

The mean and median change from baseline stayed positive throughout the study. The VA mean change from baseline in LCA subjects was quite variable over time, ranging between 0.5 and 6.6 letters. The median change from baseline was more consistent, particularly after the Month 2 visit when they ranged from 2 to 3 letters. In RP subjects the mean VA change brome baseline ranged from 3 to 4 letters from the Day 14 visit onward, and the median ranged from 1 to 3.5 letters; both the mean and median showed a slight downward trend over time (FIG. 14).

The results of the evaluable analysis, which included subjects who fulfilled major inclusion/exclusion criteria, were generally similar to the ITT analysis.

Other efficacy assessments (including full-field ERG, full-field sensitivity and color vision) were performed on some subjects, however there was not enough data to draw conclusions for the study population.

Selective plasma concentration monitoring was done during the study for 2 LCA subjects who received daily 10 mg/m$^2$ daily doses of the treatment, 6 LCA subjects and 18 RP subjects who received 40 mg/m$^2$ daily doses of the treatment over 7 days. Pharmacokinetic analyses showed the predominant metabolites to be either 9-cis-retinyl oleate or 9-cis-retinyl palmitate and 13,14-dihydro-9-cis-retinoic acid. At 4 hours after dosing, the concentration of these compounds was higher than that of 9-cis-retinyl acetate and 9-cis-retinol.

The results of the children's vision-related quality of life questionnaire did not show consistent improvements after treatment; however interpretation of the results is difficult due to the small number of respondents. The LLQ administered to adults showed increases in the mean score for all of the visual function subcategories for LCA subjects. For RP subjects there were variations but no consistent trends for the visual function subcategories except for extreme lighting, for which there was a slight decrease in ability over the course of the study.

Baseline SD-OCT (Spectralis HRA+OCT) parameters were compared to baseline visual function; baseline SD-OCT and changes were compared to the visual field response to treatment. The average thickness of the outer segment (OS) layer (measured from the outer segment/retinal pigment epithelium border to the inner segment ellipsoid band) was calculated with a computer program aided by manual segmentation.

Thirty-nine of 62 eyes had VA of ≥20 letters (20/400 or better) at baseline. Of these, 36 (92%) had readily detectable OS (>10 µm in thickness) in the fovea. Eighteen of 28 eyes (64%) with LCA and 15/34 eyes (44%) with RP responded to treatment (increase in GVF retinal area of ≥20% at two consecutive study visits). Among these responders, the average baseline thickness of the OS layer (central 20°) was 14.22 µm (reduced by 56% from normal average [32 µm]) in the LCA cohort and 8.63 µm (reduced by 73% from normal) in the RP cohort. Non-responders had average baseline OS thickness of less than 5.72 µm in both cohorts (reduced by ≥82% from normal). The reductions of OS thickness in central 20° were significantly higher in non-responders than responders in the LCA cohort (p=0.003), but not significantly different in the RP cohort (p=0.27). The OS thickness in the central 20° measured at baseline did not change significantly during the follow-up visits.

Treatment with up to 40 mg/m$^2$ for 7 days was well tolerated. All subjects enrolled in the study experienced at least one adverse event (AE) related to treatment. The most common associated AE was headache (88% of subjects), followed by photophobia (50%), and blood triglycerides increased (31%). Treatment resulted in short term deviations from normal in a number of laboratory parameters in a minority of subjects. Most of these parameters had returned to normal in all affected subjects by Day 14 or Month 1. Cholesterol and TGs returned to normal by Month 2 and hematocrit returned to normal by Month 4.

Example 5: Safety Study of Multiple-Dose Administration

A randomized, open-label, placebo-controlled, parallel-design, multiple-dose study was designed to investigate the safety, tolerability and pharmacokinetics of multiple-dose oral administration of the composition of Example 1 in healthy human volunteers. 35 subjects were enrolled. The study consisted of subjects receiving 4 (placebo and 20 mg/m² groups) or 6 (40 and 60 mg/m² groups) consecutive 28-day dosing/washout cycles (7-day dosing and 21-day washout). After the final cycle, subjects were followed up for 2 months. During each cycle, subjects received either a therapeutic dose comprising a once-daily dose of the compositions of Example 1 orally (9-cis-retinyl acetate and 0.1% butylated hydroxyanisole (BHA) in soybean oil) (USP) administered at 20 mg/m², 40 mg/m², 60 mg/m²) or placebo for 7 days, followed by a 21 day resting period during which the subjects did not receive treatment. Subjects were periodically monitored during the cycle for various adverse events, such as headaches, facial flushing and facial burning sensation. Subjects were also monitored for toxicity associated with treatment such as an elevation in triglycerides and decline in high density lipoproteins (HDL). Adverse events observed included headache, photophobia, nausea, ALT increase, elevated triglycerides, and elevated AST.

No new or unexpected adverse events were observed in the study. Up to six repeat treatment cycles with the compositions of Example 1 at doses of 20 mg/m²¹ day, 40 mg/m²¹ day, and 60 mg/m²¹ day for seven days followed by a 21 day washout period was generally safe and well tolerated. The safety profile of repeated treatment cycles was similar to that of one treatment cycle, with an overall trend toward reduction in the severity of the Adverse Events with each subsequent dosing cycle. The safety results of this study further support the use of repeat dosing of pharmaceutical compositions of 9- or 11-cis retinyl esters, including the oral composition of Example 1, in intermittent dosing cycles in subjects with RP.

Interim Pharmacokinetic results of the study were derived from plasma concentrations of 9-cis-retinyl acetate and its metabolites, measured throughout the study period at prescribed time points. The scope of this interim PK analysis encompasses samples from Cohort 1 including the placebo (n=2), 40 mg/m² (n=6) and 60 mg/m² (n=2) dose groups obtained in treatment cycles 1, 2 and 3.

The plasma samples were analyzed by liquid chromatography-mass spectrometry-mass spectrometry (LC/MS/MS) for parent drug and potential metabolites. Noncompartmental (NCA) pharmacokinetic (PK) parameters such as AUC were obtained using the WinNonlin software with observational determination of $C_{max}$, $t_{max}$, and duration of concentrations above baseline (TD).

9-cis-Retinyl acetate plasma concentrations were low and transient, indicative of rapid first-pass metabolism, with further metabolism to non-polar and polar metabolites. At 40 mg/m², administered in repeated seven day cycles, the 9-cis-retinol and retinyl ester metabolites showed slight to modest accumulation on multiple-dosing with higher AUC values on Day 7 in accordance with expectations from Day 1. The longer persisting metabolites had rising daily $C_{min}$ values consistent with modest accumulation and these patterns and concentrations were similar for Cycles 1, 2, and 3 with no accumulation being observed from cycle to cycle Example 6: Effects of Repeated Treatments on Safety and Vision Outcome in Subjects with Inherited Deficiencies of RPE65 or LRAT This study is designed to investigate the effects of repeated treatments on the safety and efficacy of up to three additional courses of the composition of Example 1 orally administered once daily for 7 days to human subjects with LCA or RP due to inherited deficiencies in RPE65 or LRAT. The study was also designed to evaluate whether the up to 3 additional courses of treatment can maintain or improve visual function in these subjects. The study will enroll up to approximately 28 subjects with LCA or RP due to RPE65 or LRAT deficiency. Subjects with LCA are 5-65 years of age (inclusive), and subjects with RP are 18-65 years of age (inclusive). All subjects will have previously received a 7-day treatment course and completed the Day 30 visit according to the study protocol of Example 2. Subjects will meet one of the following criteria at least 1 month after the start of the 7-day treatment course of Example 2: a) Follow-up GVF increased ≤20% from baseline in at least 1 eye; or, b) Follow-up GVF decreased below the highest previous response by ≥20%; or, c) considered a reasonable candidate for retreatment based on regression or lack of response in other parameters of visual function, but who do not meet the other (GVF) criteria.

For each treatment course, subjects will receive an oral dose of the composition of Example 1 once daily for 7 days. The oral dose will be: 40 mg/m² for subjects whose follow-up GVF in at least 1 eye, at least 1 month after the start of the 7-day treatment course does not increase (i.e., increases ≤20% from baseline) (subjects previously treated with a 10 mg/m² dose), or, decreases below the highest previous response by ≥20% (subjects originally treated with 10 or 40 mg/m²); 60 mg/m² for subjects whose follow-up GVF in at least 1 eye, at least 1 month after the start of the 7-day treatment course does not increase (i.e., increases ≤20% from baseline) (subjects originally treated with 40 mg/m²); or, 40 or 60 mg/m², for subjects considered reasonable candidates for retreatment.

Subjects will receive up to 3 courses of study treatment. A minimum of 3 weeks is required between the last day of the previous treatment course and the first day of the next treatment course. At Day 30 (±3 days) after the start of the first and second treatment courses, safety and vision outcome data will be evaluated for retreatment decisions. A subject will receive the second treatment course (once daily dose of the composition of Example 1 for 7 days), with a dose of 40 or 60 mg/m², if there are no safety concerns and: follow-up GVF in at least 1 eye does not increase (i.e., increases ≤20% from the study baseline), or follow-up GVF in at least 1 eye decreases below the highest previous response by ≥20% after the first course of treatment in this study, or the subject does not meet the GVF criteria but is considered as a reasonable candidate for retreatment based on (1) regression or lack of response in other parameters of visual function (e.g., subjective reports of changes in color vision or adaptation to low light), or (2) the potential for further improvement in GVF if GVF response was sustained.

A subject will receive the third treatment course (once daily dose of the composition of Example 1 for 7 days), with a dose of 40 or 60 mg/m², if there are no safety concerns and: follow-up GVF in at least 1 eye decreases below the highest previous response by ≥20% after the second course of treatment, or the subject does not meet the GVF criteria but is considered as a reasonable candidate for retreatment based on (1) regression or lack of response in other parameters of visual function (e.g., subjective reports of changes in color vision or adaptation to low light), or (2) the potential for further improvement in GVF if GVF response is sustained.

Subjects who are not retreated based on the retreatment criteria evaluated at Day 30 (±3 days) will continue to be followed up. Such subjects may start the next treatment course at any subsequent follow-up visit up to Month 12 of the previous treatment course if there are no safety concerns and the subject meets the retreatment criteria as specified for Treatment Course 2 or Treatment Course 3.

Baseline visual function tests will be performed. One Day 0, each subject will receive the first dose of the composition of Example 1. Treatment will be administered for 7 consecutive days (Day 0 to Day 6, inclusive). Blood samples for the study drug and metabolite analysis will be collected for the first and last doses (i.e., 4 hours postdose on Days 0 and 6 and before breakfast on Days 1 and 7). Subjects will have follow-up visits on Days 7/8, 14/15 and 30; and Months 2, 4, 6, 8, 10, and 12 for each treatment course, or up to the start of the next treatment course. Protocol-defined assessments of visual function will include: best-corrected visual acuity testing using ETDRS, visual field testing, full-field electroretinogram (ERG), retinal sensitivity (FST), dynamic pupillometry, nystagmus testing, OCT, FAF, and subject questionnaire.

The previous examples are provided to illustrate but not to limit the scope of the claims. Other variants of the inventions will be readily apparent to those of ordinary skill in the art and are encompassed by the claims. All publications, patents, patent applications and other references cited herein are hereby incorporated by reference.

The invention claimed is:

1. A method of improving visual function in a subject having a deficiency in endogenously produced 11-cis retinal comprising:
   a. administering a first therapeutic dose of a synthetic retinal derivative orally to a subject in need thereof, wherein the first therapeutic dose is administered as a daily dose over a period of 7 days;
   b. providing a resting period of from 14 to 21 days; and
   c. administering a second therapeutic dose of the synthetic retinal derivative to said subject following the end of the resting period.

2. The method of claim 1, wherein the subject has retinitis pigmentosa (RP).

3. The method of claim 1, wherein the subject has Leber congenital amaurosis (LCA).

4. The method of claim 1, wherein the subject has an LRAT gene mutation.

5. The method of claim 1, wherein the subject has a RPE65 gene mutation.

6. The method of claim 1, wherein the synthetic retinal derivative provides replacement of endogenously produced 11-cis-retinal.

7. The method of claim 1, wherein the method further comprises repeating steps b and c one or more times.

8. The method of claim 1, wherein the synthetic retinal derivative is a 9-cis-retinyl ester.

9. The method of claim 8, wherein the retinyl ester is 9-cis-retinyl acetate.

10. A dosing regimen for improving visual function of a subject having a deficiency in endogenously produced 11-cis retinal, wherein the dosing regimen comprises at least, a first therapeutic dose, a second therapeutic dose and a resting period between the first therapeutic dose and the second therapeutic dose, the regimen comprising;
    a. daily administering a first oral dose of a 9- or 11-cis-retinyl ester over a period of 7 days to a subject in need thereof;
    b. providing a resting period of from 14 to about 21 days between the first therapeutic dose and the second therapeutic dose; and
    c. administering the second oral therapeutic dose of a 9- or 11-cis-retinyl ester following the end of the resting period to the subject in need thereof.

11. The dosing regimen of claim 10, wherein the subject has Leber congenital Amaurosis (LCA).

12. The dosing regimen of claim 10, wherein the method further comprises repeating steps b and c one or more times.

13. The dosing regimen of claim 10, wherein the first therapeutic dose is from about 280 mg/m$^2$ to about 420 mg/m2.

14. The dosing regimen of claim 10, wherein the retinyl ester is 9-cis-retinyl acetate.

15. The method of claim 9, wherein the resting period is 21 days.

16. The dosing regimen of claim 14, wherein the resting period is 21 days.

* * * * *